(12) United States Patent
Butt et al.

(10) Patent No.: US 7,083,941 B2
(45) Date of Patent: Aug. 1, 2006

(54) COMPOSITIONS AND METHODS FOR GENDER SORTING

(75) Inventors: Tauseef Butt, Audobon, PA (US); Hiep Tuan Tran, West Chester, PA (US)

(73) Assignee: Lifesensors, Inc., Malvern, PA (US)

( * ) Notice: Subject to any disclaimer, the term of this patent is extended or adjusted under 35 U.S.C. 154(b) by 67 days.

(21) Appl. No.: 10/475,433

(22) PCT Filed: Apr. 23, 2002

(86) PCT No.: PCT/US02/12590

§ 371 (c)(1),
(2), (4) Date: Apr. 23, 2004

(87) PCT Pub. No.: WO02/086446

PCT Pub. Date: Oct. 31, 2002

(65) Prior Publication Data

US 2004/0203010 A1    Oct. 14, 2004

Related U.S. Application Data

(60) Provisional application No. 60/286,010, filed on Apr. 23, 2001.

(51) Int. Cl.
*C12Q 1/02* (2006.01)
*C12N 5/10* (2006.01)
*C12N 1/19* (2006.01)

(52) U.S. Cl. ............... 435/29; 435/7.21; 435/7.31; 435/7.32; 435/254.2; 435/254.21; 435/252.3; 435/325; 435/410

(58) Field of Classification Search ............ 435/7.31, 435/29, 254.11, 254.2, 325
See application file for complete search history.

(56) References Cited

U.S. PATENT DOCUMENTS

| 6,029,080 A | 2/2000 | Reynnells |
| 6,365,339 B1 | 4/2002 | Daum |
| 6,506,570 B1 * | 1/2003 | Phelps ................ 435/7.21 |
| 6,512,839 B1 | 1/2003 | Toelken |

FOREIGN PATENT DOCUMENTS

| WO | 97/11094 | * | 3/1997 |

OTHER PUBLICATIONS

Burdge et al. Determination of oestrogen concentrations in bovine plasma by a recombinant oestrogen receptor-reporter gene yeast bioassay. Analyst. Dec. 1998;123(12):2585-8.*
Hoffmann et al. Determination of free and conjugated oestrogens in peripheral blood plasma, feces and urine of cattle throughout pregnancy. Exp Clin Endocrinol Diabetes. 1997;105(5):296-303.*
Zondek et al. Observations on the determination of fetal sex in early pregnancy. Contrib Gynecol Obstet. 1979;5:91-108.*
Schmitz et al. Application of the beta-glucuronidase gene fusion system to *Saccharomyces□□cerevisiae*. Curr Genet. Mar. 1990;17(3):261-4.*
Tan et al. Sulfation is rate limiting in the futile cycling between estrone and estrone sulfate in enriched periportal and perivenous rat hepatocytes. Drug Metab Dispos. Mar. 2001;29(3):335-46.*
Burdge et al. Determination of oestrogen concentrations in bovine plasma by a recombinant□□oestrogen receptor-reporter gene yeast bioassay. Analyst. Dec. 1998;123(12):2585-8.*
Coldham et al. Evaluation of a recombinant yeast cell estrogen screening assay.□□Environ Health Perspect. Jul. 1997;105(7):734-42.*
Gill et al. In vivo estrogen synthesis by the developing chicken (*Gallus gallus*) embryo. Gen Comp Endocrinol. Feb. 1983;49(2):176-86.*
Klein et al. Estrogen levels in childhood determined by an ultrasensitive recombinant cell bioassay. J Clin Invest. Dec. 1994;94(6):2475-80.*
Sikorski, R.S. et al. "A System of Shuttle Vectors and Yeast Host Strains Designed for Efficient Manipulation of DNA in *Saccharomyces cerevisiae*"; Genetics, 122: 19-27 (1989).
Jefferson, R.A. et al. "β-Glucuronidase from *Escherichia coli* as a gene-fusion marker"; Proc. Natl. Acad. Sci. USA, 83: 8447-8451 (1986).
Russell, W.M. et al. "Identification and Cloning of *gusA*, Encoding a New β-Glucuronidase from *Lactobacillus gasseri* ADH"; Applied and Environmental Microbiology, 67(3): 1253-1261 (2001).
Tran, H.T. et al. "Reconstruction of Ligand-Dependent Transactivation of *Choristoneura fumiferana* Ecdysone Receptor in Yeast"; Molecular Endocrinology, 15(7): 1140-1153 (2001).
Li, S. et al. "The Yeast *ULP2* (*SMT4*) Gene Encodes a Novel Protease Specific for the Ubiquitin-Like Smt3 Protein"; Molecular and Cellular Microbiology, 20(7): 2367-2377 (2000).
Crittenden, L.B. et al. "Embryonic Infection with the Endogenous Avian Leukosis Virus Rous-Associated Virus-0 Alters Responses to Exogenous Avian Leukosis Virus Infection"; Journal of Virology, 61(3): 722-725 (1987).
Arnold, K.E. et al. "Primary sex ratios in birds: problems with molecular sex identification of undeveloped eggs"; Molecular Ecology, 12: 3451-3458 (2003).

(Continued)

Primary Examiner—Daniel M. Sullivan
(74) Attorney, Agent, or Firm—Kathleen D. Rigaut; Robert C. Netter, Jr.; Dann Dorfman Herrell and Skillman

(57) ABSTRACT

A yeast based transactivation assay for gender sorting is disclosed.

29 Claims, 23 Drawing Sheets

OTHER PUBLICATIONS

Walfish, P.G. et al. "Yeast hormone response element assays detect and characterize GRIP1 coactivator-dependent activation of transcription by thyroid and retinoid nuclear receptors"; Proc. Natl. Acad. Sci. USA, 94: 3697-3702 (1997).

Bachmair, A. et al. "In vivo half-life of a protein is a function of its amino-terminal residue"; Science, 234(4773): 179-86 (1986) [Abstract].

Lyttle, C.R. et al. "Human estrogen receptor regulation in a yeast model system and studies on receptor agonists and antagonists"; J. Steroid Biochem. Mol. Biol., 42(7): 677-85 (1992) [Abstract].

Mumberg, D. et al. "Yeast vectors for the controlled expression of heterologous proteins in different genetic backgrounds"; Gene, 156: 119-122 (1995) [Abstract].

Kim, K.I. et al. "A New SUMO-1-specific Protease, SUSP1, That Is Highly Expressed in Reproductive Organs"; J. Biol. Chem., 275(19): 14102-14106 (2000) [Abstract].

Graumann, K. et al. "Structural and functional analysis of N-terminal point mutants of the human estrogen receptor"; J. Steroid Biochem. Mol. Biol., 57(5-6): 293-300 (1996) [Abstract].

Butt, T.R. et al. "Reconstruction of Mammalian Nuclear Receptor Function in *Saccharomyces cervisiae*"; Julian Davies, Charles Harshberger (Eds.), Manual of Industrial Microbiology and Biotechnology, 2nd Edition, Section V. American Society for Microbiology, 527-538 (1999).

Marathe, S.V. et al. "Vectors with the gus reporter gene for identifying and quantitating promoter regions in *Saccharomyces cerevisiae*"; Gene, 154(1): 105-7 (1995) [Abstract].

Yeh, E.T. et al. "Ubiquitin-like proteins: new wines in new bottles"; Gene, 248(1-2): 1-14 (2000) [Abstract].

Schwienhorst, I. et al. "SUMO conjugation and deconjugation"; Mol. Gen. Genet., 263(5): 771-86 (2000) [Abstract].

Mahajan, R. et al. "A small ubiquitin-related polypeptide involved in targeting RanGAP1 to nuclear pore complex protein RanBP2"; Cell, 88(1): 97-107 (1997) [Abstract].

Suzuki, T. et al. "A new 30-kDa ubiquitin-related SUMO-1 hydrolase from bovine brain", Biol. Chem. 274(44): 31131-4 (1999) [Abstract].

Gill, D.V. et al. "In vivo estrogen synthesis by the developing chicken (*Gallus gallus*) embryo"; Gen. Comp. Endocrinol., 49(2): 176-86 (1983) [Abstract].

Tanabe, Y. et al. "Production and secretion of sex steroid hormones by the testes, the ovary, and the adrenal glands of embryonic and young chickens (*Gallus domesticus*)"; Gen. Comp. Endocrinol., 39(1): 26-33 (1979), Title.

Guichard, A. et al. "Radioimmunoassay of steroids produced by cultured chick embryonic gonads: differences according to age, sex and side"; Gen. Comp. Endocrinol., 32(3): 255-65 (1977), Title.

Teng, C.T. et al. "Studies on sex-organ development. The hormonal regulation of steroidogenesis and adenosine 3':5'—cyclic monophosphate in embryonic-chick ovary"; Biochem J., 162(1): 123-4 (1977) [Abstract].

Glahn, R.P. et al. "Evaluation of sex differences in embryonic heart rates"; Poult. Sci., 66(8): 1398-401 (1987) [Abstract].

Bacon, L.D. et al. "Association of the slow feathering (K) and an endogenous viral (ev21) gene on the Z chromosome of chickens"; Poult. Sci., 67(2): 191-7 (1988) [Abstract].

Clinton, M. "A rapid protocol for sexing chick embryos (*Gallus g. domesticus*)"; Anim. Genet., 25(5): 361-2 (1994) [Abstract].

Ellegren, H. "First gene on the avian W chromosome (CHD) provides a tag for universal sexing of non-ratite birds"; Proc. R. Soc. Lond. B. Biol. Sci., 263(1377): 1635-41 (1996) [Abstract].

Ricks, C.A. et al. "The embryonated egg: a practical target for genetic based advances to improve poultry production"; Poult. Sci., 82(6): 931-8 (2003) [Abstract].

Arnold, K.E. et al.; Proceedings: Biological Sciences, 270(1530): 216-219 (2004) [Abstract].

Johnson, L.A. "Advances in gender preselection in swine"; J. Reprod. Fertil. Suppl., 52: 255-66 (1997) [Abstract].

Rath, D. et al. "In Vitro Production of Sexed Embryos for Gender Preselection: High-Speed Sorting of X-Chromosome Bearing Sperm to Produce Piglets After Embryo Transfer"; J. Anim. Sci., 77: 3346-3352 (1999).

Gledhill, B.L. "Selection and separation of X- and Y-chromosome-bearing mammalian sperm"; Gamete Res., 20(3); 377-95 (1988) [Abstract].

Gueye, E.H. "Women and family poultry production in rural Africa"; Dev. Pract., 10(1): 98-102 (2000) [Abstract].

Horsey, R. "The art of chicken sexing"; UCL Working Papers in Linguistics, 14: 107-117 (2002) [Abstract].

Johnson, B.D. "Imaging Technique Hatches Egg-Sorting System"; Nov. 2002 [http://www.photonics.com/spectra/applications/XQ/ASP/aoaid.282/QX/read.htm].

Livestock Knowledge Transfer "Gender Determination in Chick Embryos"; Poultry: 2001:514 [Abstract].

Martin, B. "Chicken Sexing"; The Specialist Chicken Sexer; [http://www3.turboweb.net.au/~garrys/poultry/chickensexing.html].

Laffon, G. "In France, experts sort out gender of chicks"; The Miami Herald Aug. 3, (2003) [http://www.miami.com/mld/miamiherald/news/world/6445389.htm?template=contentModu . . . ].

"Gender Sort System"; Embrex, Inc.—Pharmaceutical Business Review [http:www.pharmaceutical-business-review.com/companyprofile.asp?guid=A72CCD15-71 . . . ].

Clinton, M., et al., "Sexing chick embryos: a rapid and simple protocol," British Poultry Science, 42:134-138, (2001).

Phelps, P., et al., "Automated identification of male layer chicks prior to hatch," World's Poultry Science Journal, 59:32-37, (2003).

Ellegren, H., "Hens, cocks and avian sex determination," EMBO reports 2(3):192-196, (2001).

\* cited by examiner

Gender Sorting Sensor
Standard Microplate Assay
(Example III)
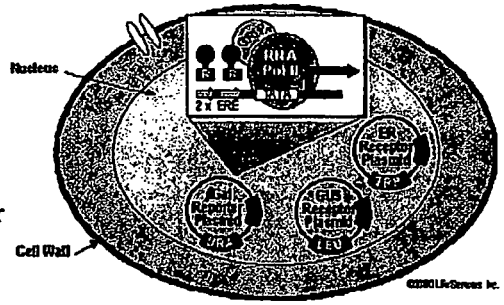
Yeast strains containing
- Estrogen receptor (ER) vector
- ER responsive reporter
- Secretory β-glucuronidase vector
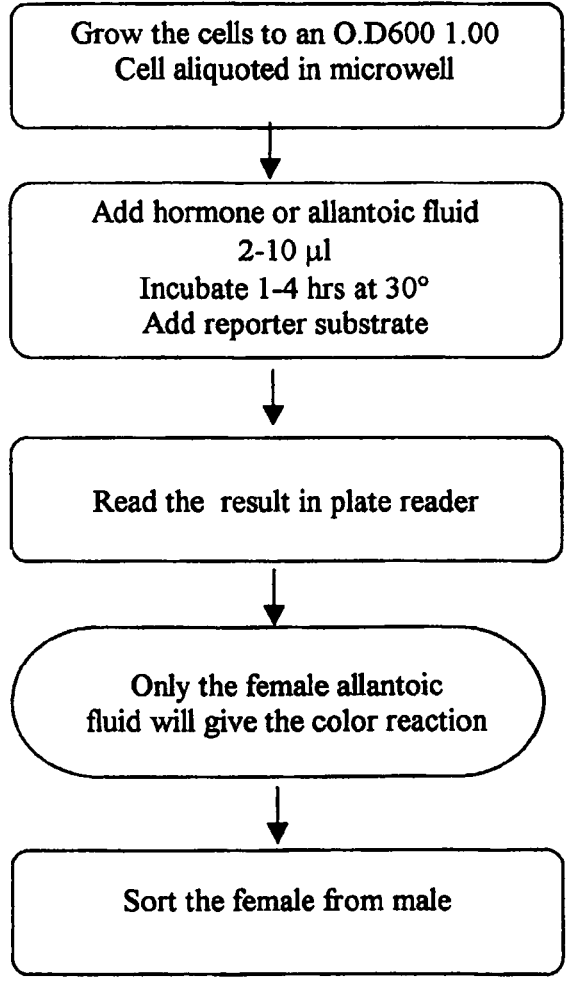
Figure 2A

Improved Gender Sorting Sensor
(Example 4)

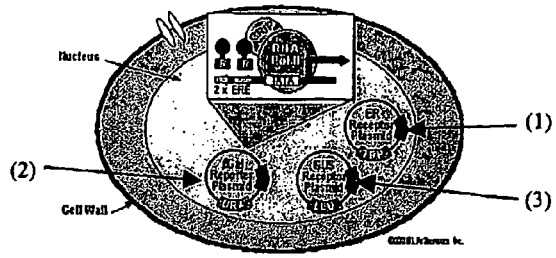

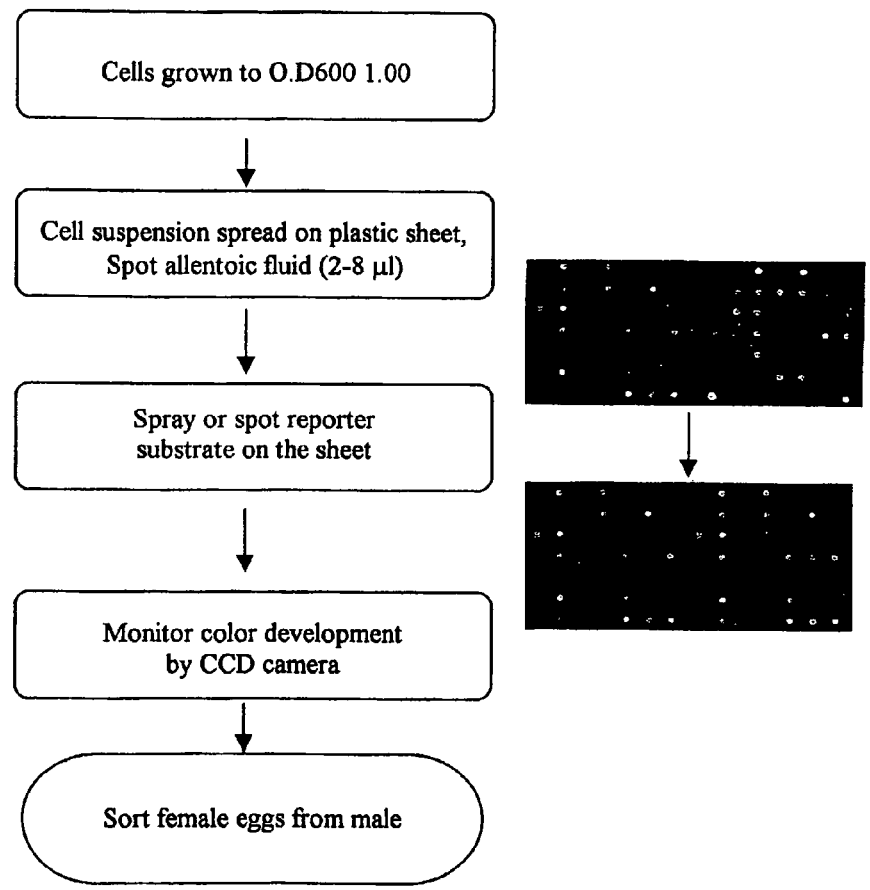

Improved Strategies:
1) Reengineer receptor to become superactive transactivator.
2) Reporter genes changed to phosphatase or green flourescence protein or another enzyme that reports a color signal.
3) β-glucuronidase can be mutated to become superactive.
   Other mammalian glucuronidases or sufatases can be used that are more efficient in cleaving estrogenic conjugates that are present in allantoic fluids.

The yeast cells containing all 3 plasmids can be mutagenized and the best allantoic responder can be isolated by genetic selection.

Figure 2B

Gender Sorting Sensor Development

Proof of Concept
(Example II)

Estrogen conjugate to be cleaved
before sensor activation

Estrogen conjugate + Estrogen   =   No signal
Responsive Yeast

Estrogen conjugates
+
β-glucuronidase
↓
glucuronides
+
17β estradiol
↓

Only the female allentoic fluid gives the response

Figure 6A
Figure 6B
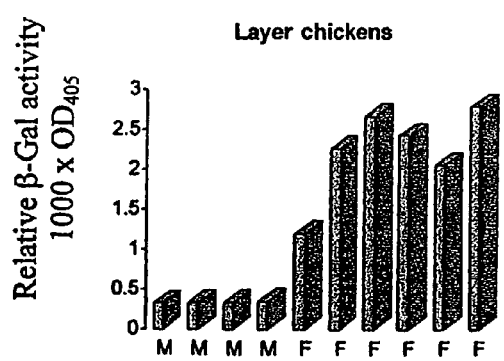
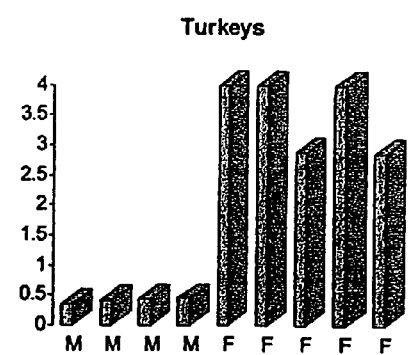

Figure 9: Nucleic acid sequence of CYC1-based estrogen inducible reporter YRpE2 (SEQ ID NO: 7)

```
gaattctgaaccagtcctaaaacgagtaaataggaccggcaattcttcaagcaataaacaggaataccaat
tattaaaagataacttagtcagatcgtacaataaagctttgaagaaaaatgcgccttattcaatctttgct
ataaaaaatggcccaaaatctcacattggaagacatttgatgacctcatttctttcaatgaagggcctaac
ggagttgactaatgttgtgggaaattggagcgataagcgtgcttctgccgtggccaggacaacgtatactc
atcagataacagcaatacctgatcactacttcgcactagtttctcggtactatgcatatgatccaatatca
aaggaaatgatagcattgaaggatgagactaatccaattgaggagtggcagcatatagaacagctaaaggg
tagtgctgaaggaagcatacgatacccccgcatggaatgggataatatcacaggaggtactagactacccttt
catcctacataaatagacgcatataagtacgcatttaagcataaacacgcactatgccgttcttctcatgt
atatatatatacaggcaacacgcagatataggtgcgacgtgaacagtgagctgtatgtgcgcagctcgcgt
tgcattttcggaagcgctcgttttcggaaacgctttgaagttcctattccgaagttcctattctctagaaa
gtataggaacttcagagcgcttttgaaaaccaaaagcgctctgaagacgcactttcaaaaaaccaaaaacg
caccggactgtaacgagctactaaaatattgcgaataccgcttccacaaacattgctcaaaagtatctctt
tgctatatatctctgtgctatatccctatataacctacccatccacctttcgctccttgaacttgcatcta
aactcgacctctacatcttttatgtttatctctagtattactctttagacaaaaaaattgtagtaagaact
attcatagagtgaatcgaaaacaatacgaaaatgtaaacatttcctatacgtagtatatagagacaaaata
gaagaaaccgttcataattttctgaccaatgaagaatcatcaacgctatcactttctgttcacaaagtatg
cgcaatccacatcggtatagaatataatcggggatgcctttatcttgaaaaaatgcacccgcagcttcgct
agtaatcagtaaacgcgggaagtggagtcaggcttttttatggaagagaaaatagacaccaaagtagcct
tcttctaaccttaacggacctacagtgcaaaaagttatcaagagactgcattatagagcgcacaaaggaga
aaaaaagtaatctaagatgctttgttagaaaaatagcgctctcgggatgcattttgtagaacaaaaaaga
agtatagattctttgttggtaaaatagcgctctcgcgttgcatttctgttctgtaaaaatgcagctcagat
tctttgtttgaaaaattagcgctctcgcgttgcatttttgttttacaaaaatgaagcacagattcttcgtt
ggtaaaatagcgctttcgcgttgcatttctgttctgtaaaaatgcagctcagattctttgtttgaaaaatt
agcgctctcgcgttgcattttgttctacaaaatgaagcacagatgcttcgttaacaaagatatgctattg
aagtgcaagatggaaacgcagaaaatgaaccggggatgcgacgtgcaagattacctatgcaatagatgcaa
tagtttctccaggaaccgaaatacatacattgtcttccgtaaagcgctagactatatattattatacaggt
tcaaatatactatctgtttcagggaaaactcccaggttcggatgttcaaaattcaatgatgggtaacaagt
acgatcgtaaatctgtaaaacagtttgtcggatattaggctgtatctcctcaaagcgtattcgaatatcat
tgagaagctgcagcgtcacatcggataataatgatggcagccattgtagaagtgccttttgcatttctagt
ctctttctcggtctagctagttttactacatcgcgaagatagaatcttagatcacactgcctttgctgagc
tggatcaatagagtaacaaaagagtggtaaggcctcgttaaaggacaaggacctgagcggaagtgtatcgt
acagtagacggagtatactagtatagtctatagtccgtggaattctcatgtttgacagcttatcatcgata
agcttgcttttcaattcatcttttttttttttgttcttttttttgattccggtttctttgaaatttttttg
attcggtaatctccgagcagaaggaagaacgaaggaaggagcacagacttagattggtatatatacgcata
tgtggtgttgaagaaacatgaaattgcccagtattcttaacccaactgcacagaacaaaaacctgcaggaa
acgaagataaatcatgtcgaaagctacatataaggaacgtgctgctactcatcctagtcctgttgctgcca
agctatttaatatcatgcacgaaaagcaaacaaacttgtgtgcttcattggatgttcgtaccaccaaggaa
ttactggagttagttgaagcattaggtcccaaaatttgtttactaaaaacacatgtggatatcttgactga
ttttccatggagggcacagttaagccgctaaaggcattatccgccaagtacaattttttactcttcgaag
acagaaaatttgctgacattggtaatacagtcaaattgcagtactctgcgggtgtatacagaatagcagaa
tgggcagacattacgaatgcacacggtgtggtgggcccaggtattgttagcggtttgaagcaggcggcgga
agaagtaacaaaggaacctagaggcctttttgatgttagcagaattgtcatgcaagggctccctagctactg
gagaatatactaagggtactgttgacattgcgaagagcgacaaagattttgttatcggctttattgctcaa
agagacatgggtggaagagatgaaggttacgattggttgattatgacacccggtgtgggtttagatgacaa
gggagacgcattgggtcaacagtatagaaccgtggatgatgtggtctctacaggatctgacattattattg
ttggaagaggactatttgcaaagggaagggatgctaaggtagagggtgaacgttacagaaaagcaggctgg
gaagcatatttgagaagatgcggccagcaaaactaaaaactgtattataagtaaatgcatgtatactaaa
ctcacaaattagagcttcaatttaattatatcagttattacccgatcaaaaatcatcgcttcgctgattaa
ttaccccagaaataaggctaaaaaactaatcgcattatcatcctatggttgttaatttgattcgttcattt
gaaggtttgtggggccaggttactgccaattttttcctcttcataaccataaaagctagtattgtagaatct
ttattgttcggagcagtgcggcgcgaggcacatctgcgtttcaggaacgcgaccggtgaagacgaggacgc
acggaggagagtcttccttcggagggctgtcacccgctcggcggcttctaatccgtacttcaatatagcaa
tgagcagttaagcgtattactgaaagttccaaagagaaggttttttttaggctaatcgacgtcgacaatctt
acatggtctacctttgatgacaacgaaaccattctttctcaaggcagaacattgcattgggtaggtggcgg
```

Figure 9 continued

```
aggcaccagcgtcagcatttcaaaggtgtgttcttcgtcagacatgttttagtgtgtgaatgaaataggt
gtatgttttcttttgctagacaataattaggaacaaggtaagggaactaaagtgtagaataagattaaa
aagaagaacaagttgaaaggcaagttgaaatttcaagaaaaagtcaattgaagtacagtaaattgacct
gaatatatctgagttccgacaacaatgagtttaccaaagagaacaatggaataggaaactttgaacgaaga
aaggaaagcaggaaaggaaaaaattttaggctcgaggtccaaagtcaggtcacagtgacctgatcaaagt
tctcgaggtccaaagtcaggtcacagtgacctgatcaaagttctcgagcagatccgccaggcgtgtatata
gcgtggatggccaggcaactttagtgctgacacatacaggcatatatatgtgtgcgacgacacatgatc
atatggcatgcatgtgctctgtatgtatataaaactcttgttttcttcttttctctaaatattctttccttt
atacattaggtcctttgtagcataaattactatacttctatagacacgcaaacacaaatacacacactaaa
ttaataatgaccggatccggagcttggctgttgcccgtctcactggtgaaaagaaaaaccaccctggcgcc
caatacgcaaaccgcctctccccgcgcgttggccgattcattaatgcagctggcacgacaggtttcccgac
ttaatcgccttgcagcacatccccctttcgccagctggcgtaatagcgaagaggcccgcaccgatcgccct
tcccaacagttgcgcagcctgaatggcgaatggcgctttgcctggtttccggcaccagaagcggtgccgga
aagctggctggagtgcgatcttcctgaggccgatactgtcgtcgtcccctcaaactggcagatgcacggtt
acgatgcgcccatctacaccaacgtaacctatcccattacggtcaatccgccgtttgttcccacggagaat
ccgacgggttgttactcgctcacatttaatgttgatgaaagctggctacaggaaggccagacgcgaattat
ttttgatggcgttaactcggcgtttcatctgtggtgcaacgggcgctgggtcggttacggccaggacagtc
gtttgccgtctgaatttgacctgagcgcattttacgcgccggagaaaaccgcctcgcggtgatggtgctg
cgttggagtgacggcagttatctggaagatcaggatatgtggcggatgagcggcattttccgtgacgtctc
gttgctgcataaaccgactacacaaatcagcgatttccatgttgccactcgctttaatgatgatttcagcc
gcgctgtactggaggctgaagttcagatgtgcggcgagttgcgtgactacctacgggtaacagtttcttta
tggcagggtgaaacgcaggtcgccagcggcaccgcgcctttcggcggtgaaattatcgatgagcgtggtgg
ttatgccgatcgcgtcacactacgtctgaacgtcgaaaacccgaaactgtggagcgccgaaatcccgaatc
tctatcgtgcggtggttgaactgcacaccgccgacggcacgctgattgaagcagaagcctgcgatgtcggt
ttccgcgaggtgcggattgaaaatggtctgctgctgctgaacggcaagccgttgctgattcgaggcgttaa
ccgtcacgagcatcatcctctgcatggtcaggtcatggatgagcagacgatggtgcaggatatcctgctga
tgaagcagaacaactttaacgccgtgcgctgttcgcattatccgaaccatccgctgtggtacacgctgtgc
gaccgctacggcctgtatgtggtggatgaagccaatattgaaacccacggcatggtgccaatgaatcgtct
gaccgatgatccgcgctggctaccggcgatgagcgaacgcgtaacgcgaatggtgcagcgcgatcgtaatc
acccgagtgtgatcatctggtcgctggggaatgaatcaggccacggcgctaatcacgacgcgctgtatcgc
tggatcaaatctgtcgatccttcccgcccggtgcagtatgaaggcggcggagccgacaccacggccaccga
tattatttgcccgatgtacgcgcgcgtggatgaagaccagcccttcccggctgtgccgaaatggtccatca
aaaaatggctttcgctacctggagagacgcgcccgctgatcctttgcgaatacgcccacgcgatgggtaac
agtcttggcggtttcgctaaatactggcaggcgtttcgtcagtatcccgtttacagggcggcttcgtctg
ggactgggtggatcagtcgctgattaaatatgatgaaaacggcaacccgtggtcggcttacggcggtgatt
ttggcgatacgccgaacgatcgccagttctgtatgaacggtctggtctttgccgaccgcacgccgcatcca
gcgctgacggaagcaaaacaccagcagcagttttttccagttccgtttatccgggcaaaccatcgaagtgac
cagcgaatacctgttccgtcatagcgataacgagctcctgcactggatggtggcgctggatggtaagccgc
tggcaagcggtgaagtgcctctggatgtcgctccacaaggtaaacagttgattgaactgcctgaactaccg
cagccggagagcgccgggcaactctggctcacagtacgcgtagtgcaaccgaacgcgaccgcatggtcaga
agccgggcacatcagcgcctggcagcagtggcgtctggcggaaaacctcagtgtgacgctccccgccgcgt
cccacgccatcccgcatctgaccaccagcgaaatggattttgcatcgagctgggtaataagcgttggcaa
tttaaccgccagtcaggctttctttcacagatgtggattggcgataaaaaacaactgctgacgccgctgcg
cgatcagttcacccgtgcaccgctggataacgacattggcgtaagtgaagcgacccgcattgaccctaacg
cctgggtcgaacgctggaaggcggcgggccattaccaggccgaagcagcgttgttgcagtgcacggcagat
acacttgctgatgcggtgctgattacgaccgctcacgcgtggcagcatcaggggaaaaccttatttatcag
ccggaaaacctaccggattgatggtagtggtcaaatggcgattaccgttgatgttgaagtggcgagcgata
caccgcatccggcgcggattggcctgaactgccagctggcgcaggtagcagagcgggtaaactggctcgga
ttagggccgcaagaaaactatcccgaccgccttactgccgcctgttttgaccgctgggatctgccattgtc
agacatgtatacccgtacgtcttcccgagcgaaaacggtctgcgctgcgggacgcgcgaattgaattatg
gcccacaccagtggcgcggcgacttccagttcaacatcagccgctacagtcaacagcaactgatggaaacc
agccatcgccatctgctgcacgcggaagaaggcacatggctgaatatcgacggtttccatatggggattgg
tggcgacgactcctggagcccgtcagtatcggcggaattccagctgagcgccggtcgcgctgcctcgcgcg
tttcggtgatgacggtgaaaacctctgacacatgcagctcccggagacggtcacagcttgtctgtaagcgg
atgccgggagcagacaagcccgtcagggcgcgtcagcgggtgttggcgggtgtcggggcgcagccatgacc
```

Figure 9 continued

```
cagtcacgtagcgatagcggagtgtatactggcttaactatgcggcatcagagcagattgtactgagagtg
caccatatgcggtgtgaaataccgcacagatgcgtaaggagaaaataccgcatcaggcgctcttccgcttc
ctcgctcactgactcgctgcgctcggtcgttcggctgcggcgagcggtatcagctcactcaaaggcggtaa
tacggttatccacagaatcaggggataacgcaggaaagaacatgtgagcaaaaggccagcaaaaggccagg
aaccgtaaaaaggccgcgttgctggcgtttttccataggctccgcccccctgacgagcatcacaaaaatcg
acgctcaagtcagaggtggcgaaacccgacaggactataaagataccaggcgtttccccctggaagctccc
tcgtgcgctctcctgttccgaccctgccgcttaccggatacctgtccgcctttctcccttcgggaagcgtg
gcgctttctcatagctcacgctgtaggtatctcagttcggtgtaggtcgttcgctccaagctgggctgtgt
gcacgaaccccccgttcagcccgaccgctgcgccttatccggtaactatcgtcttgagtccaacccggtaa
gacacgacttatcgccactggcagcagccactggtaacaggattagcagagcgaggtatgtaggcggtgct
acagagttcttgaagtggtggcctaactacggctacactagaaggacagtatttggtatctgcgctctgct
gaagccagttaccttcggaaaaagagttggtagctcttgatccggcaaacaaaccaccgctggtagcggtg
gtttttttgtttgcaagcagcagattacgcgcagaaaaaaaggatctcaagaagatcctttgatcttttct
acggggtctgacgctcagtggaacgaaaactcacgttaagggattttggtcatgagattatcaaaaaggat
cttcacctagatccttttaaattaaaaatgaagttttaaatcaatctaaagtatatatgagtaaacttggt
ctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgat
accgcgagacccacgctcaccggctccagatttatcagcaataaaccagccagccggaagggccgagcgca
gaagtggtcctgcaactttatccgcctccatccagtctattaattgttgccgggaagctagagtaagtagt
tcgccagttaatagtttgcgcaacgttgttgccattgctgcaggcatcgtggtgtcacgctcgtcgtttgg
tatggcttcattcagctccggttcccaacgatcaaggcgagttacatgatcccccatgttgtgcaaaaaag
cggttagctccttcggtcctccgatcgttgtcagaagtaagttggccgcagtgttatcactcatggttatg
gcagcactgcataattctcttactgtcatgccatccgtaagatgcttttctgtgactggtgagtactcaac
caagtcattctgagaatagtgtatgcggcgaccgagttgctcttgcccggcgtcaacacgggataataccg
cgccacatagcagaactttaaaagtgctcatcattggaaaacgttcttcggggcgaaaactctcaaggatc
ttaccgctgttgagatccagttcgatgtaacccactcgtgcacccaactgatcttcagcatcttttacttt
caccagcgtttctgggtgagcaaaaacaggaaggcaaaatgccgcaaaaaagggaataagggcgacacgga
aatgttgaatactcatactcttccttttcaatattattgaagcatttatcagggttattgtctcatgagc
ggatacatatttgaatgtatttagaaaaataaacaataggggttccgcgcacatttccccgaaaagtgcc
acctgacgtctaagaaaccattattatcatgacattaacctataaaaataggcgtatcacgaggcccttc
gtcttcaa
```

Figure 10: Nucleic acid sequence of SSA4-based estrogen inducible
reporter YRpE2SSA4-lacZ (SEQ ID NO: 8)

```
gaattctgaaccagtcctaaaacgagtaaataggaccggcaattcttcaagcaataaacaggaataccaat
tattaaaagataacttagtcagatcgtacaataaagctttgaagaaaaatgcgccttattcaatctttgct
ataaaaaatggcccaaaatctcacattggaagacatttgatgacctcatttctttcaatgaagggcctaac
ggagttgactaatgttgtgggaaattggagcgataagcgtgcttctgccgtggccaggacaacgtatactc
atcagataacagcaatacctgatcactacttcgcactagtttctcggtactatgcatatgatccaatatca
aaggaaatgatagcattgaaggatgagactaatccaattgaggagtggcagcatatagaacagctaaaggg
tagtgctgaaggaagcatacgataccccgcatggaatgggataatatcacaggaggtactagactacctt
catcctacataaatagacgcatataagtacgcatttaagcataaacacgcactatgccgttcttctcatgt
atatatatatacaggcaacacgcagatataggtgcgacgtgaacagtgagctgtatgtgcgcagctcgcgt
tgcattttcggaagcgctcgttttcggaaacgctttgaagttcctattccgaagttcctattctctagaaa
gtataggaacttcagagcgcttttgaaaaccaaaagcgctctgaagacgcactttcaaaaaaccaaaaacg
caccggactgtaacgagctactaaaatattgcgaataccgcttccacaaacattgctcaaaagtatctctt
tgctatatatctctgtgctatatccctatataacctacccatccacctttcgctccttgaacttgcatcta
aactcgacctctacatttttatgtttatctctagtattactctttagacaaaaaaattgtagtaagaact
attcatagagtgaatcgaaaacaatacgaaaatgtaaacatttcctatacgtagtatatagagacaaaata
gaagaaaccgttcataattttctgaccaatgaagaatcatcaacgctatcactttctgttcacaaagtatg
cgcaatccacatcggtatagaatataatcggggatgcctttatcttgaaaaaatgcacccgcagcttcgct
agtaatcagtaaacgcgggaagtggagtcaggcttttttatggaagagaaaatagacaccaaagtagcct
tcttctaaccttaacggacctacagtgcaaaaagttatcaagagactgcattatagagcgcacaaggaga
aaaaaagtaatctaagatgctttgttagaaaaatagcgctctcgggatgcattttttgtagaacaaaaaga
agtatagattctttgttggtaaaatagcgctctcgcgttgcatttctgttctgtaaaaatgcagctcagat
tctttgtttgaaaaattagcgctctcgcgttgcattttttgttttacaaaaatgaagcacagattcttcgtt
ggtaaaatagcgctttcgcgttgcatttctgttctgtaaaaatgcagctcagattctttgtttgaaaaatt
agcgctctcgcgttgcattttgttctacaaaatgaagcacagatgcttcgttaacaaagatatgctattg
aagtgcaagatggaaacgcagaaaatgaaccggggatgcgacgtgcaagattacctatgcaatagatgcaa
tagtttctccaggaaccgaaatacatacattgtcttccgtaaagcgctagactatatattattatacaggt
tcaaatatactatctgtttcagggaaaactcccaggttcggatgttcaaaattcaatgatgggtaacaagt
acgatcgtaaatctgtaaaacagtttgtcggatattaggctgtatctcctcaaagcgtattcgaatatcat
tgagaagctgcagcgtcacatcggataataatgatggcagccattgtagaagtgcctttttgcatttctagt
ctctttctcggtctagctagtttttactacatcgcgaagatagaatcttagatcacactgcctttgctgagc
tggatcaatagagtaacaaaagagtggtaaggcctcgttaaaggacaaggacctgagcggaagtgtatcgt
acagtagacggagtatactagtatagtctatagtccgtggaattctcatgtttgacagcttatcatcgata
agcttttcaattcaattcatcatttttttttttattcttttttttttgatttcggtttctttgaaattttttttg
attcggtaatctccgaacagaaggaagaacgaaggaaggagcacagacttagattggtatatatacgcata
tgtagtgttgaagaaacatgaaattgcccagtattcttaacccaactgcacagaacaaaaacctgcaggaa
acgaagataaatcatgtcgaaagctacatataaggaacgtgctgctactcatcctagtcctgttgctgcca
agctatttaatatcatgcacgaaaagcaaacaaacttgtgtgcttcattggatgttcgtaccaccaaggaa
ttactggagttagttgaagcattaggtcccaaaatttgtttactaaaaacacatgtggatatcttgactga
tttttccatggagggcacagttaagccgctaaaggcattatccgccaagtacaattttttactcttcgaag
acagaaaatttgctgacattggtaatacagtcaaattgcagtactctgcgggtgtatacagaatagcagaa
tgggcagacattacgaatgcacacggtgtggtgggcccaggtattgttagcggtttgaagcaggcggcaga
agaagtaacaaaggaacctagaggccttttgatgttagcagaattgtcatgcaagggctccctatctactg
gagaatatactaagggtactgttgacattgcgaagagcgacaaagatttgttatcggctttattgctcaa
agagacatgggtggaagagatgaaggttacgattggttgattatgacacccggtgtgggtttagatgacaa
gggagacgcattgggtcaacagtatagaaccgtggatgatgtggtctctacaggatctgacattattattg
ttggaagaggactatttgcaaagggaagggatgctaaggtagagggtgaacgttacagaaaagcaggctgg
gaagcatatttgagaagatgcggccagcaaaactaaaaaactgtattataagtaaatgcatgtatactaaa
ctcacaaattagagcttcaatttaattatatcagttattaccctcgacctcgaattcctgcaggatatct
ggatcgatccacaagcttgcatgcctgcaggtcgactctggtcacagtgaccggtcacagtgacctatgg
aagcaccaagaaaaaggaagttaaacaaaacactgattcaataagcaaggggggaagctccttagtttga
cgacagtaacaaaatgttcgtataaattgaacgaaactcaagccaataaaggacttttcagaggcctatct
cttctttctccacaactttcgaataaaaaccactaataaaaagtaaataacaaaaacaagaaaaaaaataa
acaaaacaataatcatgggatccaccatgattacggattcactggccgtcgttttacaacgtcgtgactgg
gaaaaccctggcgttacccaacttaatcgccttgcagcacatccccctttcgccagctggcgtaatagcga
```

Figure 10 continued

```
agaggcccgcaccgatcgcccttcccaacagttgcgcagcctgaatggcgaatggcgctttgcctggtttc
cggcaccagaagcggtgccggaaagctggctggagtgcgatcttcctgaggccgatactgtcgtcgtcccc
tcaaactggcagatgcacggttacgatgcgcccatctacaccaacgtaacctatcccattacggtcaatcc
gccgtttgttcccacggagaatccgacgggttgttactcgctcacatttaatgttgatgaaagctggctac
aggaaggccagacgcgaattattttttgatggcgttaactcggcgtttcatctgtggtgcaacgggcgctgg
gtcggttacggccaggacagtcgtttgccgtctgaatttgacctgagcgcattttttacgcgccggagaaaa
ccgcctcgcggtgatggtgctgcgttggagtgacggcagttatctggaagatcaggatatgtggcggatga
gcggcattttccgtgacgtctcgttgctgcataaaccgactacacaaatcagcgatttccatgttgccact
cgctttaatgatgatttcagccgcgctgtactggaggctgaagttcagatgtgcggcgagttgcgtgacta
cctacgggtaacagtttctttatggcagggtgaaacgcaggtcgccagcggcaccgcgcctttcggcggtg
aaattatcgatgagcgtggtggttatgccgatcgcgtcacactacgtctgaacgtcgaaaacccgaaactg
tggagcgccgaaatcccgaatctctatcgtgcggtggttgaactgcacaccgccgacggcacgctgattga
agcagaagcctgcgatgtcggtttccgcgaggtgcggattgaaaatggtctgctgctgctgaacggcaagc
cgttgctgattcgaggcgttaaccgtcacgagcatcatcctctgcatggtcaggtcatggatgagcagacg
atggtgcaggatatcctgctgatgaagcagaacaactttaacgccgtgcgctgttcgcattatccgaacca
tccgctgtggtacacgctgtgcgaccgctacggcctgtatgtggtggatgaagccaatattgaaacccacg
gcatggtgccaatgaatcgtctgaccgatgatccgcgctggctaccggcgatgagcgaacgcgtaacgcga
atggtgcagcgcgatcgtaatcacccgagtgtgatcatctggtcgctggggaatgaatcaggccacggcgc
taatcacgacgcgctgtatcgctggatcaaatctgtcgatccttcccgcccggtgcagtatgaaggcggcg
gagccgacaccacggccaccgatattatttgcccgatgtacgcgcgcgtggatgaagaccagcccttcccg
gctgtgccgaaatggtccatcaaaaaatggctttcgctacctggagagacgcgcccgctgatcctttgcga
atacgcccacgcgatgggtaacagtcttggcggtttcgctaaatactggcaggcgtttcgtcagtatcccc
gtttacagggcggcttcgtctgggactgggtggatcagtcgctgattaaatatgatgaaaacggcaaccca
tggtcggcttacggcggtgatttggcgatacgccgaacgatcgccagttctgtatgaacggtctggtctt
tgccgaccgcacgccgcatccagcgctgacggaagcaaaacaccagcagcagttttttccagttccgtttat
ccgggcaaaccatcgaagtgaccagcgaataccctgttccgtcatagcgataacgagctcctgcactggatg
gtggcgctggatggtaagccgctggcaagcggtgaagtgcctctggatgtcgctccacaaggtaaacagtt
gattgaactgcctgaactaccgcagccggagagcgccgggcaactctggctcacagtacgcgtagtgcaac
cgaacgcgaccgcatggtcagaagccggcacatcagcgcctggcagcagtggcgtctggcggaaaacctc
agtgtgacgctccccgccgcgtcccacgccatcccgcatctgaccaccagcgaaatggattttgcatcga
gctgggtaataagcgttggcaatttaaccgccagtcaggctttctttcacagatgtggattggcgataaaa
aacaactgctgacgccgctgcgcgatcagttcacccgtgcaccgctggataacgacattggcgtaagtgaa
gcgacccgcattgaccctaacgcctgggtcgaacgctggaaggcggcgggccattaccaggccgaagcagc
gttgttgcagtgcacggcagatacacttgctgatgcggtgctgattacgaccgctcacgcgtggcagcatc
aggggaaaaccttatttatcagccggaaaacctaccggattgatggtagtggtcaaatggcgattaccgtt
gatgttgaagtggcgagcgatacaccgcatccggcgcggattggcctgaactgccagctggcgcaggtagc
agagcgggtaaactggctcggattagggccgcaagaaaactatcccgaccgccttactgccgcctgttttg
accgctgggatctgccattgtcagacatgtatacccgtacgtcttcccgagcgaaaacggtctgcgctgc
gggacgcgcgaattgaattatggcccacaccagtggcgcggcgacttccagttcaacatcagccgctacag
tcaacagcaactgatggaaaccagccatcgccatctgctgcacgcggaagaaggcacatggctgaatatcg
acggtttccatatggggattggtggcgacgactcctggagcccgtcagtatcggcggaattccagctgagc
gccggtcgctaccattaccagttggtctggtgtcaaaaataataataagagctcgaattcgctgcctcgcg
cgtttcggtgatgacggtgaaaacctctgacacatgcagctcccggagacggtcacagcttgtctgtaagc
ggatgccgggagcagacaagcccgtcagggcgcgtcagcgggtgttggcgggtgtcggggcgcagccatga
cccagtcacgtagcgatagcggagtgtatactggcttaactatgcggcatcagagcagattgtactgagag
tgcaccatatgcggtgtgaaataccgcacagatgcgtaaggagaaaataccgcatcaggcgctcttccgct
tcctcgctcactgactcgctgcgctcggtcgttcggctgcggcgagcggtatcagctcactcaaaggcggt
aatacggttatccacagaatcaggggataacgcaggaaagaacatgtgagcaaaaggccagcaaaaggcca
ggaaccgtaaaaaggccgcgttgctggcgtttttccataggctccgcccccctgacgagcatcacaaaaat
cgacgctcaagtcagaggtggcgaaacccgacaggactataaagataccaggcgtttccccctggaagctc
cctcgtgcgctctcctgttccgaccctgccgcttaccggatacctgtccgcctttctcccttcgggaagcg
tggcgctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacccggt
aagacacgacttatcgccactggcagcagccactggtaacaggattagcagagcgaggtatgtaggcggtg
ctacagagttcttgaagtggtggcctaactacggctacactagaaggacagtatttggtatctgcgctctg
```

Figure 10 continued

```
ctgaagccagttaccttcggaaaaagagttggtagctcttgatccggcaaacaaaccaccgctggtagcgg
tggttttttgtttgcaagcagcagattacgcgcagaaaaaaggatctcaagaagatcctttgatcttt
ctacggggtctgacgctcagtggaacgaaaactcacgttaagggattttggtcatgagattatcaaaaagg
atcttcacctagatccttttaaattaaaaatgaagtttaaatcaatctaaagtatatatgagtaaacttg
gtctgacagttaccaatgcttaatcagtgaggcacctatctcagcgatctgtctatttcgttcatccatag
ttgcctgactccccgtcgtgtagataactacgatacgggagggcttaccatctggccccagtgctgcaatg
ataccgcgagacccacgctcaccggctccagatttatcagcaataaaccagccagccggaagggccgagcg
cagaagtggtcctgcaactttatccgcctccatccagtctattaattgttgccgggaagctagagtaagta
gttcgccagttaatagtttgcgcaacgttgttgccattgctgcaggcatcgtggtgtcacgctcgtcgttt
ggtatggcttcattcagctccggttcccaacgatcaaggcgagttacatgatcccccatgttgtgcaaaaa
agcggttagctccttcggtcctccgatcgttgtcagaagtaagttggccgcagtgttatcactcatggtta
tggcagcactgcataattctcttactgtcatgccatccgtaagatgcttttctgtgactggtgagtactca
accaagtcattctgagaatagtgtatgcggcgaccgagttgctcttgcccggcgtcaacacgggataatac
cgcgccacatagcagaactttaaaagtgctcatcattggaaaacgttcttcggggcgaaaactctcaagga
tcttaccgctgttgagatccagttcgatgtaacccactcgtgcacccaactgatcttcagcatcttttact
ttcaccagcgtttctgggtgagcaaaaacaggaaggcaaaatgccgcaaaaaagggaataagggcgacacg
gaaatgttgaatactcatactcttccttttcaatattattgaagcatttatcagggttattgtctcatga
gcggatacatatttgaatgtatttagaaaaataaacaatagggttccgcgcacatttccccgaaaagtg
ccacctgacgtctaagaaaccattattatcatgacattaacctataaaaataggcgtatcacgaggcccct
tcgtcttcaa
```

Figure 11: Nucleic acid sequence of yeast expression vector for human
estrogen receptor alpha - YEpE12-ERα (SEQ ID NO: 9)

```
ggatcccattaccgacatttgggcgctatacgtgcatatgttcatgtatgtatctgtatttaaaacacttt
tgtattattttttcctcatatatgtgtataggtttatacggatgatttaattattacttcaccacccttta
ttcaggctgatatcttagccttgttactagttagaaaaagacattttttgctgtcagtcactgtcaagagat
tctttttgctggcatttcttctagaagcaaaaagagcgatgcgtcttttccgctgaaccgttccagcaaaaa
agactaccaacgcaatatggattgtcagaatcatataaaagagaagcaaataactccttgtcttgtatcaa
ttgcattataatatcttcttgttagtgcaatatcatatagaagtcatcgaaatagatattaagaaaaacaa
actgtaacgaattcattatgcagatcttcgtcaagacgttaaccggtaaaaccataactctagaagttgaa
tcttccgataccatcgacaacgttaagtcgaaaattcaagacaaggaaggcattccacctgatcaacaaag
attgatctttgccggtaagcagctcgaggacggtagaacgctgtctgattacaacattcagaaggagtcga
ccttacatcttgtcttaagactaagaggtggtatgaccatgaccctccacaccaaagcatctgggatggcc
ctactgcatcagatccaagggaacgagctggagcccctgaaccgtccgcagctcaagatcccctggagcg
gcccctgggcgaggtgtacctggacagcagcaagcccgccgtgtacaactaccccgagggcgccgcctacg
agttcaacgccgcggccgccgccaacgcgcaggtctacggtcagaccggcctcccctacggccccgggtct
gaggctgcggcgttcggctccaacggcctggggggtttccccccactcaacagcgtgtctccgagcccgct
gatgctactgcacccgccgccgcagctgtcgccttttcctgcagccccacggccagcaggtgccctactacc
tggagaacgagcccagcggctacacggtgcgcgaggccggcccgccggcattctacaggccaaattcagat
aatcgacgccagggtggcagagaaagattggccagtaccaatgacaagggaagtatggctatggaatctgc
caaggagactcgctactgtgcagtgtgcaatgactatgcttcaggctaccattatggagtctggtcctgtg
agggctgcaaggccttcttcaagagaagtattcaaggacataacgactatatgtgtccagccaccaaccag
tgcaccattgataaaaacaggaggaagagctgccaggcctgccggctccgcaaatgctacgaagtgggaat
gatgaaggtgggatacgaaaagaccgaagaggagggagaatgttgaaacacaagcgccagagagatgatg
gggagggcaggggtgaagtggggtctgctggagacatgagagctgccaacctttggccaagcccgctcatg
atcaaacgctctaagaagaacagcctggccttgtccctgacggccgaccagatggtcagtgccttgttgga
tgctgagccccccatactctattccgagtatgatcctaccagacccttcagtgaagcttcgatgatgggct
tactgaccaacctggcagacagggagctggttcacatgatcaactgggcgaagagggtgccaggctttgtg
gatttgaccctccatgatcaggtccaccttctagaatgtgcctgctagagatcctgatgattggtctcgt
ctggcgctccatggagcacccagtgaagctactgtttgctcctaacttgctcttggacaggaaccagggaa
aatgtgtagagggcatggtggagatcttcgacatgctgctggctacatcatctcggttccgcatgatgaat
ctgcagggagaggagtttgtgtgcctcaaatctattattttgcttaattctggagtgtacacatttctgtc
cagcaccctgaagtctctggaagagaaggaccatatccaccgagtcctggacaagatcacagacactttga
tccacctgatggccaaggcaggcctgacccctgcagcagcagcaccagcggctggcccagctcctcctcatc
ctctcccacatcaggcacatgagtaacaaaggcatggagcatctgtacagcatgaagtgcaagaacgtggt
gcccctctatgacctgctgctggagatgctggacgcccaccgcctacatgcgcccactagccgtggaggggg
catccgtggaggagacggaccaaagccacttggccactgcgggctctacttcatcgcattccttgcaaaag
tattacatcacgggggaggcagagggtttccctgccacagtctgagagctccctggcgaattgtaccaaga
tggcctttggtgggttgaagaaggaaaaagacagaaacgacttaattacctacttgaaaaaagcctgtgag
taaacaggccccttttcctttgtcgatatcatgtaattagttatgtcacgcttacattcacgccctccccc
cacatccgctctaaccgaaaaggaaggagttagacaacctgaagtctaggtccctatttatttttttatag
ttatgttagtattaagaacgttatttatatttcaaattttttcttttttttctgtacagacgcgtgtacgca
tgtaacattatactgaaaaccttgcttgagaaggttttgggacgctcgaaggctttaatttgcaagcttat
cgatgataagctgtcaaacatgagaattcggtcgaaaaaagaaaaggagagggccaagagggagggcattg
gtgactattgagcacgtgagtatacgtgattaagcacacaaaggcagcttggagtatgtctgttattaatt
tcacaggtagttctggtccattggtgaaagtttgcggcttgcagagcacagaggccgcagaatgtgctcta
gattccgatgctgacttgctgggtattatatgtgtgcccaatagaaagagaacaattgacccggttattgc
aaggaaaatttcaagtcttgtaaaagcatataaaaatagttcaggcactccgaaatacttggttggcgtgt
ttcgtaatcaacctaaggaggatgttttggctctggtcaatgattacggcattgatatcgtccaactgcat
ggagatgagtcgtggcaagaataccaagagttcctcggtttgccagttattaaaagactcgtatttccaaa
agactgcaacatactactcagtgcagcttcacagaaacctcattcgtttattcccttgtttgattcagaag
caggtgggacaggtgaacttttggattggaactcgatttctgactgggttggaaggcaagagagccccgaa
agcttacattttatgttagctggtggactgacgccagaaaatgttggtgatgcgcttagattaaatggcgt
tattggtgttgatgtaagcggaggtgtggagacaaatggtgtaaaagactctaacaaaatagcaaatttcg
tcaaaaatgctaagaaataggttattactgagtagtatttatttaagtattgtttgtgcacttgcctgcag
cttctcaatgatattcgaatacgctttgaggagatacagcctaatatccgacaaactgttttacagattta
cgatcgtacttgttacccatcattgaattttgaacatccgaacctgggagttttccctgaaacagatagta
```

Figure 11 continued

```
tatttgaacctgtataataatatatagtctagcgctttacggaagacaatgtatgtatttcggttcctgga
gaaactattgcatctattgcataggtaatcttgcacgtcgcatccccggttcattttctgcgtttccatct
tgcacttcaatagcatatctttgttaacgaagcatctgtgcttcattttgtagaacaaaaatgcaacgcga
gagcgctaattttcaaacaaagaatctgagctgcattttacagaacagaaatgcaacgcgaaagcgcta
ttttaccaacgaagaatctgtgcttcattttgtaaaacaaaaatgcaacgcgagagcgctaattttcaa
acaaagaatctgagctgcattttacagaacagaaatgcaacgcgagagcgctattttaccaacaaagaat
ctatacttcttttttgttctacaaaaatgcatcccgagagcgctattttctaacaaagcatcttagatta
ctttttttctcctttgtgcgctctataatgcagtctcttgataacttttttgcactgtaggtccgttaaggt
tagaagaaggctactttggtgtctattttctcttccataaaaaaagcctgactccacttcccgcgtttact
gattactagcgaagctgcgggtgcattttttcaagataaaggcatcccgattatattctataccgatgtg
gattgcgcatactttgtgaacagaaagtgatagcgttgatgattcttcattggtcagaaaattatgaacgg
tttcttctattttgtctctatatactacgtataggaaatgtttacattttcgtattgttttcgattcactc
tatgaatagttcttactacaatttttttgtctaaagagtaatactagagataaacataaaaatgtagagg
tcgagtttagatgcaagttcaaggagcgaaaggtggatgggtaggttatataggatatagcacagagata
tatagcaaagagatacttttgagcaatgtttgtggaagcggtattcgcaatattttagtagctcgttacag
tccggtgcgtttttggttttttgaaagtgcgtcttcagagcgcttttggttttcaaaagcgctctgaagtt
cctatactttctagagaataggaacttcggaataggaacttcaaagcgtttccgaaaacgagcgcttccga
aaatgcaacgcgagctgcgcacatacagctcactgttcacgtcgcacctatatctgcgtgttgcctgtata
tatatatacatgagaagaacggcatagtgcgtgtttatgcttaaatgcgtacttatatgcgtctatttatg
taggatgaaaggtagtctagtacctcctgtgatattatcccattccatgcggggtatcgtatgcttccttc
agcactacccttagctgttctatatgctgccactcctcaattggattagtctcatccttcaatgctatca
tttcctttgatattggatcatatgcatagtaccgagaaactagtgcgaagtagtgatcaggtattgctgtt
atctgatgagtatacgttgtcctggccacggcagaagcacgcttatcgctccaatttcccacaacattagt
caactccgttaggcccttcattgaaagaaatgaggtcatcaaatgtcttccaatgtgagattttgggccat
tttttatagcaaagattgaataaggcgcatttttcttcaaagctttattgtacgatctgactaagttatct
tttaataattggtattcctgtttattgcttgaagaattgccggtcctatttactcgttttaggactggttc
agaattcttgaagacgaaagggcctcgtgatacgcctattttataggttaatgtcatgataataatggtt
tcttagacgtcaggtggcacttttcggggaaatgtgcgcggaacccctatttgtttatttttctaaataca
ttcaaatatgtatccgctcatgagacaataaccctgataaatgcttcaataatattgaaaaaggaagagta
tgagtattcaacatttccgtgtcgccttattcccttttttgcggcattttgccttcctgttttttgctcac
ccagaaacgctggtgaaagtaaaagatgctgaagatcagttgggtgcacgagtgggttacatcgaactgga
tctcaacagcggtaagatccttgagagttttcgccccgaagaacgttttccaatgatgagcacttttaaag
ttctgctatgtggcgcggtattatcccgtgttgacgccgggcaagagcaactcggtcgccgcatacactat
tctcagaatgacttggttgagtactcaccagtcacagaaaagcatcttacggatggcatgacagtaagaga
attatgcagtgctgccataaccatgagtgataacactgcggccaacttacttctgacaacgatcggaggac
cgaaggagctaaccgcttttttgcacaacatggggatcatgtaactcgccttgatcgttgggaaccggag
ctgaatgaagccataccaaacgacgagcgtgacaccacgatgcctgcagcaatggcaacaacgttgcgcaa
actattaactggcgaactacttactctagcttcccggcaacaattaatagactggatggaggcggataaag
ttgcaggaccacttctgcgctcggcccttccggctggctggtttattgctgataaatctggagccggtgag
cgtgggtctcgcggtatcattgcagcactggggccagatggtaagccctcccgtatcgtagttatctacac
gacggggagtcaggcaactatggatgaacgaaatagacagatcgctgagataggtgcctcactgattaagc
attggtaactgtcagaccaagtttactcatatatactttagattgatttaaaacttcattttaatttaaa
aggatctaggtgaagatcctttttgataatctcatgaccaaaatcccttaacgtgagttttcgttccactg
agcgtcagaccccgtagaaaagatcaaaggatcttcttgagatcctttttttctgcgcgtaatctgctgct
tgcaaacaaaaaaaccaccgctaccagcggtggtttgtttgccggatcaagagctaccaactctttttccg
aaggtaactggcttcagcagagcgcagataccaaatactgtccttctagtgtagccgtagttaggccacca
cttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctga
acggggggttcgtgcacacagcccagcttggagcgaacgacctacaccgaactgagatacctacagcgtga
gctatgagaaagcgccacgcttcccgaagggagaaaggcggacaggtatccggtaagcggcagggtcggaa
caggagagcgcacgagggagcttccaggggaaacgcctggtatctttatagtcctgtcgggtttcgccac
ctctgacttgagcgtcgatttttgtgatgctcgtcaggggggcggagcctatggaaaaacgccagcaacgc
ggcctttttacggttcctggccttttgctggccttttgctcacatgttctttcctgcgttatcccctgatt
ctgtggataacgtattaccgcctttgagtgagctgataccgctcgccgcagccgaacgaccgagcgcagc
gagtcagtgagcgaggaagcggaagagcgcctgatgcggtattttctccttacgcatctgtgcggtatttc
```

Figure 11 continued

Acaccgcatatggtgcactctcagtacaatctgctctgatgccgcatagttaagccagtatacactccgct
atcgctacgtgactgggtcatggctgcgccccgacacccgccaacacccgctgacgcgccctgacgggctt
gtctgctcccggcatccgcttacagacaagctgtgaccgtctccgggagctgcatgtgtcagaggttttca
ccgtcatcaccgaaacgcgcgaggcag Figure 12: Nucleic acid sequence of yeast expression vector for *E. coli* glucuronidase gene - pRS425-GPD-Ub-GUS (SEQ ID NO: 10)

```
gacgaaagggcctcgtgatacgcctattttttataggttaatgtcatgataataatggtttcttagtatgat
ccaatatcaaaggaaatgatagcattgaaggatgagactaatccaattgaggagtggcagcatatagaaca
gctaaagggtagtgctgaaggaagcatacgatacccgcatggaatgggataatatcacaggaggtactag
actacctttcatcctacataaatagacgcatataagtacgcatttaagcataaacacgcactatgccgttc
ttctcatgtatatatatatacaggcaacacgcagatataggtgcgacgtgaacagtgagctgtatgtgcgc
agctcgcgttgcattttcggaagcgctcgttttcggaaacgctttgaagttcctattccgaagttcctatt
ctctagaaagtataggaacttcagagcgcttttgaaaaccaaaagcgctctgaagacgcactttcaaaaaa
ccaaaaacgcaccggactgtaacgagctactaaaatattgcgaataccgcttccacaaacattgctcaaaa
gtatctctttgctatatatctctgtgctatatccctatataacctacccatccacctttcgctccttgaac
ttgcatctaaactcgacctctacatttttatgtttatctctagtattactctttagacaaaaaaattgta
gtaagaactattcatagagtgaatcgaaaacaatacgaaaatgtaaacatttcctatacgtagtatataga
gacaaaatagaagaaaccgttcataattttctgaccaatgaagaatcatcaacgctatcactttctgttca
caaagtatgcgcaatccacatcggtatagaatataatcggggatgcctttatcttgaaaaaatgcacccgc
agcttcgctagtaatcagtaaacgcgggaagtggagtcaggcttttttttatggaagagaaaatagacacca
aagtagccttcttctaaccttaacggacctacagtgcaaaaagttatcaagagactgcattatagagcgca
caaaggagaaaaaaagtaatctaagatgctttgttagaaaaatagcgctctcgggatgcattttgtagaa
caaaaaagaagtatagattctttgttggtaaaatagcgctctcgcgttgcatttctgttctgtaaaaatgc
agctcagattctttgtttgaaaaattagcgctctcgcgttgcattttttgttttacaaaaatgaagcacaga
ttcttcgttggtaaaatagcgctttcgcgttgcatttctgttctgtaaaaatgcagctcagattctttgtt
tgaaaaattagcgctctcgcgttgcattttttgttctacaaaatgaagcacagatgcttcgttcaggtggca
cttttcggggaaatgtgcgcggaaccccctatttgtttattttttctaaatacattcaaatatgtatccgctc
atgagacaataaccctgataaatgcttcaataatattgaaaaaggaagagtatgagtattcaacatttccg
tgtcgcccttattccctttttttgcggcattttgccttcctgtttttgctcacccagaaacgctggtgaaag
taaaagatgctgaagatcagttgggtgcacgagtgggttacatcgaactggatctcaacagcggtaagatc
cttgagagttttcgccccgaagaacgttttccaatgatgagcacttttaaagttctgctatgtggcgcggt
attatcccgtattgacgccgggcaagagcaactcggtcgccgcatacactattctcagaatgacttggttg
agtactcaccagtcacagaaaagcatcttacggatggcatgacagtaagagaattatgcagtgctgccata
accatgagtgataacactgcggccaacttacttctgacaacgatcggaggaccgaaggagctaaccgcttt
tttgcacaacatgggggatcatgtaactcgccttgatcgttgggaaccggagctgaatgaagccataccaa
acgacgagcgtgacaccacgatgcctgtagcaatggcaacaacgttgcgcaaactattaactggcgaacta
cttactctagcttcccggcaacaattaatagactggatggaggcggataaagttgcaggaccacttctgcg
ctcggcccttccggctggtttattgctgataaatctggagccggtgagcgtgggtctcgcggtatca
ttgcagcactggggccagatggtaagccctcccgtatcgtagttatctacacgacggggagtcaggcaact
atggatgaacgaaatagacagatcgctgagataggtgcctcactgattaagcattggtaactgtcagacca
agtttactcatatatactttagattgatttaaaacttcattttttaatttaaaaggatctaggtgaagatcc
tttttgataatctcatgaccaaaatcccttaacgtgagttttcgttccactgagcgtcagacccgtagaa
aagatcaaaggatcttcttgagatccttttttctgcgcgtaatctgctgcttgcaaacaaaaaaaccacc
gctaccagcggtggtttgtttgccggatcaagagctaccaactctttttccgaaggtaactggcttcagca
gagcgcagataccaaatactgtccttctagtgtagccgtagttaggccaccacttcaagaactctgtagca
ccgcctacatacctcgctctgctaatcctgttaccagtggctgctgccagtggcgataagtcgtgtcttac
cgggttggactcaagacgatagttaccggataaggcgcagcggtcgggctgaacggggggttcgtgcacac
agcccagcttggagcgaacgacctacaccgaactgagatacctacagcgtgagctatgagaaagcgccacg
cttcccgaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgat
ttttgtgatgctcgtcagggggggcggagcctatgaaaaacgccagcaacgcggcctttttacggttcctg
gccttttgctggccttttgctcacatgttctttcctgcgttatcccctgattctgtggataaccgtattac
cgcctttgagtgagctgataccgctcgccgcagccgaacgaccgagcgcagcgagtcagtgagcgaggaag
cggaagagcgcccaatacgcaaaccgcctctccccgcgcgttggccgattcattaatgcagctggcacgac
aggtttcccgactggaaagcgggcagtgagcgcaacgcaattaatgtgagttacctcactcattaggcacc
ccaggctttacactttatgcttccggctcctatgttgtgtggaattgtgagcggataacaatttcacacag
gaaacagctatgaccatgattacgccaagcgcgcaattaaccctcactaaagggaacaaaagctggagctc
gtttatcattatcaatactcgccatttcaaagaatacgtaaataattaatagtagtgattttcctaactttt
atttagtcaaaaaattagccttttaattctgctgtaacccgtacatgccaaaatagggggcgggttacaca
gaatatataacactgatggtgcttgggtgaacaggttttattcctggcatccactaaatataatggagcccg
```

Figure 12 continued

```
ctttttaagctggcatccagaaaaaaaaagaatcccagcaccaaaatattgttttcttcaccaaccatcag
ttcataggtccattctcttagcgcaactacagagaacagggcacaaacaggcaaaaaacgggcacaacctc
aatggagtgatgcaacctgcctggagtaaatgatgacacaaggcaattgacccacgcatgtatctatctca
ttttcttacaccttctattaccttctgctctctctgatttggaaaaagctgaaaaaaaaggtttaaaccag
ttccctgaaattattccctacttgactaataagtatataaagacggtaggtattgattgtaattctgtaa
atctatttcttaaacttcttaaattctactttatagttagtcttttttttagttttaaaacaccaagaac
ttagtttcgacggattctagaactagtggatccaagaattcattatgcagatcttcgtcaagacgttaacc
ggtaaaaccataactctagaagttgaatcttccgataccatcgacaacgttaagtcgaaaattcaagacaa
ggaaggcattccacctgatcaacaaagattgatctttgccggtaagcagctcgaggacggtagaacgctgt
ctgattacaacattcagaaggagtcgaccttacatcttgtcttaagactaagaggtggtatggaattcatg
ttacgtcctgtagaaaccccaacccgtgaaatcaaaaaactcgacggcctgtgggcattcagtctggatcg
cgaaaactgtggaattgatcagcgttggtgggaaagcgcgttacaagaaagccgggcaattgctgtgccag
gcagttttaacgatcagttcgccgatgcagatattcgtaattatgcgggcaacgtctggtatcagcgcgaa
gtctttataccgaaaggttgggcaggccagcgtatcgtgctgcgtttcgatgcggtcactcattacggcaa
agtgtgggtcaataatcaggaagtgatggagcatcagggcggctatacgccatttgaagccgatgtcacgc
cgtatgttattgccgggaaaagtgtacgtatcaccgtttgtgtgaacaacgaactgaactggcagactatc
ccgccgggaatggtgattaccgacgaaaacggcaagaaaaagcagtcttacttccatgatttctttaacta
tgccggaatccatcgcagcgtaatgctctacaccacgccgaacacctgggtggacgatatcaccgtggtga
cgcatgtcgcgcaagactgtaaccacgcgtctgttgactggcaggtggtggccaatggtgatgtcagcgtt
gaactgcgtgatgcggatcaacaggtggttgcaactggacaaggcactagcgggactttgcaagtggtgaa
tccgcacctctggcaaccgggtgaaggttatctctatgaactgtgcgtcacagccaaaagccagacagagt
gtgatatctacccgcttcgcgtcggcatccggtcagtggcagtgaagggccaacagttcctgattaaccac
aaaccgttctactttactggctttggtcgtcatgaagatgcggacttacgtggcaaaggattcgataacgt
gctgatggtgcacgaccacgcattaatggactggattggggccaactcctaccgtacctcgcattaccctt
acgctgaagagatgctcgactgggcagatgaacatggcatcgtggtgattgatgaaactgctgctgtcggc
tttaacctctcttttaggcattggtttcgaagcgggcaacaagccgaaagaactgtacagcgaagaggcagt
caacggggaaaactcagcaagcgcacttacaggcgattaaagagctgatagcgcgtgacaaaaaccacccaa
gcgtggtgatgtggagtattgccaacgaaccggataccctgttccgcaagtgcacgggaatatttcgccactg
gcggaagcaacgcgtaaactcgacccgacgcgtccgatcacctgcgtcaatgtaatgttctgcgacgctca
caccgataccatcagcgatctctttgatgtgctgtgcctgaaccgttattacggatggtatgtccaaagcg
gcgatttggaaacggcagagaaggtactggaaaaagaacttctggcctggcaggagaaactgcatcagccg
attatcatcaccgaatacggcgtggatacgttagccgggctgcactcaatgtacaccgacatgtggagtga
agagtatcagtgtgcatggctggatatgtatcaccgcgtctttgatcgcgtcagcgccgtcgtcggtgaac
aggtatggaatttcgccgattttgcgacctcgcaaggcatattgcgcgttggcggtaacaagaaagggatc
ttcactcgcgaccgcaaaccgaagtcggcggcttttctgctgcaaaaacgctggactggcatgaacttcgg
tgaaaaaccgcagcagggaggcaaacaatgagaatcccatcaagcttatcgataccgtcgacctcgagtgc
aaattaaagccttcgagcgtcccaaaaccttctcaagcaaggttttcagtataatgttacatgcgtacacg
cgtctgtacagaaaaaaagaaaaatttgaaatataaataacgttcttaatactaacataactataaaaaa
ataaatagggacctagacttcaggttgtctaactccttccttttcggttagagcggatgtgggggggaggc
gtgaatgtaagcgtgacataactaattacatggtacccaattcgccctatagtgagtcgtattacgcgcgc
tcactggccgtcgttttacaacgtcgtgactgggaaaaccctggcgttacccaacttaatcgccttgcagc
acatccccctttcgccaggggctgcaggaattcgatatcaagcttatcgataccgtcgacctcgagggggg
gcccggtacccaattcgccctatagtgagtcgtattacgcgcgctcactggccgtcgttttacaacgtcgt
gactgggaaaaccctggcgttacccaacttaatcgccttgcagcacatccccctttcgccagctggcgtaa
tagcgaagaggcccgcaccgatcgcccttcccaacagttgcgcagcctgaatggcgaatggcgcgacgcgc
cctgtagcggcgcattaagcgcggcgggtgtggtggttacgcgcagcgtgaccgctacacttgccagcgcc
ctagcgcccgctcctttcgctttcttcccttcctttctcgccacgttcgccggctttccccgtcaagctct
aaatcgggggctcccttagggttccgatttagtgctttacggcacctcgaccccaaaaaacttgattagg
gtgatggttcacgtagtgggccatcgccctgatagacggtttttcgccctttgacgttggagtccacgttc
tttaatagtggactcttgttccaaactggaacaacactcaaccctatctcggtctattcttttgatttata
agggattttgccgatttcggcctattggttaaaaaatgagctgatttaacaaaaatttaacgcgaatttta
acaaaatattaacgtttacaatttcctgatgcggtattttctccttacgcatctgtgcggtatttcacacc
gcatatcgacggtcgaggagaacttctagtatatccacatacctaatattattgccttattaaaaatggaa
tcccaacaattacatcaaaatccacattctcttcaaaatcaattgtcctgtacttccttgttcatgtgtgt
tcaaaaacgttatatttataggataattatactctatttctcaacaagtaattggttgtttggccgagcgg
```

Figure 12 continued

```
tctaaggcgcctgattcaagaaatatcttgaccgcagttaactgtgggaatactcaggtatcgtaagatgc
aagagttcgaatctcttagcaaccattatttttttcctcaacataacgagaacacacaggggcgctatcgc
acagaatcaaattcgatgactggaaattttttgttaatttcagaggtcgcctgacgcatataccttttca
actgaaaaattgggagaaaaaggaaaggtgagaggccggaaccggcttttcatatagaatagagaagcgtt
catgactaaatgcttgcatcacaatacttgaagttgacaatattatttaaggacctattgttttttccaat
aggtggttagcaatcgtcttactttctaacttttcttaccttttacatttcagcaatatatatatatattt
caaggatataccattctaatgtctgcccctatgtctgcccctaagaagatcgtcgttttgccaggtgacca
cgttggtcaagaaatcacagccgaagccattaaggttcttaaagctatttctgatgttcgttccaatgtca
agttcgatttcgaaaatcatttaattggtggtgctgctatcgatgctacaggtgtcccacttccagatgag
gcgctggaagcctccaagaaggttgatgccgttttgttaggtgctgtggctggtcctaaatggggtaccgg
tagtgttagacctgaacaaggtttactaaaaatccgtaaagaacttcaattgtacgccaacttaagaccat
gtaactttgcatccgactctcttttagacttatctccaatcaagccacaatttgctaaaggtactgacttc
gttgttgtcagagaattagtgggaggtatttactttggtaagagaaaggaagacgatggtgatggtgtcgc
ttgggatagtgaacaatacaccgttccagaagtgcaaagaatcacaagaatggccgctttcatggccctac
aacatgagccaccattgcctatttggtccttggataaagctaatcttttggcctcttcaagattatggaga
aaaactgtggaggaaaccatcaagaacgaattccctacattgaaggttcaacatcaattgattgattctgc
cgccatgatcctagttaagaacccaacccacctaaatggtattataatcaccagcaacatgtttggtgata
tcatctccgatgaagcctccgttatcccaggttccttgggtttgttgccatctgcgtccttggcctctttg
ccagacaagaacaccgcatttggtttgtacgaaccatgccacggttctgctccagatttgccaaagaataa
ggttgaccctatcgccactatcttgtctgctgcaatgatgttgaaattgtcattgaacttgcctgaagaag
gtaaggccattgaagatgcagttaaaaaggttttggatgcaggtatcagaactggtgatttaggtggttcc
aacagtaccaccgaagtcggtgatgctgtcgccgaagaagttaagaaaatccttgcttaaaaagattctct
tttttatgatatttgtacataaactttataaatgaaattcataatagaaacgacacgaaattacaaaatg
gaatatgttcatagggtagacgaaactatatacgcaatctacatacatttatcaagaaggagaaaaaggag
gatagtaaaggaatacaggtaagcaaattgatactaatggctcaacgtgataaggaaaaagaattgcactt
taacattaatattgacaaggaggagggcaccacacaaaaagttaggtgtaacagaaaatcatgaaactacg
attcctaatttgatattggaggattttctctaaaaaaaaaaaaatacaacaaataaaaaacactcaatgac
ctgaccatttgatggagtttaagtcaataccttcttgaagcatttcccataatggtgaaagttccctcaag
aattttactctgtcagaaacggccttacgacgtagtcgatatggtgcactctcagtacaatctgctctgat
gccgcatagttaagccagccccgacacccgccaacacccgctgacgcgccctgacgggcttgtctgctccc
ggcatccgcttacagacaagctgtgaccgtctccgggagctgcatgtgtcagaggttttcaccgtcatcac
cgaaacgcgcga
```

COMPOSITIONS AND METHODS FOR GENDER SORTING

This application claims priority to U.S. Provisional Application No. 60/286,010, filed Apr. 23, 2001, the entire disclosure of which is incorporated by reference herein.

FIELD OF THE INVENTION

The present invention relates to a novel method for detection of target molecules, such as hormones, using a yeast-based transactivation system. More particularly, the invention relates to methods for accurate and efficient gender sorting in mammalian and avian species.

BACKGROUND OF THE INVENTION

Various publications and patent documents are referenced in this application to describe the state of the art to which the invention pertains. Complete citations for these references are found at the end of the specification. Each of these publications or patents is incorporated by reference herein.

Sex separation of chicks at hatch is an important aspect of the poultry industry. The US poultry industry produces 8.9 billion broilers, 360 million broiler breeders, 360 million turkeys and 1.6 billion layers annually. These annual production numbers equate to roughly 160 million birds hatched each day which need to be sexed. Varied segments of the poultry industry must sex segregate offspring for different reasons. All turkeys are sex segregated due to the large differences in the growth rate, market age, management practices and nutritional requirements between male and female birds. In the layer or table egg industry, chicks must be sexed at hatch as only the females, or birds which lay eggs, are kept while all male chicks are discarded. The broiler breeder and turkey breeder industries produce both male and female lines that are eventually crossed to produce a hybrid commercial bird. The males or off-sex chicks produced from the female lines are discarded while the female chicks or off-sex chicks from the male lines are discarded. Disposal of unwanted chicks creates animal welfare and waste disposal issues for the industry. The meat type chicken or broiler industry prefer to sex segregate males from females to gain feed efficiency, improve uniformity at the processing plant and reduce production costs. The broiler industry often refrains from sex separate rearing due to the high costs of sexing and the need for trained sexers. A higher percentage of the broiler industry would sex segregate if a rapid, inexpensive, automated method were available.

Current sexing methods used in the poultry industry involve manual procedures that require highly trained professionals with specialized skills. Sexing methods involve either the Japanese method of vent sexing or feather sexing of chicks that carry a slow feathering gene (1, 2, 3). The manual sexing methods have several drawbacks. These include: 1) scheduling of manual labor; 2) increased processing time before chicks can be placed in the field with access to food and water; and 3) stress and damage to the chicks or poults. Manual sexing remains one of the few manual processing steps practiced in the highly automated poultry industry.

The Japanese or vent sexing method originated in the 1920's when the Japanese discovered that within the first or second fold of a chick's vent there are distinctive characteristics such as spots, lines and folds that reveal its sex (4, 5). Vent sexing is considered an art and generally practiced only by Asian individuals with excellent manual dexterity and Zen-like concentration (6). Vent sexers attend school for six months and then undergo a trainee program for two to five years until they are considered a qualified sexer based on speed and accuracy. Qualified sexers can vent sex 2,000 chicks per hour at 98% accuracy but only 5 to 10% of individuals attending vent sexing school attain qualified sexer status (6). The rapid rate at which a vent sexer must pick up, sex and sort baby chicks can result in a 1.4 to 1.8% increase in cull rate and 0.5 to 1.0% increase in early chick mortality due to chick damage during handling (7). Vent sexers are contract workers who travel from hatchery to hatchery working long tedious hours. Travel of these contract workers from hatchery to hatchery poses a bio-security threat for the poultry industry.

Feather sexing of chickens inbred for the K gene for slow feathering is the other commonly used method for sex segregation at hatch (3). Day-old chicks carrying the K gene can be sex segregated by examining the relative length of the primary and covert feathers of the wing, with the females carrying genes for fast feathering and the males carrying genes for slow feathering. Feather sexing is less expensive than vent sexing and does not require as skilled a labor force. Feather sexing is not applicable to turkeys, the majority of broiler breeds, some layer breeds, and also carries disadvantages. The k gene for slow feathering is closely linked to an endogenous virus (8), which can cause immunological tolerance to lymphoid leukosis (9) and is therefore a disadvantage in breeding stock. It is noteworthy that slow feathering males usually do not feather well in the brooder house especially during hot weather which often results in slower growth and increased cannibalism and that females carrying the K gene exhibit reduced egg production. Some poultry breeds exhibit sex specific color differences in feathers, however these breeds are not as commercially viable as other breeds. Color sexing can result in a higher rate of sexing mistakes than feather sexing.

Methods to sex segregate eggs before hatching have been previously attempted without success. A sex-linked gene, $S^{al}$ for imperfect albinism was reported by Hutt and Cole (10) to have the potential to sex chicks at one day of age on the basis of eye color. The albino female chicks have pink eyes while the normal males have black eyes. The difference in eye color can also be used to accurately sex segregate embryos by candling the eggs on Day 10 of incubation. Candling or light illumination of the intact egg reveals the dark eye of the male chicken embryo but not the pink eye of the albino female. Use of the $S^{al}$ gene to sex segregate poultry was not pursued as the gene carries deleterious effects in turkeys and negative production effects in chickens.

Development of a quick, accurate, inexpensive automated method to sex segregate eggs before hatching would significantly increase profitability of the global broiler industry. Automated sexing gives rise to several benefits. These include 1) better feed and processing efficiencies; 2) reduced incubation space requirements; 3) greater selection of breeds without constraints of selection for a slow feathering gene; 4) reduced liability and reliability concerns associated with eliminating manual labor; 5) speedier hatchery processing; and 6) reduced animal welfare concerns associated with discarding male chicks in the layer egg industry.

In light of all the foregoing, the development of a quick, inexpensive, automated method to sex segregate eggs before hatching is highly desirable.

SUMMARY OF THE INVENTION

The present invention provides a method and kit for detecting target molecules in a sample. In a preferred embodiment, methods and kits for determining the sex of avian species while in the egg are disclosed. The cell-based sensor has additional applications in detection of glucuronidated steroid hormones, metabolites and xenobiotics. The ultra sensitive method of the invention may also be used to advantage to gender sort other animal species, and to assess patient populations for their susceptibility to drugs and predisposition to disease.

In an exemplary embodiment of the invention, a biological sample containing a sex-indicating hormone is isolated from the egg. Genetically engineered host cells comprising a sex hormone-dependent transactivation system are then contacted with the biological fluid. The engineered cells respond to the level of sex hormone by activating a reporter gene. Female eggs, which contain a significant amount of 17 β estradiol, a hormone that is absent from male embryos, give a positive response in cell-based sensor assays of the invention and are sorted as females.

In another embodiment of the invention, a ligand dependent transactivation system for gender-sorting in a test animal is provided, wherein the system comprises a) a first DNA construct comprising a nucleic acid molecule encoding a receptor having specific binding affinity for said ligand operably linked to a promoter; b) a second DNA construct comprising a promoter containing a plurality of ligand specific response elements, said promoter being operably linked to a reporter gene; c) a third DNA construct comprising a nucleic acid sequence encoding an enzyme for cleaving a naturally occurring biological conjugate, said biological conjugate comprising said ligand, said nucleic acid sequence encoding said enzyme being operably linked to a promoter sequence; and d) a host cell comprising said first, second and third DNA constructs, expression of said reporter gene in said host cell being dependent upon cleavage of said ligand from a biological conjugate present in a biological sample isolated from said test animal, reporter gene expression being indicative of the presence of a ligand which indicates the sex of said test animal. In another embodiment of the invention, the first DNA construct encodes a receptor selected from the group of sex related nuclear receptors consisting of estrogen receptor alpha, estrogen receptor beta, androgen receptor, progesterone receptor, glucocorticoid receptor, adrenocorticoid receptor, thyroid hormone receptor alpha and beta, retinoic acid receptor alpha, beta and gamma, retinoic acid x receptor alpha, beta and gamma, peroxysome proliferator activating receptor alpha, delta and gamma, vitamin D receptor, dioxin receptor, and liver X receptor.

In yet another embodiment, a method for detecting the presence of sex determinative ligands which transactivate nuclear receptors in a ligand-dependent manner in a biological sample are provided, wherein the method comprises: a) providing a host cell containing a first DNA construct having a nucleic acid molecule encoding a receptor having binding affinity for a sex determinative ligand operably linked to a first promoter; a second DNA construct comprising a second promoter containing a plurality of sex determinative ligand response elements, said second promoter being operably linked to a reporter gene and a third DNA construct comprising a nucleic acid sequence encoding an enzyme for cleaving a naturally occurring biological conjugate, said biological conjugate comprising said sex determinative ligand, said nucleic acid sequence encoding said enzyme being operably linked to a third promoter sequence; b) contacting said host cell with a biological sample suspected of containing said sex determinative ligand; and c) assessing levels of expression of said reporter gene in said host cell, said expression being dependent upon cleavage of said sex determinative ligand from a biological conjugate if present, in said biological sample. In a particular embodiment, the first DNA construct encodes a receptor selected from estrogen receptor alpha, estrogen receptor beta, androgen receptor, progesterone receptor, glucocorticoid receptor, adrenocorticoid receptor, thyroid hormone receptor alpha and beta, retinoic acid receptor alpha, beta and gamma, retinoic acid X receptor alpha, beta and gamma, peroxysome proliferator activating receptor alpha, delta and gamma, vitamin D receptor, dioxin receptor, and liver X receptor isolated from different organisms.

BRIEF DESCRIPTION OF THE DRAWINGS

FIGS. 2A–2C are schematic diagrams of the estrogen-dependent transactivation system of the present invention.

FIGS. 6A and 6B show a pair of graphs showing that the gender sorting system of the invention efficiently sorts male and female turkeys as well as layer chickens.

FIG. 9 shows the nucleic acid sequence of the CYC1-based estrogen inducible reporter YRpE2 (SEQ ID NO: 7). It comprises the *E. coli* replication origin and bacterial selection marker for Ampicillin resistance, the yeast 2 micron *S. cerevisiae* replicative origin, yeast selection marker URA3, and the *E. coli* beta-galactosidase gene which is operably linked to the CYC1 core promoter. The 2× estrogen response element (2×ERE) unit is operably linked to the CYC1 promoter in the upstream region.

FIG. 10 shows the nucleic acid sequence of the SSA4-based estrogen inducible reporter YRpE2SSA4-lacZ (SEQ ID NO: 8). It comprises the *E. coli* replication origin and bacterial selection marker for Ampicillin resistance, the yeast 2 micron *S. cerevisiae* replicative origin, the yeast selection marker URA3, and the *E. coli* beta-galactosidase gene which is operably linked to the SSA4 core promoter. The 2×ERE unit is operably linked to the SSA4 promoter in the upstream region.

FIG. 11 shows the nucleic acid sequence of the yeast expression vector for human estrogen receptor alpha—YEpE12-ERα (SEQ ID NO: 9). It comprises the *E. coli* replication origin and bacterial selection marker for Ampicillin resistance, the yeast 2 micron *S. cerevisiae* replicative origin, yeast selection marker TRP1, and a human estrogen receptor fused in frame with human ubiquitin which is operably linked to the yeast CUP1 promoter.

FIG. 12 shows the nucleic acid sequence of the yeast expression vector for the *E. coli* glucuronidase gene—pRS425-GPD-Ub-GUS (SEQ ID NO: 10). It comprises the *E. coli* replication origin and bacterial selection marker for Ampicillin resistance, the yeast 2 micron *S. cerevisiae* replicative origin, the yeast selection marker LEU2, and the *E. coli* beta-glucuronidase gene which is fused in frame with human ubiquitin which is operably linked to the yeast GPD promoter.

DETAILED DESCRIPTION OF THE INVENTION

Figure 1:
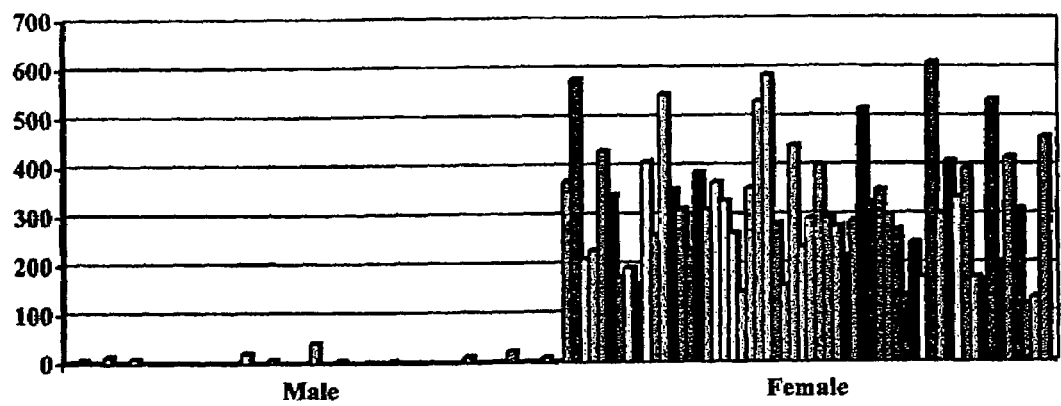
FIG. 1 is a graph showing the difference of estradiol levels in pg/ml in the allantoic fluid of male and female broiler 17-day old embryos.

In accordance with the present invention, compositions, methods and kits are provided for the accurate and efficient detection of biological target molecules. A yeast-based biosensor is disclosed to identify and characterize target molecules isolated from biological samples. In a preferred aspect of the invention, a gender sorting method is provided which enables pre-hatch sorting of female embryos from male embryos.

I. Definitions

The following definitions are provided to facilitate an understanding of the present invention.

As used herein, a "reporter gene" encodes a molecule whose expression may be assayed; such genes include, without limitation, β-galactosidase (LacZ), alkaline phosphatase, amino acid biosynthetic genes, e.g., the yeast LEU2, HIS3, or LYS2 genes, nucleic acid biosynthetic genes, e.g. URA3 or ADE2 genes, the chloramphenicol acetyltransferase (CAT) gene, green fluorescent protein (GFP), red fluorescent protein such as DsRd or any surface antigen gene for which specific antibodies are available. Additionally "reporter gene" may encompass any gene of interest whose expression may be detected. The term "reporters" may be used broadly to include systems where expression is detected based on ligand binding induced alterations in receptor structure. Such alterations in receptor structure may be assessed using a variety of methods well known to those of skill in the art, and include without limitation, assessing degradation, recycling, and molecular association rates of ligand bound receptor based on gain or loss of a detectable label. Such labels may be radioactive, fluorescent or chemiluminescent.

A "promoter" is a DNA sequence located proximal to the start of transcription at the 5' end of an operably linked transcribed sequence. The promoter may contain one or more regulatory elements or modules that act together in coordinating and regulating transcription of the operably linked gene. An inducible promoter is a promoter that responds to the presence of different biochemical stimuli. Such promoters include, but are not limited, to the CUP1 promoter, heat shock promoters, galactose-inducible promoters, glycolytic promoters such as alcohol dehydrogenase (ADH) glyceraldehyde phosphate dehydrogenase (GPD) and the like.

"Operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

"Fusion construct" refers generally to recombinant genes which encode fusion proteins. Such fusion constructs may include operably linked nucleic acids isolated from two different genes.

A "fusion protein" is a hybrid protein, i.e., a protein that has been constructed to contain domains from at least two different proteins. An exemplary fusion protein, as described herein is a hybrid protein which possesses (a) a transcriptional regulatory domain from a transcriptional regulatory protein, or (b) a DNA binding domain from a DNA binding protein linked to a heterologous protein to be assayed for interaction. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain. In other words, the two domains are heterologous to each other.

The transcriptional regulatory domain of the fusion protein may either activate or repress transcription of target genes, depending on the native biological activity of the domain.

The term "fusion protein gene" refers to a DNA sequence that encodes a fusion protein. A fusion protein gene may further provide transcriptional and translational regulatory elements for the transcriptional and translational control thereof.

"Expression" is the process by which the information encoded within a gene is revealed. If the gene encodes a protein, expression involves both transcription of the DNA into mRNA, the processing of mRNA (if necessary) into a mature mRNA product, and translation of the mature mRNA into protein.

A nucleic acid molecule, such as a DNA or gene is said to be "capable of expressing" a polypeptide if the molecule contains the coding sequences for the polypeptide operably linked to expression control sequences which, in the appropriate host environment, facilitate transcription, processing and translation of the encoded genetic information into a protein product.

The phrase "consisting essentially of" when referring to a particular nucleotide or amino acid means a sequence having the properties of a given reference sequence. For example, when used in reference to an amino acid sequence, the phrase includes the sequence per se and molecular modifications that would not affect the basic and novel characteristics of the sequence.

As used herein, a "cloning vector" is any entity that is capable of delivering a nucleic acid sequence into a host cell for cloning purposes. Examples of cloning vectors include plasmids or phage genomes. A plasmid which replicates autonomously in a host cell is especially preferred. Alternatively, a nucleic acid molecule which stably integrates into the host cell's chromosomal DNA and is inherited by daughter cells may be employed. Optionally, such vectors include a number of endonuclease recognition sites to facilitate manipulation of the sequence in a controlled and targeted fashion. Cloning vectors of the invention may also comprise sequences conferring resistance to selection agents, often referred to herein as selectable marker genes. For example, "a marker gene" may be a gene which confers resistance to a specific antibiotic on a host cell.

As used herein, an "expression vector" is a vehicle or vector similar to the cloning vector but is especially designed to provide an environment that facilitates expression of the cloned gene product after transformation into the host. Such vectors contain regulatory elements for expression in prokaryotic and/or eukaryotic hosts as well as sequences conferring selection properties of cells containing the expression vector. Optionally, enhancer elements, termination sequences, tissue-specificity elements, and/or translational initiation and termination sites may be included.

A "host" refers to any organism or cell line that is the recipient of a cloning or expression vector. In preferred embodiments, the host of the invention is a yeast cell or a cultured animal cell such as a mammalian or insect cell. Especially preferred is the yeast host *Saccharomyces cerevisiae*.

A "transformed cell" is any cell into which (or into an ancestor of which) exogenous DNA has been introduced by means of recombinant DNA techniques.

"Ligands" are small compounds such as chemical molecules or small peptides that are able to bind to the target proteins (for example, the receptor heterodimers described herein). By interaction with a target protein, ligands change conformation of the protein and thereafter activate or inactivate the protein.

"Response elements" are specific DNA sequences located in promoters of inducible genes; such inducers may include chemicals, hormones, metals such as zinc, cadmium or copper, heat shock and transcription factors. Nuclear receptors in the form of homodimers, heterodimers or monomers bind specifically to DNA response elements to activate or repress transcription of the targeted genes in the presence or the absence of ligands for the nuclear receptors.

II. Methods and Compositions for Gender Sorting

Cost effective methods for sex segregation of avian eggs require a sex specific target which can be detected at 98% accuracy, at a rate of 10,000 to 20,000 eggs per hour, and can be offered to the poultry industry at a cost of less than 5 cents per egg sexed. Potential sex specific targets include: 1) differences in physiologic parameters such as heart; 11, 12); 2) presence of the W specific chromosome in females (13, 14, 15); 3) presence of anatomical differences such as gonads; and 4) chemical differences which may be present in the blood or extra-embryonic fluids of the avian embryo.

Methods that may be potentially useful for gender sorting are set forth in Table 1.

TABLE 1

Comparison of LifeSensors Gender Sorting Sensors with Other Technologies

| Technology | Speed | Sensitivity | Cost | Background Interference | Ease of Automation |
|---|---|---|---|---|---|
| LifeSensor | yes | Yes | yes | no | yes |
| Biosensors | no | No | yes | no | yes |
| Electronic Nose | yes | No | yes | yes | yes |
| NIR Spectrometry | yes | No | yes | yes | yes |
| Ion Mobility Spectroscopy | yes | No | yes | yes | yes |
| Fluorescent Polarization | yes | Yes | yes | yes | no |
| Antibody Based Technologies | yes | Yes | no | no | yes |
| Photoacoustics | yes | No | yes | no | yes |
| Imprint Polymers | yes | No | yes | no | yes |
| Mass Spectrometry | no | Yes | no | no | no |
| Laser Induced Fluorescent Spectrometry | yes | No | yes | yes | yes |

Numerous analytical techniques to detect estradiol or other sex specific compounds were evaluated. As can be seen from Table 1 only the LifeSensors technology described herein meets the desired criteria of cost, sensitivity, speed, accuracy, safety and ease of application to a commercial hatchery environment.

Sex specific chemicals present in blood or extra-embryonic fluids provide optimal analytical targets for meeting the above criteria. Suitable chemical based targets are male or female-specific hormones. It is well established that male and female embryos exhibit significant differences in hormone levels in sera and in male or female gonadal tissue culture systems (16, 17, 18). The data provided in these studies suggested that differences in the estrogen levels of male and female embryos would be greater than differences in the testosterone levels.

Differences in sex hormone levels are also evident in the allantoic fluid. In 1983, Gill and coworkers reported the presence of estrone sulfate, estradiol-17β sulfate, estradiol-17α sulfate, estrone glucuronide, estradiol-17α glucuronide and estradiol-β glucuronide in pg/ml quantities in the allantoic fluid of female embryos but not in the allantoic fluid of male embryos. No estrogens were present in the amniotic fluid of either sex (19). The amniotic fluid is primarily maternally derived and acts as a nutrient source and a cushion from mechanical and thermal insults.

The present invention is directed to methods for detecting the presence of sex specific estrogen levels in the chorioallantoic fluid of avian eggs using a yeast-based genetic system. The use of chorioallantoic fluid is preferred over the use of either blood or amniotic fluid as the allantoic fluid is proximal to the outside of the egg and is not in direct contact with the fluid surrounding the embryo. The allantois is separated from the eggshell only by the inner and outer shell membranes and the chorioallantoic membrane. Although the allantoic sac containing the allantoic fluid encompasses the entire periphery of the embryonated egg, the allantoic fluid accumulates at the top and upper sides of the egg directly underneath the membranes overlying the air space. The accumulation at the top of the egg is due to gravity and displacement by the dense embryo and yolk sac.

The allantoic fluid is recognized as an excretory medium for the nitrogenous metabolites of the embryo (20). The allantoic fluid begins to form around Day 5 of incubation. It attains a maximum volume of 6.1 mls on Day 13 of incubation, wanes in volume as incubation continues due to moisture loss and fluid resorption but is still present in significant volumes (1 to 2 mls) on Day 18 of incubation (20). The accumulation of solids in the allantoic fluid is continuous throughout the developmental period. The presence of significant amounts of allantoic fluid, which is readily accessible, between Days 13 and 18 of incubation render the allantois a feasible target for detection of a sex specific chemical.

It should also be noted that the estrogen present in allantoic fluids is not an active form, as it exists in the form of conjugates with either glucuronides or sulfates. While immunoassay is available for detecting conjugated estrogen levels, the method is not extremely sensitive nor, more importantly, cost-effective.

The presence of estrogens in the allantoic fluid of Day 17 embryos has been further investigated in efforts to assess the reliability of estrogens as a sex specific chemical marker. The estradiol levels in the allantoic fluid of male and female Day 17 broiler chicken embryos were measured using a commercially available RIA kit (Diagnostic Products, Los Angeles, Calif.).

The estradiol level in the allantoic fluid of male embryos was either non-detectable or less than 42 pg/ml. The estradiol level in the allantoic fluid of female embryos was between 184 and 830 pg/ml, at least four times higher than the levels detected in male embryos. These data indicate that estrogen conjugates can be used to segregate female from male embryos.

The presence of testosterone in the allantoic fluid has also been investigated as androgens may interfere with analysis of estradiol due to similarity in molecular structures. Studies have shown that testosterone levels were undetectable in the allantoic fluid of Day 17 broiler embryos using a commercial RIA kit (Diagnostic Products, Los Angeles, Calif.).

Studies were also conducted to assess the optimal period of embryonic incubation for estradiol detection using the analytical methods described herein. Estradiol was initially detected by our methods on Day 13 of incubation and coincided with reports by Gill and coworkers (19). As shown herein, estrogen levels peaked at Day 17 of incubation.

In accordance with the present invention, a yeast-based genetic system and methods of use, thereof are provided to facilitate gender sorting in poultry. The methods provided herein enable the rapid and efficient sorting of eggs based on the presence of sex hormones in allantoic fluid.

II. Preparation of Nucleic Acid Molecules Encoding the Proteins of the Invention and Uses Thereof in Assay Methods and Kits A. Nucleic Acid Molecules Nucleic acid molecules encoding the expression vectors of the invention may be prepared by two general methods: (1) They may be synthesized from appropriate chemical starting materials, or (2) they may be isolated from biological sources. Both methods utilize protocols well known in the art.

The availability of nucleotide sequence information, for the estrogen receptor, as well as for secretory signals from alpha-mating factor or yeast SUC2 gene facilitates synthesis of DNA constructs containing such sequences. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule encoding a construct of the present invention, must be synthesized in stages due to the size limitations inherent in current oligonucleotide synthetic methods. Thus, for example, a 3 kilobase double-stranded molecule may be synthesized as several smaller segments of appropriate complementarity. Complementary segments thus produced may be ligated such that each segment possesses appropriate cohesive termini for attachment of an adjacent segment. Adjacent segments may be ligated by annealing cohesive termini in the presence of DNA ligase to construct the entire 3 kilobase double-stranded molecule. A synthetic DNA molecule so constructed may then be cloned and amplified in an appropriate vector. In alternative embodiments of the invention, the human estrogen receptor α (referred to herein as "estrogen receptor"), reporter gene and *E. coli* gene for expression of glucuronidase can be substituted with similar genes from other biological sources. Suitable candidate genes for such substitution include, without limitation, estrogen receptor β which also has high affinity for the hormone and does mediate transactivation in eukaryotic cells in response to 17β estradiol. In addition, one can replace human estrogen receptor with a homologous receptor molecule from mouse or other higher eukaryotic estrogen receptors. The *E. coli* beta-glucuronidase gene can be replaced with a snail gene that expresses glucuronidase, or any other glucuronidases that can cleave the 17β estradiol glucuronides. For example, the *Lactobacillus gasseri* gusA gene with a pH optima of 5 also provides a suitable candidate GUS gene (Russell and Klaenhammer, 2001). Since the pH of extracellular yeast media is acidic, this enzyme is well suited for use in the gender sorting sensor as an extra step to adjust the pH can be omitted.

Estrogen conjugates are cleaved by β-glucuronidases to produce 17β estradiol. The pure estrogen molecule binds to the resident estrogen receptor to transactivate a reporter gene. In accordance with the present invention methods for assessing estrogen levels in allantoic, or amniotic fluid or any other biological or chemical estrogens and their ability to transactivate the reporter genes described herein are provided. The constructs containing the estrogen receptor encoding sequences described herein may be substituted either with mutated (modified or altered receptor) or a receptor from another species.

Similarly, the glucuronidase enzyme of the invention may be derived from different species. The *E. coli* β-glucuronidase has been used in the studies described herein. However, β-glucuronidases from rat or human may have altered properties that may make them more robust and efficient than the *E. coli* glucuronidase. The use of glucuronidase from Lactobacillus gusA (GenBank Accession number: AF305888) is also encompassed within the scope of the present invention. In addition to estrogen glucuronides, biological fluids may contain other forms of modified estrogens such as estrogen sulfates. Under these circumstances appropriate de-conjugating enzymes such as sulfatases can be employed to convert the estrogen conjugate into 17 β estradiol. Thus, in this situation, glucuronidases can be replaced with sulfatases.

Nucleic acid sequences encoding the components of the expression plasmids of the invention may be isolated from appropriate biological sources using methods known in the art. For example, RNA isolated from a mammalian or insect cell may be used as a suitable starting material for the generation of cDNA molecules encoding the different receptor proteins.

In accordance with the present invention, nucleic acids having the appropriate level of sequence homology with the protein coding region of the DNA molecules of the present invention may be identified by using hybridization and washing conditions of appropriate stringency. For example, hybridizations may be performed, using a hybridization solution comprising, for example, 5×SSC, 5× Denhardt's reagent, 1.0% SDS, 100 mg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is as follows (21):

$$T_m = 81.5° C. + 16.6 \text{ Log } [Na+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the sequences of the present invention.

Nucleic acids encoding the fusion proteins of the invention may be maintained as DNA in any convenient cloning vector. In one embodiment, clones are maintained in plasmid cloning/expression vectors, such as pRS plasmids series (27), or YEpE12 derivative plasmids (26, 28). pBluescript plasmids (Stratagene, La Jolla, Calif.) or recombinant baculovirus transfer vector plasmids, such as pFastBac vectors (Gibco-BRL, Gaithersburg, Md.) that are propagated in insect and *E. coli* host cells, may also be employed.

The nucleic acids of the invention may also be used as starting materials for the generation of sequence variants or truncation mutants of the nucleic acids of the invention using any number of synthetic and molecular biologic procedures well known in the art including, but not limited to, truncation at available restriction sites and site-directed mutagenesis techniques. Particular mutations may give rise to receptor proteins with altered characteristics such as increased or decreased ligand binding activity.

B. Fusion Proteins

In one embodiment of the invention, the estrogen receptors of the invention are expressed in yeast as ubiquitin fusion proteins. Ubiquitin fusion enhances but is not necessary for protein expression in yeast. After translation of recombinant proteins, the 76 amino acids of ubiquitin sequence in the N-terminus are cleaved by the host ubiquitin pathway and native proteins are released. It is widely known that the presence of the ubiquitin sequence improves the expression of proteins of interest in yeast and *E. coli* (26, 29).

Attachment of SUMO, a 101 amino acid protein, to the N-terminus of GUS also enhances the expression and extracellular secretion of the protein into the media. SUMO is a homologue of ubiquitin that is conjugated to other proteins via the epsilon amino groups of lysine (Yeh et al 2000, Mahajan et al 1997). The Smt3 gene in yeast encodes for SUMO (Li and Hochstrasser 2000). Similar to the case with ubiquitin conjugation and de-conjugation to other proteins, SUMO can be cleaved from the fusion protein by SUMO specific proteases (Li and Hochstrasser 2000, Kim et al 2000). Therefore, SUMO-fusion proteins can also be expressed and cleaved in eukaryotic and prokaryotic cells. Since SUMO protein or SUMO enzymes are absent in prokaryotes, sumolated proteins expressed in *E. coli* are not cleaved in the absence of SUMO specific hydrolase or protease. In eukaryotic cells, such as yeast, a SUMO-GUS fusion is cleaved by cellular SUMO specific hydrolases (Suzuki et al 1999, Kim et al 2000, Li and Hochstrasser 2000).

Figure 5:
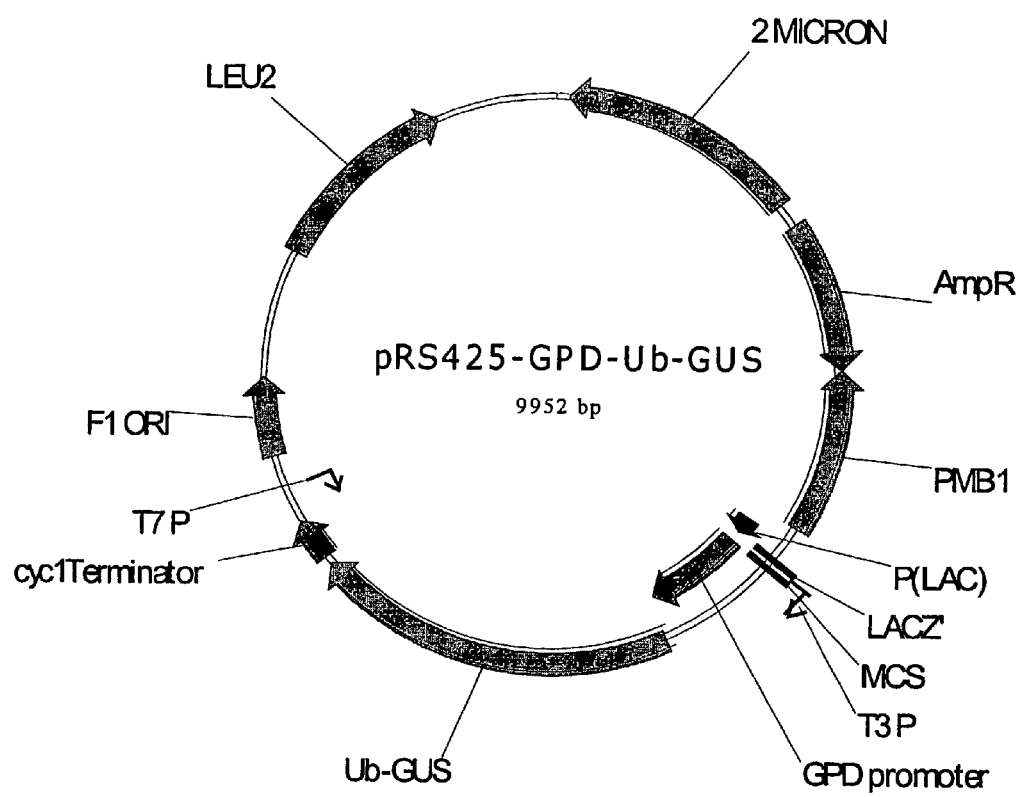
FIG. 5 (pRS425-GPD-Ub-GUS) shows the yeast expression plasmids for expressing the E. coli GUS (beta-glucuronidase gene; Jefferson et al, 1986). The N-terminal coding sequence of the GUS gene is fused in frame with the C-terminal of the human ubiquitin gene. The recombinant protein is under GPD promoter. LEU2 is the leucine (LEU2) selectable marker and 2 μm facilitates replication in yeast.

The glucuronidase enzymes of the invention are expressed in yeast after attachment of secretory signals and as ubiquitin fusion protein(s) as well. The attachment of the secretory signals in the N-terminal region of glucuronidase or ubiquitin facilitates extracellular secretion of the enzyme following translation. A wide variety of secretion signal sequences are available, including but not limited to, the N-terminus of alpha factor or SUC2. FIG. 5 shows an exemplary plasmid that was robust in secreting *E. coli* GUS in yeast. Similar plasmids may be generated containing glucuronidase genes from other species, under different secretory signals using different promoters and different hosts to produce active GUS that can cleave the estrogen-glucuronides conjugates.

In a preferred embodiment of the invention, nucleic acid sequences encoding the N-terminus of glucuronidase were operably linked at the C-terminus to a ubiquitin gene. The presence of the ubiquitin moiety at the N-terminus of glucuronidase facilitated and enhanced secretion of the enzyme. See Table 8.

In an alternative embodiment of the invention, the fusion proteins may be prepared using in vitro expression methods known in the art. In this fashion, glucuronidase may be supplied exogenously to the transactivating system of the invention. For example, a cDNA or gene may be cloned into an appropriate in vitro transcription vector, such as pSP64 or pSP65 for in vitro RNA synthesis, followed by cell-free translation of the RNA in a suitable cell-free translation system, such as extracts of wheat germ, rabbit reticulocytes or HeLa cells. In vitro transcription and translation systems are commercially available (e.g., Promega Biotech, Madison, Wis.; Gibco-BRL, Gaithersburg, Md.).

C. Assay Methods and Kits

In yet another embodiment of the invention, assays are provided wherein intact cells expressing the proteins of the invention are contacted with biological samples containing molecules suspected of affecting the intracellular activity of the estrogen receptor. After a suitable time period, the effects of such agents on estrogen dependent transactivation activity are measured. Such activity may be quantitated in any number of ways. For example, such cell systems may utilize a reporter system in which the production of the reporter signal is dependent on estrogen dependent transactivation. Numerous reporters may serve equally well in this application including but not limited to, beta-galactosidase, alkaline phosphatase, fluorescent green protein and the like. Furthermore, the methods of the invention may be practiced in bacterial, fungal, insect, avian, mammalian or plant cells. However, yeast-based cell systems are preferred due to low cost and the feasibility of growing yeast cells in plastic devices.

Assays for screening estrogen-containing biological fluid samples are also provided. Assays involving the cell-based systems of the invention may be formatted in any number of configurations. Particularly useful for evaluating large numbers of agents and materials are high throughput screening formats. Traditionally such assays were typically formatted in 96 well plates. However, 384, 864 and 1536 well plates or a custom designed plate may be used in such high throughput assay systems. These systems are often automated using robotics technologies to allow manipulation and processing of large numbers of samples.

According to another aspect of the invention, antibodies immunologically specific for various proteins may be used in the gender sorting assays of the present invention. Such antibodies may be monoclonal or polyclonal. Additionally, antibody fragments having binding affinity for various proteins may also be used to advantage in the gender sorting assays. Such antibody fragments comprise Fab, Fab', F(ab')2, F(v) and Sfv generated recombinantly. Such antibodies or fragments thereof may be used to advantage in the methods and kits of the present invention as described below.

In another aspect, the invention includes kits to facilitate the use of the compositions and methods disclosed herein. Exemplary kits include the expression plasmids and yeast strains of the invention, and/or variants thereof. Also provided are beta-glucoronidase enzymes or sulfatase enzymes or plasmids encoding the same. Protocols for use of the compositions of the invention for the particular application and the necessary reagents to carry out the application are also provided. Such reagents may include, but not be limited to, buffers, solvents, media and solutions, substrates and cofactors, vectors and host cells, and detection or reporter reagents. Accessory items may include vials, vessels, reaction chambers and instruction sheets.

The following protocols are provided to facilitate construction of the expression plasmids for use in the methods and kits of the present invention.

Yeast Media, Strains and Plasmids

Standard yeast media were prepared as described (22). YPD composed of Yeast Extract (20 grams per liter), Peptone (20 g/liter), Dextrose (20 g/Liter) is preferred for use in the invention as most yeast strains grow in this media. Yeast selective media (complete-drop out) used to maintain plasmids composed of yeast nitrogen base 1.7 g/L, ammonium sulfate 5 g/L, dextrose 20 g/L, different amino acids and other supplements were added depending on the requirements of the particular yeast strain. For example if the yeast plasmid contains LEU2 marker, the leucine is dropped out from the media in order to select the plasmid.

Figure 4:
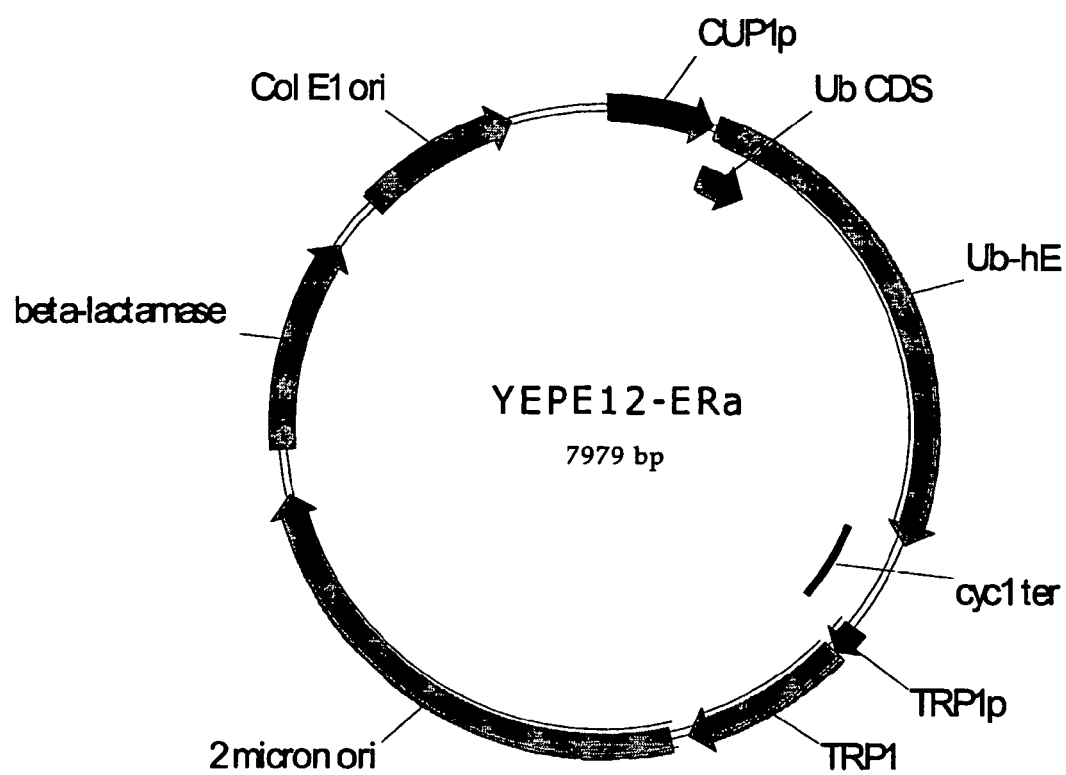
FIG. 4 (YEpE12-ERα) is a schematic diagram of the yeast expression plasmid utilized in the practice of the present invention (Graumann et al., 1996). A yeast expression plasmid is shown which encodes full-length human estrogen receptor alpha. The coding sequence is inserted into the yeast expression vector to produce a ubiquitin (UBI)-fusion protein under the control of a CUP1 promoter. TRP1 is the tryptophan selectable marker and 2 μm is for replicating yeast DNA.

Yeast strains suitable for use in the present invention include the yeast strain Y4727, snq2::Δ pdr5::kanMX: Matα his3-Δ200 leu2-Δ0 lys2-Δ0 met5-Δ0 trp1-A63 ura3-Δ0 snq2::Δ pdr5::kanMX (original strain Y4747 was a gift from Dr. Jeff Boeke) BJ1991 Mat α prb1-1122 pep4-3 leu2 trp1 ura3-52 gal2 (a gift from Dr. Beth Jones), and RS188: MATa leu2-3,112 trp1-1 ura3-1 ade2-1 his3-11,15 can1-100, Construction of the β-Glucuronidase Expression Plasmids A series of yeast expression plasmids have been constructed, all of which are yeast-*E. coli* multicopy shuttle plasmids, containing LEU2 as a yeast transformation marker. See Table 8. FIG. 5 depicts an exemplary plasmid of the invention that is suitable for GUS production in our assay—plasmid pRS425-GPDp-UB-GUS is comprised of plasmid pRS425 (23) *E. coli* GUS from reference 24, human ubiquitin (amplified from plasmid YEpE12; Graumann et al., 1996) and *S. cerevisiae* GPD promoter (plasmid pRS423GPDp was described in Mumberg et al., 1995). See FIG. 4 herein. However, as described herein, additional plasmids for Gus expression were constructed and tested. Those plasmids include pRS425-ADH1p-GUS, pRS425-ADH1p-α-factor-GUS1, pRS425-GPDp-Ub-GUS1, pRS425-GPDp-Ub-α-factor-GUS1, pRS425-GPDp-α-factor-Ub(pro)-GUS1, pRS425-GPDp-α-factor-Ub(met)-GUS1 and pRS425-CUP1p-Ub-GUS1. pRS425-GUS1 was produced by cloning the XhoI-SacI fragment (containing *E. coli* β-Glucuronidase from plasmid pGUS1 (24) into the XhoI-SacI sites of plasmid pRS425 (23). The next construction involved addition of a promoter, and giving rise to plasmid pRS425-ADH1p-GUS. An XhoI-HindIII fragment containing the ADH1 promoter was inserted into the XhoI-HindIII sites of the plasmid pRS425-GUS. The ADH1 promoter XhoI-HindIII fragment was cloned using polymerase chain reaction (PCR), followed by amplification of the ADH1 promoter from the plasmid pGRIP1 (25). The following primers were used to amplify the full length ADH1 promoter: ADH1-XhoI: 5'-g ctcgagagcacagatgcttcgttg-3' (SEQ ID NO: 1) and ADH1-HindIII: 5'-gcaaagcttggagttgattgtatgc-3' (SEQ ID NO: 2). The underlining indicates the nucleotide sequence of the XhoI and HindIII restriction sites. PCR of the DNA fragment involved amplification in 30 cycles (96° C.—30 sec., 54° C.—1 min. and 72° C.—3 min.) using high replication fidelity Deep Vent Polymerase (New England Biolabs). The PCR product was then digested with XhoI and HindIII, and subsequently cloned into the XhoI-HindIII sites of pRS425-GUS. pRS425-ADH1p-α-factor-GUS, comprises a secretory signal fused in frame with the N-terminus open reading frame of GUS. Nucleic acid sequences encoding the alpha factor signal from plasmid pPIC9 (Invitrogen) were amplified by PCR using the primers alpha-HindII (forward): 5'-acc aagctt att cga agg atc caa acg atg ag-3' (SEQ ID NO: 3) and alpha-HindIII (reverse): 5'-gcc aagctt gga gcc tct ctt ttc tcg aga g-3' (SEQ ID NO: 4). Again the underlining indicates the nucleotide sequence of the restriction HindIII site. The PCR product was digested with Hind III and subsequently cloned into the Hind III site of pRS425-ADH1p-GUS, in frame with the open reading frame of GUS. Similarly the plasmids pRS425-GPDp-Ub-GUS1, pRS425-GPDp-Ub-α-factor-GUS1, pRS425-GPDp-α-factor-Ub(pro)-GUS1, pRS425-GPDp-α-factor-Ub(met)-GUS1 were constructed using plasmids pRS425-GPDp as an original vector. The ubiquitin coding DNA fragment was amplified from YEpE12 (Graumann et al., 1996). The plasmid pRS425-CUP1p-Ub-GUS1 was constructed by replacing the GPDp-Ub fragment from plamsid pRS425-GPDp-Ub-GUS1 with CUP1p-Ub fragment derived from plasmid pRS425-CUP1-Ub-CfUSP (Tran et al., 2001).

Yeast Transformation

Briefly, yeast cells were cultured in 5 mL of YPD liquid medium overnight at 30° C. The cell culture was diluted 1:20 in YPD media and further grown until cell density reached an O.D of 0.6. at $OD_{600}$. The cells were pelleted by centrifugation and washed with 10 mL of 10 mM Tris-Hcl pH 8.00, 1 mM EDTA (TE) containing 0.1M lithium acetate. Pelleted cells were resuspended in 10 mL of TE plus 0.1M lithium acetate and incubated at 30° C. for 1 hour. Cells were collected and resuspended in 0.5 mL of TE plus 0.1M lithium acetate. Aliquots of cells (50 µL), were incubated for 15 minutes at 30° C. with 1–2 µg plasmid DNA in the presence of 5 µg of denatured salmon sperm DNA as DNA carrier. In the case of co-transformation, the indicated plasmids were added simultaneously. 50% polyethyleneglycol of molecular weight 4000, diluted in TE, was added to a final concentration of 35%. DMSO was added to the transformation solution simultaneously to a final concentration 3%. The samples were mixed well by vortexing and incubated for an additional 30 minutes at 30° C. The cell mixture was then heated for 15 minutes at 42° C. Cells were collected and plated onto appropriate yeast selective media. Transformants of 4 plasmids were selected on complete media without tryptophan, uracil, leucine or histidine.

A. Accurate and Efficient Estrogen Transactivation as assessed by β-Galactosidase Activity Assays using o-nitrophenyl-beta-D-galactopyranoside (ONPG) as a substrate.

Yeast cells containing yeast expression plasmids for human estrogen receptor and estrogen-inducible reporter gene were grown overnight in selective liquid media at 30° C. and were diluted in pre-warmed liquid selective media to 0.1 at $OD_{600}$ ($OD_{culture}$). See Lyttle et al., 1992. 100 µl of the cell culture was spiked into each well of a 96-well microtiter plate. Ligand (2 µl diluted in DMSO) was added to each well to produce a final concentration of 2% DMSO. As a control, 2 µl of DMSO were also added to additional test wells. The final concentration of 17-β estradiol ranged from 100 pM to 10 nM.

The cells were incubated in the presence of the ligand in a shaker at 30° C. After 4 hours of incubation, 100 µl of 2×"Z" Sarcosine-ONPG buffer (120 mM $Na_2HPO_4$, 80 mM $NaH_2PO_4$, 20 mM KCl, 2 mM $MgSO_4$, 100 mM beta-mercaptoethanol (Sigma), pH 7.0, 0.4% lauroyl sarcosine (Sigma), 4 mg/mL ONPG (Diagnostic Chemicals limited) was added to each well and the plate was further incubated at 37° C. The 2×"Z" Sarcosine-ONPG buffer was freshly prepared or stored at −20° C. prior to use. After incubation at 37° C. for 1 hour, the reaction was stopped by adding 100 µL of quenching solution 0.5 M $Na_2CO_3$ and the $OD_{405}$ ($OD_{reaction}$) was determined. Beta-galactosidase activity was measured in a micro plate reader (Biotek) at a wave length of 405–450 nanometers. The relative activity of β-galactosidase was calculated as follows:

$$(1000 \times OD_{reaction})/(t_{incubation} \times OD_{culture}).$$

| "Z" Buffer | | |
|---|---|---|
| 16.1 g | $Na_2HPO_4\ 7H_2O$ | (60 mM) |
| 5.5 g | $NaH_2PO_4\ H_2O$ | (40 mM) |

| -continued | | |
|---|---|---|
| "Z" Buffer | | |
| 0.75 g | KCl | (10 mM) |
| 0.246 g | $MgSO_4\ 7H_2O$ | (1 mM) |
| 2.7 ml | beta-mercaptoethanol | (50 mM) |

B. Accurate and Efficient Gender Sorting of Allantoic fluids, using Exogenously supplied GUS-ONPG as β-Galactosidase substrate.

The present assay is similar to the estrogen-induced transactivation assay described above. However, in this assay, estrogen-conjugates present in allantoic fluids from 17-day incubated eggs are tested. Unless present at very high concentrations (approximately 10 micromolar (µM)) estrogen conjugates themselves do not induce receptor transactivation because of the low affinity of the estrogen receptor for such conjugates. This concentration greatly exceeds that present in allantoic fluids which is approximately 200 pM. Thus, the present assay consists of two steps: a) release of estrogen from conjugated forms present in allantoic fluids by Glucuronidase (from snail juice, Sigma, cat. #G7017); and b) assessing the released hormone for its ability to stimulate production of the reporter gene in the yeast based transactivation assay.

Initially, allantoic fluids are exposed to beta-glucuronidase. 75 ul of each allantoic fluid sample was placed into a microcentrifuge tube. To each tube 40 ul of 0.2 M Acetate Buffer pH 4.6 was added. 20 ul of beta-glucuronidase from snail (Sigma cat. #G7017) was added and the entire reaction mixed well. The reactions were incubated at 37° C. for 1 hour. Beta-glucuronidase will cleave the estrogen-conjugates in allantoic fluids thereby releasing free estrogen. In order to inactivate the GUS enzymes, the reactions were heated at 95° C. for 5 minutes. The GUS heat inactivation step is required when snail GUS is used as the snail GUS contains other enzymes that also cleave ONPG. Of note, when purified E. coli GUS was used (Sigma #G-7396), the GUS inactivation step was not required because E. coli GUS does not interfere with ONPG cleavage. The released estrogen was utilized in a transactivation assay in yeast. Yeast cells containing yeast expression plasmids for human estrogen receptor (YEpE12) and an estrogen-inducible reporter gene (YRpE2) were grown overnight in selective liquid media at 30° C. and diluted in pre-warmed liquid selective media to a density of 0.1 at $OD_{600}$ ($OD_{culture}$). 100 µl of cell culture was spiked into each well of a 96-well microtiter plate. Four to eight µl of the GUS-treated allantoic fluids were added to the yeast cell suspension. The cells were incubated in the presence of the ligand in a shaker at 30° C. After 4 hours of incubation, 100 µl of 2×"Z" Sarcosine-ONPG buffer (120 mM $Na_2HPO_4$, 80 mM $NaH_2PO_4$, 20 mM KCl, 2 mM $MgSO_4$, 100 mM beta-mercaptoethanol (Sigma), pH 7.0, 0.4% lauroyl sarcosine (Sigma), 4 mg/mL ONPG (Diagnostic Chemicals limited) was added to each well and the plate was further incubated at 37° C. The 2×"Z" Sarcosine-ONPG buffer was freshly prepared or stored at −20° C. prior to use. After incubation at 37° C. for 1 hour, the reaction was stopped by adding 100 µL of quenching solution 0.5 M $Na_2CO_3$ and the $OD_{405}$ ($OD_{reaction}$) determined. Beta-galactosidase activity was measured in a micro plate reader (Biotek) at a wave length of 405–450 nanometers (nm) as described above.

Preferably, the estrogen source for analysis is obtained from the allantoic fluid of the egg that is treated with beta-glucuronidase enzyme. β-glucuronidase may be exogenously supplied or endogenously produced from yeast cells harboring a Gus expression plasmid.

C. Accurate and Efficient Gender Sorting using Estrogen-conjugate containing Allantoic Fluids, Endogenous GUS-ONPG as β-Galactosidase substrate.

Yeast cells BJ1991 containing yeast expression plasmids for human estrogen receptor (YEpE12; See Graumann et al., 1996) and estrogen-inducible reporter gene (YRpE2) and a vector for GUS expression (pRS425-GPDp-Ub-GUS1) were able to grow in standard synthetic minimum medium (20 g glucose, 5 g ammonium sulfate, and 1.7 g yeast nitrogen base per liter). Notably, the optimal pH for E. coli GUS activity is 6.8 while yeast standard synthetic medium has a pH 5.2. Yeast cells were grown overnight in special selective liquid media (SSLM, standard liquid media mix with 10×NEB4 buffer in 9:1 ratio, pH 6.4) at 30° C. and were diluted in pre-warmed SSLM to 0.2 at $OD_{600}$ ($OD_{culture}$). 80 µl. of the cell culture was spiked to each well of a 96-well microtiter plate. 20 ul of allantoic fluid from 17-day incubated eggs were added to the wells. As controls, 20 µl of $H_2O$ or 17-β estradiol (1 nM) were added to additional test wells. The cells were incubated in the presence of the ligand in a shaker at 30° C. After 4 hours of incubation, 100 µl of 2×"Z" Sarcosine-ONPG buffer [120 mM $Na_2HPO_4$, 80 mM $NaH_2PO_4$, 20 mM KCl, 2 mM $MgSO_4$, 100 mM beta-mercaptoethanol (Sigma), pH 7.0, 0.4% lauroyl sarcosine (Sigma), 4 mg/mL ONPG (Diagnostic Chemicals limited] was added to each well and the plate was further incubated at 37° C. for 1 hour. The 2×"Z" Sarcosine-ONPG buffer was freshly prepared or stored at −20° C. prior to use. After incubation at 37° C. for 1 hour, the reaction was stopped by adding 100 µL of quenching solution 0.5 M $Na_2CO_3$ and the $OD_{405}$ ($OD_{reaction}$) determined. Beta-galactosidase activity was measured in a micro plate reader (Biotek) at a wave length of 405–450 nanometers as previously described.

| NEB4 (10 × Buffer) | 500 mM Potassium acetate |
| --- | --- |
|  | 200 mM Tris-Acetate |
|  | 100 mM magnesium acetate |
|  | pH 7. |

For some applications, it may be advantageous to use MP medium, which can be packed as a dry powder, as a substitute for SSLM (standard liquid medium mix with 10×NEB4 buffer in 9:1 ratio, pH 6.4). MP is combination of standard synthetic medium with potassium acetate at a final concentration of 50 mM. MP medium has a similar buffering capacity to that of SSLM medium, but it may be prepared and shipped as a dry powder.

D. Accurate and Efficient Gender Sorting of Allantoic Fluids, using Exogenously supplied E. coli GUS added directly into the assay media, YRpE2SSA4-lacz as a reporter and ONPG as the β-Galactosidase substrate.

For applications in which the gender sorting assays of the present invention are used in large scale operations, the following modifications may be used to advantage. These modifications render the gender sorting assays even more robust and, therefore, amenable to high throughput processes. Accordingly, an additional reporter has been constructed which utilizes the rapid response, inducible heat shock promoter SSA4. The present inventors have also discovered that the use of MP medium, which can be packed as a dry powder, eliminates the need for supplementary beta-mercaptoethanol in the "Z" buffer (see below). The modified assay is similar to the estrogen-induced transactivation assay described above. In this assay, however, estrogen-conjugates present in allantoic fluids from Day 17 incubated eggs were tested.

Figure 3A:
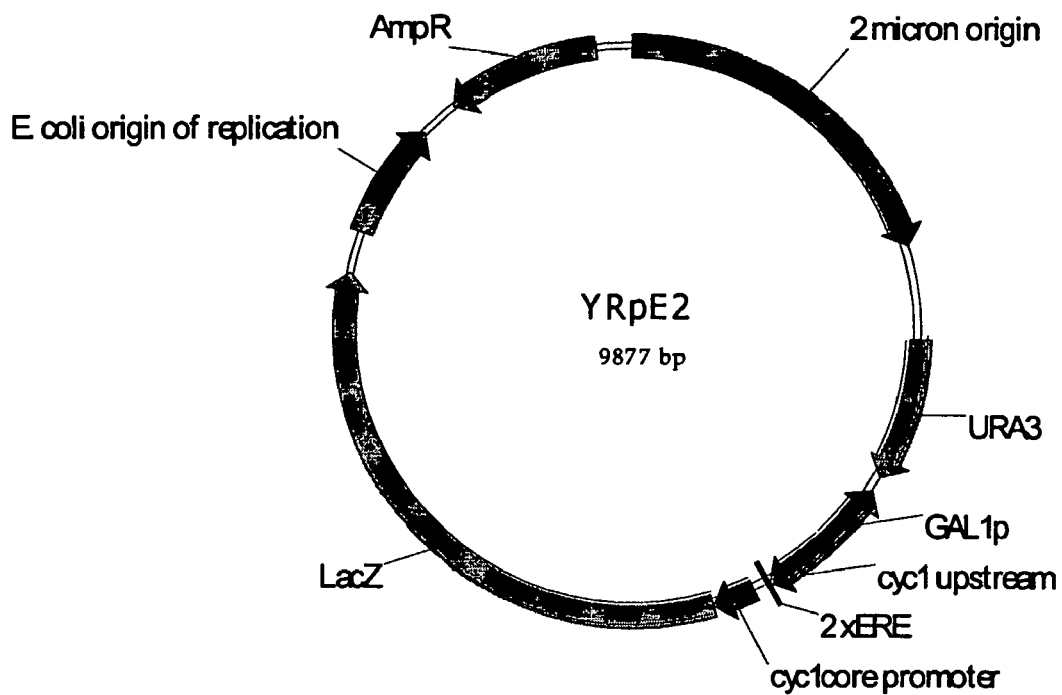
FIG. 3A is a schematic diagram of the LacZ-reporter gene with estrogen response elements (ERES). The yeast reporter plasmid, YRpE2, contains two copies of an ERE (Lyttle et al., 1992) located upstream of the iso-1-cytochrome c (CYC1) promoter which is coupled to the E. coli beta-galactosidase gene (lacZ). This yeast-E. coli multicopy shuttle plasmid contains URA3 as a yeast transformation marker.
Figure 3B:
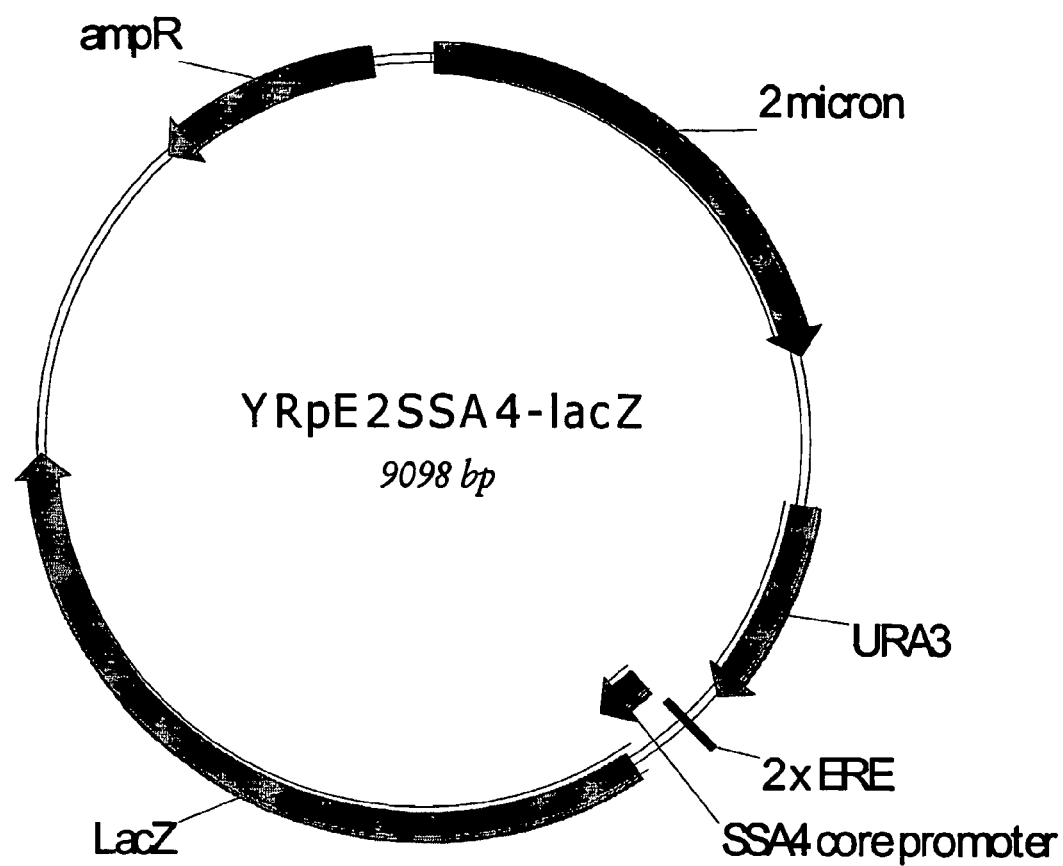
FIG. 3B is a schematic diagram of the LacZ-reporter gene with EREs. The yeast reporter plasmid, YRpE2SSA4-lacZ, contains two copies of an ERE (Lyttle et al., 1992) located upstream of the yeast heat shock inducible (SSA4, Genbank Accession number: J05637) promoter which is coupled to the E. coli beta-galactosidase gene (lacZ). This yeast-E. coli multicopy shuttle plasmid contains URA3 as a yeast transformation marker.

Briefly, yeast strain BJ1991 comprising yeast expression plasmids expressing the human estrogen receptor (YEpE12) and an estrogen-inducible reporter gene (YRpE2SSA4-lacZ; FIG. 3B) were grown overnight in MP selective liquid media at 30° C., after which the overnight cultures were diluted in MP liquid selective media to an $OD_{600}$ of 0.2. Purified E. coli GUS (Sigma #G-7396) was added to the diluted yeast cell culture to a final concentration 1 unit per 100 µl. Eighty microliters of the yeast cell culture was spiked to each well of a 96-well microtiter plate. To each well, 20 µl of allantoic fluid from Day 17 incubated eggs were added. The yeast cell/allantoic fluid mixture was incubated at 30° C. for 1 hour, after which 100 µl of 2×"Z" Sarcosine-ONPG buffer without beta-mercaptoethanol (120 mM $Na_2HPO_4$, 80 mM $NaH_2PO_4$, 20 mM KCl, 2 mM $MgSO_4$, pH 7.0, 0.4% lauroyl sarcosine, 4 mg/mL ONPG) was added to each well and the plate was further incubated at 37° C. The 2×"Z" Sarcosine-ONPG buffer was freshly prepared or stored at −20° C. prior to use. After incubation at 30° C. for 30 minutes reaction colors were determined using a CCD camera to measure the number of pixels in each wells.

EXAMPLE I

17 β-estradiol Dependent Transactivation in Yeast Cells Expressing Estrogen Receptor In accordance with the present invention, compositions and methods are provided for pre-hatch gender sorting in avian eggs. It has previously been demonstrated that the concentration levels of estrogens in the conjugated form is higher in female allantoic fluids as compared to male allantoic fluids (19) and FIG. 1. Thus, this fluid provides ideal starting material for gender sorting of chicken eggs which is based on estrogen concentration levels.

Using several classic methods (radioimmunoassays, etc), one can determine the concentration of estrogens in different biological samples. However, these methods are cumbersome, expensive and not readily adaptable to high throughput formats. The present method described and claimed herein provides robustness, cost-effectiveness and is 100% accurate, thereby satisfying industrial requirements.

As shown in Table 2, the transactivation system of the invention responds only to a specific ligand for the estrogen receptor, 17-β estradiol. Other ligands (Table 2) have very little transactivating activity. Both estrone sulfate and estrone glucuronide have very little to no effect on estrogen transactivation. Furthermore, the yeast transactivation assay is 100-fold more sensitive to 17-β estradiol when compared to mammalian cell assays and no transactivation was observed with the indicated concentration of estrogen glucuronides. The data in the following Table 2 demonstrate that the human estrogen receptor-driven yeast sensor is extremely sensitive and selective for 17-β Estradiol.

TABLE 2

Specificity and selectivity of estrogen sensor. Cross-activity was determined at concentration of 50% maximum potency.

| Compound | Percent Cross Reactivity* |
| --- | --- |
| 17-β Estradiol | 100 |
| Estrone | 8 |
| 16-Hydroxyestrone | 4.0 |
| Estriol | 0.4 |
| Estrone Sulfate | <0.25 |
| Estrone Glucuronide | <0.25 |

TABLE 2-continued

Specificity and selectivity of estrogen sensor. Cross-activity was determined at concentration of 50% maximum potency.

| Compound | Percent Cross Reactivity* |
| --- | --- |
| 2-Methoxyestrone | <0.25 |
| 4-Hydroxytamoxifen | <0.25 |
| Androstenediol | 0.08 |
| Testosterone | <0.05 |
| Dihydrotestosterone | <0.05 |
| Mesterolone | <0.05 |
| Dehydroepiandrosterone | <0.05 |
| Androstenedione | <0.05 |
| Androsterone | <0.05 |
| Progesterone | <0.025 |
| 17-Hydroxyprogestreone | <0.025 |
| Danasol | <0.025 |
| Corticosterone | <0.025 |
| Hydrocortisone | <0.025 |

EXAMPLE II

Figure 2C:
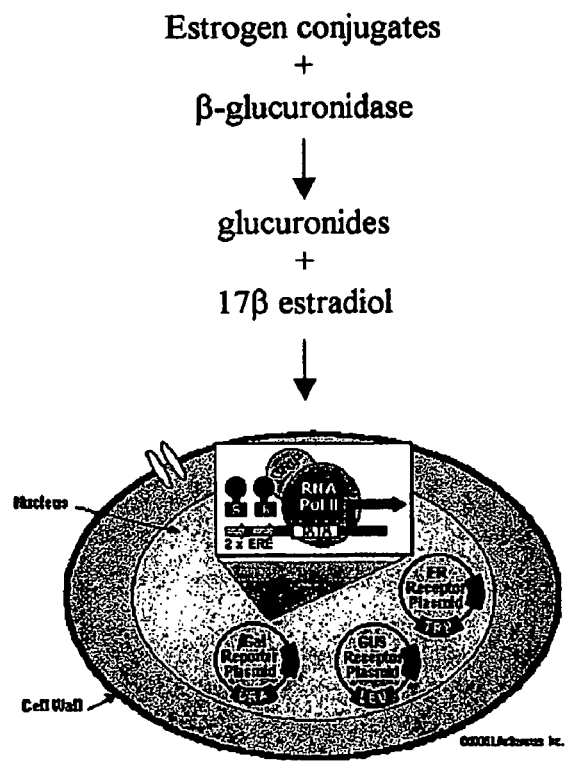

Treatment of Estrogen Conjugates from Allantoic Fluids with Exogenous GUS Followed by Yeast Transactivation Assay A two step treatment of allantoic fluids with exogenous GUS [snail juice GUS (Sigma #G-7017) or bacterial Gus (Sigma #G-7896)] and subsequent use of a yeast estrogen sensor to estimate the level 17β-estradiol released from the allantoic estrogen conjugates is described. A schematic diagram of the assay is shown in FIGS. 2A–2C. The yeast strain used in the present example has been transformed with a yeast expression vector for human estrogen receptor and an estrogen-inducible reporter gene. As described above, in the absence of GUS treatment, allantoic fluids do not induce transactivation of the estrogen biosensor. Accordingly, allantoic fluids were treated with Glucuronidase isolated from snail juice (Sigma cat#G-7017) or bacterial GUS (Sigma Cat #G 7896). Treatment of allantoic fluids with snail GUS has been described above. Treatment of allantoic fluids with bacterial GUS is described hereinbelow.

GUS Treatment

Removal of glucuronides was performed in a total reaction volume of 100 μL, containing 10 μL of NEB 3 buffer 10× (100 mM NaCl, 50 mM Tris-HCl, 10 mM MgCl2, 1 mM dithiothretol, pH 7.9) or NEB4 buffer (50 mM potassium acetate 20 mM Tris-Acetate, 10 mM magnesium acetate, pH 7), 50 μL of allantoic fluids, and 10 units of bacterial GUS enzyme. The final concentration of the estrogen-glucuronide conjugates was 1 μM. The reaction mixture was incubated at 37° C. for 1 hour; and stopped by heating at 95° C. for 5 minutes to inactivate the enzyme. After treatment with GUS enzyme, the 17β-estradiol is released from the conjugate. The reporter assays are then performed as follows:

1. 4 to 8 μL of each GUS treated allantoic fluid reaction mix was spiked into the wells of a 96 well microplate.
2. To each well 100 μL of yeast estrogen sensor cell suspension was added, incubated at 30° C. as described above in Example I.
3. The activity of the reporter gene (beta-galactosidase) was measured by adding 100 μl of 2×"Z"-ONPG as described above.

Of note, purified glucuronidase isolated from *E. coli* (Sigma #G-7896), does not interfere with ONPG, and the heating step described in the previous example is required only when using snail juice GUS. Purified glucuronidase from *E. coli* was able to cleave estrogen conjugates with equal efficiency. However, the optimal pH of the reactions catalyzed by snail juice Gus and *E. coli* derived Gus differ significantly (pH 5.2 for snail juice and pH 6.8 for bacterial GUS). The data presented in Table 3 shows a comparison of conventional dissection of bird embryos for sex determination and the yeast based transactivation system of the invention using Gus treated estrogen conjugates isolated from allantoic fluids. As shown in Table 3, there is 100% agreement in sex determination using the two methods.

TABLE 3

Ability to gender sort allantoic fluid from Day 17 Hyaline layer embryos

| Gender | Optical Density |
| --- | --- |
| M | .328 |
| M | .332 |
| M | .338 |
| F | 1.204 |
| F | 2.261 |
| M | .352 |
| F | 2.664 |
| F | 2.424 |
| F | 2.300 |
| F | 2.057 |

The experimental protocol described above employs only 4 μL of allantoic fluid. The data shown in table 3 are based on the determination of estrogen levels after allantoic fluids from hyaline layer embryos were treated with snail β-glucuronidase and subsequently tested in β-galactosidase reporter assays as described above. Among 10 allantoic fluid samples tested, four of the allantoic fluids were from male embryos while six of the allantoic fluid samples were collected from female embryos. As shown herein, that female allantoic fluid samples showed activity equivalent to 4–8 nM estradiol in the undiluted allantoic fluid after β-glucuronidase treatment. The signal elicited by the allantoic fluid samples collected from male embryos was equal to that of the buffer control.

Sex Specific Signal Readily Determined Regardless of Egg Size or Flock Age from which Chicken Eggs are Derived.

Allantoic fluid samples were collected from eggs of a young flock, a flock in peak production and an old flock. The eggs from the young flock were small in size while the eggs from the old flock were large. The yeast-based estrogen sensor described above was used to determine the level of 17-β estradiol. The sex of the embryos was identified at 100% accuracy regardless of flock age. See Table 4.

TABLE 4

Effect of broiler flock age on ability to gender sort allantoic fluid

| Sex by ID | Optical Density | Flock Age (Weeks in Lay) |
| --- | --- | --- |
| F | 2.869 | 2 |
| F | 1.992 | 2 |
| M | .384 | 2 |
| F | 2.676 | 2 |
| F | 4.000 | 2 |
| M | 0.460 | 24 |
| F | 2.845 | 24 |

TABLE 4-continued

Effect of broiler flock age on ability to gender sort allantoic fluid

| Sex by ID | Optical Density | Flock Age (Weeks in Lay) |
|---|---|---|
| M | .385 | 24 |
| F | 2.374 | 24 |
| M | .441 | 24 |
| M | .395 | 34 |
| M | .341 | 34 |
| F | 2.319 | 34 |
| F | 2.405 | 34 |
| M | .399 | 34 |

Thus, the data show that using yeast as a host, male and female eggs can be differentiated based on the level of estrogen receptor transactivation observed in the LifeSensors™ assay. The robustness of the estrogen sensor was tested under different conditions, such as incubation time of eggs, chick species, contamination of blood in the allantoic fluids and the like. All of the experiments demonstrated that the yeast-based estrogen sensor is extremely robust and was successful in determination of the chicken gender 100% of the time.

The ability of the estrogen sensor was also evaluated to determine the sex of different chicken species. See Table 5. Five allantoic fluid samples from each of three different broiler breeds were tested for analysis. Arbor Acres×Classic Yield (AA×CY), Hubbard×Petersen (H×P), and Cobb×Cobb (C×C) strains were the three different breeds evaluated. The assay clearly distinguished between Day 17 male and female embryos regardless of breed. Optical densities less than 0.650 were considered male and optical densities greater than 0.650 were considered female.

TABLE 5

Effect of broiler breed and gender sorting of allantoic fluid by Estrogen Sensor Assay.

| Sample Sex | Breed | Optical Density |
|---|---|---|
| M | AA X CY | .469 |
| M | AA X CY | .437 |
| F | AA X CY | 1.519 |
| F | AA X CY | 1.430 |
| M | AA X CY | .492 |
| M | H X P | .368 |
| M | H X P | .444 |
| F | H X P | 2.869 |
| M | H X P | .389 |
| F | H X P | 1.642 |
| F | C X C | 2.187 |
| M | C X C | .649 |
| F | C X C | 2.613 |
| M | C X C | .471 |
| M | C X C | .458 |

Sex Specific Signal Present in the Allantoic Fluid Samples of Turkey can Also be Detected by Yeast-Based Estrogen Sensor.

Ten allantoic fluid samples from Day 22 Nicholas Turkey embryos were analyzed using classical estrogen analysis by radioimmunoassays. The assay clearly delineated the sex of the turkey embryos. See FIG. 6. Yeast-based estrogen sensor was subsequently used to gender sort. See Table 6. Samples with optical densities less than 0.700 are male and samples with optical densities greater than 0.700 are females. Turkey embryos had a higher average optical density than the chicken samples tested.

TABLE 6

Ability to gender sort allantoic fluid from Day 22 Nicholas Turkey embryos.

| Sex | Optical Density |
|---|---|
| M | .354 |
| F | 2.891 |
| F | 2.866 |
| F | 4.000 |
| M | .419 |
| M | .445 |
| M | .453 |
| F | 4.000 |
| F | 4.000 |
| F | 4.000 |

Yeast-Based Estrogen Sensor can Differentiate Sex at Different Embryonic Stages.

In order to assess whether the methods of the invention were effective at differentiating sex at different embryonic stages, allantoic fluid samples were obtained from embryos at different stages and assessed for estrogen transactivating activity. See Table 7

TABLE 7

Effect of embryo age on ability to gender sort allantoic fluids.

| LS ID | SEX ID | Embryo Age |
|---|---|---|
| .438 | M | 13 |
| .566 | F | 13 |
| .853 | F | 13 |
| .342 | M | 13 |
| .305 | M | 13 |
| .338 | M | 15 |
| .340 | M | 15 |
| .376 | M | 15 |
| .389 | M | 15 |
| .368 | M | 15 |
| .531 | M | 17 |
| .946 | F | 17 |
| 1.270 | F | 17 |
| .414 | M | 17 |
| .434 | M | 17 |
| 1.624 | F | 18 |
| 2.292 | F | 18 |
| 2.966 | F | 18 |
| 0.52 | M | 18 |
| 1.285 | F | 18 |

EXAMPLE III

Production and Secretion of Beta-galactosidase in Yeast

In the previous example, exogenous GUS was employed to cleave the estrogen-glucuronide conjugates. This example shows that the active GUS enzyme can be produced in yeast and effectively used to cleave estrogen conjugates present in allantoic fluids. A series of plasmids were constructed as described in Table 8. In the assays shown, plasmid pRS425-GPDp-Ub-GUS that secretes GUS at high concentrations was employed.

GUS activity inside and outside the cell was measured as follows: Yeast cells were grown in synthetic complete media without leucine to $OD_{600}=0.5$. 50 µL of cell suspension was transferred to 96-well plates. The cell suspension was transferred into eppendorf microfuge tubes and centrifuged at maximal speed on bench top centrifuge for 5 minutes. 50 µL of media (cell-free media) was transferred to 96 microplates wells. 50 µL of PNP-Gluc-2×"Z" Sarcosine-buffer [120 mM $Na_2HPO_4$, 80 mM $NaH_2PO_4$, 20 mM KCl, 2 mM $MgSO_4$, 100 mM beta-mercaptoethanol (Sigma), pH 7.0, 0.4% lauroyl sarcosine (Sigma), 0.5 mg/mL PNP-Gluc (PNP-Gluc is an abbreviation of p-NITROPHENYL-BETA-D-GLUCURONIC ACID;, Diagnostic Chemicals limited)] was added to each well. The buffer was freshly prepared. After incubation at 37° C. for 1 hour . The reaction was stopped by adding 100 µL of quenching solution 0.5 M $Na_2CO_3$. $OD_{405}$ was measured in a micro plate reader (Biotek) at a wavelength of 405–450 nanometers to estimate the relative enzymatic activity of GUS.

It has been previously established that attachment of ubiquitin, a 76 amino acid, highly conserved protein to the N-terminus of other proteins enhances the expression of fused proteins several fold. However, it is not known whether ubiquitin plays any role in the extracellular secretion of proteins. Accordingly, as described herein, several GUS yeast expression vectors have been designed wherein the C-terminus of ubiquitin was attached to the N-terminus of GUS (GDPp-UB-GUS). In addition, a factor secretory sequences were attached at the N-terminus of the ubiquitin-GUS fusion (GPD-α-factor-GUS) as well as between ubiquitin and the GUS gene (GDP-UB-α-factor-GUS). The fusion of ubiquitin increases the stability of the recombinant proteins and preserves their biological properties, thus enhancing the quality and quantity of the proteins that are expressed in yeast and *E. coli* [28, 29].

TABLE 8

GUS Expression in the Cells and Secretion of the Protein.

| Vector (pRS425) | Promoter | Signal Sequence | GUS Activity Inside Cells | GUS Activity Outside the Cells |
|---|---|---|---|---|
| ADH1-GUS1 | ADH1 | — | +++ | − |
| ADH1-α-factor-GUS1 | ADH1 | α-factor | + | − |
| GPD-α-factor-GUS1 | GPD | α-factor | ++ | − |
| GPD-Ub-GUS1 | GPD | Ubiquitin | ++++ | ++++ |
| GPD-Ub-α-factor-GUS1 | GPD | Ubiquitin-α-factor | ++++ | + |
| GPD-α-factor-Ub (pro)-GUS1 | GPD | α-factor-Ubiquitin(pro) | +/++ | + |
| GPD-α-factor-Ub (met)-GUS1 | GPD | α-factor-Ubiquitin(met) | + | + |
| CUP1-Ub-GUS1 | CUP1 | Ubiquitin | ++++ | ++ |

The data described in Table 8 show that attachment of ubiquitin increases expression levels of GUS several fold. The data also shows that only the ubiquitin fusions (with or without α-factor secretory sequences) efficiently secrete GUS. The small amount of GUS activity observed in non-secretory GUS expression strains may be due to release following lysis of dead cells.

EXAMPLE IV

Gender Sorting Sensor Development

The plasmid pRS425-GPDp-Ub-GUS was assessed in additional experiments. This plasmid was used due to its robust GUS expression and high enzymatic activity of GUS in yeast culture media. The GUS producing plasmid was transformed into several yeast strains along with plasmid for expression of human estrogen receptor (YEpE12; See FIG. 4) and estrogen-inducible reporter gene (YRpE2; See FIG. 3A). The strains were screened for growth and GUS production. A yeast strain (BJ 1991) has been identified that grew rapidly with GUS plasmid and produced the highest levels (units) of GUS per mg protein. In addition, this strain was also tolerant of estrogen receptor expression and provides excellent response to estrogen in estrogen transactivation assays.

Synthetic yeast selective growth media have pH ranges between 4.5 to 5.5. The pH optimum for *E. coli* GUS was 6.8 as indicated by the Sigma protocol for GUS assay. To maximize growth of yeast and GUS activity, new media conditions were developed that allow optimum growth of yeast as well as robust allantoic estrogen-conjugate responsiveness.

The yeast strain BJ 1991 was transformed with plasmid pRS425-GPDp-Ub-GUS and grown in the standard yeast media (complete media without leucine, 22). The culture media was supplemented with different salt and buffering conditions by diluting 1:9 with NEB buffer 1, 2, 3, 4 10×-buffers (New England Biolabs). The yeast cells for all the buffering conditions were inoculated at the same $OD_{600}$ 0.1 and grown overnight. No differences were observed in growth rates of the culture. GUS activity was determined after 24 hours of growth in media, as well as in cell lysates using PNP-gluc as a substrate. The GUS activities were measured as described in EXAMPLE III. The data are provided in Table 9.

TABLE 9

GUS secretion and activity in cells grown in different media (NEB1–NEB4)

| Media | GUS activity in media | GUS activity in cells |
|---|---|---|
| NEB1 | 0.117 | 2.693 |
| NEB2 | 0.107 | 2.337 |
| NEB3 | 0.138 | 2.963 |
| NEB4 | 0.945 | 2.939 |
| Standard | 0.87 | 2.535 |

As shown in Table 9, NEB buffer 4 and salt conditions provide the best GUS expression and secretion levels in the media. As demonstrated herein, the final pH of the media is 6.4 after dilution (1:10) of NEB4 (10×) with standard media. Hence, for optimal GUS activity in gender sorting assays, all the experiments and cell growth were carried out in NEB 4 buffer and media conditions. The details of the media are described below.

Mixing Transactivator and GUS Producing Strains to Monitor Gender

As shown above for the test media assessed, use of the NEB4 media provided optimized results for extracellular secretion of GUS from yeast. In the next step, NEB4 media was used to grow yeast and for monitoring gender. There were two approaches to monitor gender: a) using two yeast strains—one for GUS production and the other as the estrogen sensor and b) using a single yeast strain that has been transformed to express both GUS and the necessary components of the estrogen sensor. For the first approach, BJ 1991 cells harboring GPD-Ub-GUS1 were grown independently (GUS producer strain) or transformed with only the human estrogen receptor and ERE-beta-Galactosidase reporter vectors (estrogen transactivator strain). Two batches of cells were thereby generated, one producing secretory GUS and the other strain harboring only the transactivator and reporter gene. Cells were grown in liquid modified media following the brief protocol set forth below.
1. GUS producer cells were grown in liquid synthetic complete NEB4 media without leucine to $OD_{600}$=1–2
2. Transactivator cells were grown in liquid synthetic complete NEB4 media without uracil and tryptophan media overnight to $OD_{600}$=1–2.
3. Transactivator cells were diluted 1/10 or 1/20 in NEB4 complete media (pH=6.4) to $OD_{600}$=0.1
4. 50 μL of GUS producer from (1), 50 μL of Transactivator in NEB4 from (3) and 8 μL of Male or Female allantoic fluid were added to wells in a microtiter plate.
5. Plates were covered with sealer and incubated at 30° C. in a shaker for 4 h.
6. 100 μL of 2×"Z"-ONPG buffer was then added.
7. Incubate at 37° C. for 10 minutes to 1 h.
8. Add 100 μL of quenching solution 0.5M $Na_2CO_3$.
9. Measure at $OD_{405}$ For the second approach, employing a single yeast strain, the BJ1991 strain was transformed with three plasmids: 1) a GUS enzyme expression vector (pRS425-GPDp-Ub-GUS); 2) an expression vector for human estrogen receptor alpha (YEpE12); and 3) a vector expressing an estrogen inducible reporter (YrpE2). Briefly, the BJ1991 yeast strain was transformed with all three expression vectors and grown in liquid synthetic complete NEB4 media without leucine, uracil and tryptophan to $OD_{600}$=1–2. The cells were diluted 1/10 or 1/20 in NEB4 complete media (final pH=6.4) to $OD_{600}$=0.2. To each well of 96-well plate, 4 μL of Male or Female allantoic fluid were added. 100 μl of the diluted cell suspension was then added. Plates were covered with sealer and incubated at 30° C. at shaker for 4 h. 100 μL of 2×"Z"-ONPG buffer was then added and the samples incubated an additional 10 minutes to 1 hour at 37° C. 100 μL of quenching solution (0.5M $Na_2CO_3$) was then added and the $OD_{405}$ measured. Both approaches efficiently distinguished male from female embryos.

Table 10 presents data of gender monitoring using 1 yeast strain harboring all three plasmids.

| Allantoic fluids | OD405 × 1000 | Sex |
|---|---|---|
| DMSO | 449 | |
| estrogen 1 nM | 2982.5 | |
| N191 | 711 | Male |
| N219 | 719.5 | Male |
| N212 | 632 | Male |
| N216 | 696.5 | Male |
| N215 | 661.5 | Male |
| N224 | 836 | Male |
| N229 | 1342 | Female |
| N207 | 1598.5 | Female |
| N228 | 1737 | Female |
| N230 | 1630.5 | Female |
| N199 | 2638.5 | Female |
| N200 | 2812.5 | Female |
| N201 | 2508.5 | Female |
| N202 | 1509 | Female |
| N203 | 2544.5 | Female |

| -continued | | |
|---|---|---|
| Allantoic fluids | OD405 × 1000 | Sex |
| N209 | 2695 | Female |
| N210 | 1625.5 | Female |
| N211 | 2359.5 | Female |
| N214 | 2894.5 | Female |
| N218 | 1973 | Female |
| N220 | 2950 | Female |

Note:
the sex Male or Female was identified independently by open dissection of the embryos.

EXAMPLE V

Male/Female Sex Sorting Using Superior Substrates for Measuring Enzymatic Activity of Beta-galactosidase Many substrates for measuring beta-galactosidase (beta-Gal) activity are commercially available. Examples include ONPG and PNPG (Diagnostic chemicals, Limited) which are colorimetric substrates for beta-Gal. End products of these compounds have yellow color and are measured at absorption wave length 405 nM. Similar to ONPG, PNPG can be used as a beta-galactosidase substrate to distinguish male verse female eggs. MuGal (Diagnostic chemicals, Limited) is another substrate, whose end product emits yellow fluorescence that can be measured using the appropriate excitation/emission filter. Resorufin-beta-D-galactopyranoside (Sigma) is a red fluorescent substrate for beta-Gal. The advantage of using substrates that emit red fluorescence is that living organism do not emit red autofluorescence. Therefore any autofluorescent background due to cell debris, or blood contamination of the allantoic fluids should be zero.

One advantage of the present transactivation system is that the assay is relatively inexpensive to perform. To enhance cost-effectiveness, serial dilutions of substrates were tested in the transactivation assays described herein to ascertain the effects of such cost-saving measures and the ability to distinguish males from females. Ten-fold dilution of ONPG and PNPG compromised the male/female ratio readout (data not shown). A ten-fold dilution of the resorufin substrate, however, did not affect the male/female signal ratio. A 5–10 fold difference in readout between male and female samples was maintained despite sample dilution.

Accordingly, assays were performed using resorufin as substrate at low concentration and allantoic fluids from 30 eggs at 17-Days of incubation. Table 11 shows the results for 24 samples in comparison with sexing data obtained by open egg dissection. Clearly, the method of the present invention provides the accuracy of conventional, time-consuming methods, but in a fraction of the time.

Table 11 shows sec identification using Lifesensor with resorufin-beta-D-galactopyranoside as a substrate in comparison with sex identification using open dissection of embryos.

| | Egg number | | | | | | | |
|---|---|---|---|---|---|---|---|---|
| | 582 | 583 | 584 | 585 | 586 | 587 | 588 | 589 |
| Sex ID | Female | Male | Male | Female | Male | Female | Male | Male |
| Readout | 0.1358 | 0.0000 | 0.0000 | 0.0865 | 0.0000 | 0.1106 | 0.0000 | 0.0035 |

-continued

| | Egg number | | | | | | |
|---|---|---|---|---|---|---|---|
| | 590 | 591 | 592 | 593 | 594 | 595 | 596 | 597 |
| Sex ID | Female | Male | Female | Female | Female | Female | Male | Female |
| Readout | 0.1057 | 0.0032 | 0.1143 | 0.1240 | 0.1229 | 0.1059 | 0.0000 | 0.1236 |

| | Egg number | | | | | | |
|---|---|---|---|---|---|---|---|
| | 598 | 599 | 600 | 601 | 602 | 603 | 604 | 605 |
| Sex ID | Male | Female | Female | Male | Male | Male | Male | Female |
| Readout | 0.0019 | 0.1096 | 0.1126 | 0.0120 | 0.0270 | 0.0000 | 0.0000 | 0.1060 |

The final concentration of resorufin was 0.00025 mg/mL. The assay used 20 µL of allantoic fluids from Day 17 incubated eggs diluted in 80 µL of yeast cells, incubated at 30° C. for 4 hours. Substrates were added and incubated for 10 minutes at 37° C. The readout was measured using a 544 nm excitation filter and a 590 nm emission filter.

Figure 7:
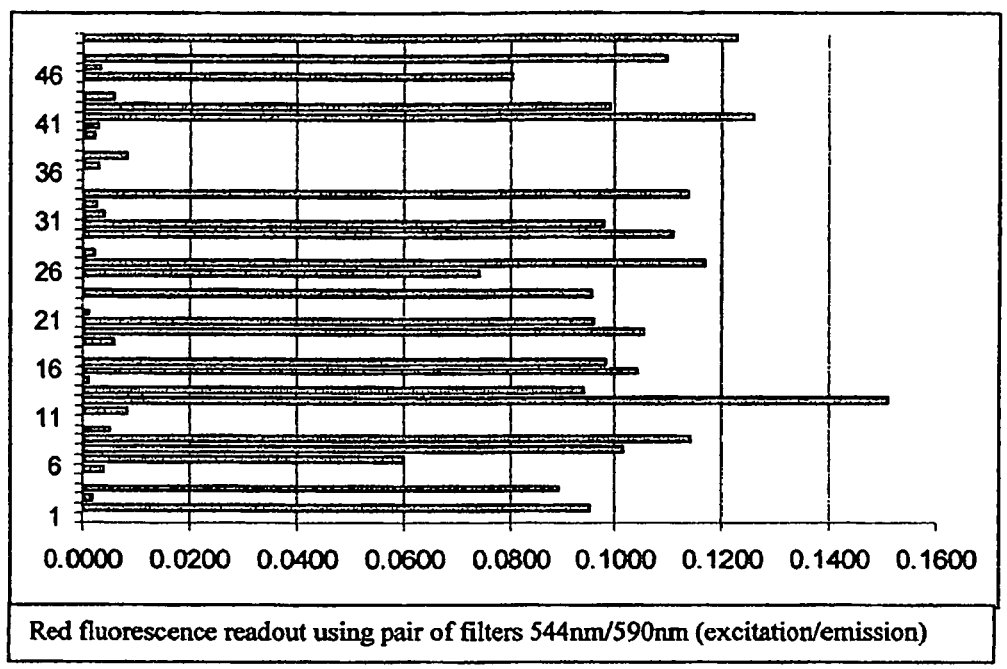
FIG. 7 is a graph showing a transactivation assay using resorufin at concentration 0.00025 mg/mL and allantoic fluids (20 ul allantoic/80 ul of yeast. Samples 768–817). Incubation time was 4 h, followed by addition and incubation with substrates for an additional 10 min at 37° C.

The results depicted in Table 11 are graphed in FIG. 7. There is 100% match between sex and red fluorescent readout: the females have a high readout (higher than 0.0600), and the males have a low readout (lower than 0.01) reflecting differences in estrogen level. Thus, using resorufin-beta-D-galactopyranoside as beta-galactosidase substrate, the background signal has been diminished, thereby generating a higher signal to noise ratio.

EXAMPLE VI

Modification of Gender Sorting Sensor to Shorten Assay Time and Increase Robustness The present inventors have modified the gender sorting assay system to include the use of heat shock promoters. Yeast heat shock promoters such as HSP104, HSP26 and SSA4 are robust promoters which are activated rapidly in response heat shock stress (see Tijirina and Sayer 1998). High levels of these heat shock proteins have been observed within fifteen minutes of exposure of yeast cells to either high temperature (38° C.) or osmotic pressure. Transcriptional activation of HSP26, HSP104 and SSA4 increased 55-, 39-, and 167-fold, respectively, after 15 minutes of exposure to heat shock conditions (Tijirina and Sayre, 1998). Accordingly, an SSA4-based estrogen inducible reporter has been constructed that responds to activation signals with faster kinetics (at least twice as fast) than the CYC1-based reporter described above.

The SSA4-based estrogen inducible reporter plasmid YRpE2SSA4-lacZ was constructed using the ecdysone inducible reporter plasmid pBRSS 6×EcRE-lacZ as the backbone construct (Tran et al., 2001). The Sal1-BamH1 fragment comprising the 6×EcRE ecdysone response elements along with CYC1 promoter of pBRSS 6×EcRE-lacZ have been replaced with a Sal1-BamH1 fragment that contains 2×EREs plus part of the SSA4 promoter. The Sal1-BamH1 DNA fragment comprising 2×EREs plus part of the SSA4 promoter was generated by PCR amplification of yeast *Saccharomyces cerevisiae* genomic DNA using two primers: SSA4-forward primer containing two ERE elements: 5-GC<u>GTCGAC</u>TCTGGTCACAGTGACC*ggtcaca-gtgacc*TTATGGAAGCACCAAG-3' (SEQ ID NO: 5; the Sal1 site is underlined and the two estrogen response elements are indicated in italics) and SSA4-reverse primer starting from the ATG codon: 5'-GT<u>GGATCC</u>CATGATTAT-TGTTTTG-3' (SEQ ID NO: 6; the BamH 1 site is underlined). Of note, SSA4 is a heat shock inducible gene, the transcription of which is rapidly and robustly induced upon heat shock exposure (Tijirina and Sayre, 1998). A PCR product generated using the above template and primers would, therefore, comprise the SSA4 heat shock promoter operably linked to two EREs and flanked by Sal1 and BamH1 restriction enzyme sites.

The data presented in the Table 12 demonstrated that the response of the SSA4-based estrogen inducible reporter plasmid YRpE2SSA4-lacZ to estrogen activation was at least twice as fast as that of the CYC1 promoter-based reporter. The development of the SSA4-ERE reporter system, therefore, significantly expedited the gender sorting ability of the yeast sensor assay. See Tables 13 and 14.

The following is a brief protocol of the estrogen transactivation assays used to compare the CYC1 promoter-based reporter to the SSA4 promoter-based reporter.

1. BJ1991 yeast cells containing YEpE12 (estrogen expressing vector), pRS425-GPDp-Ub-GUS and either reporter plasmid YRpE2 or YRpE2SSA4-lacZ were grown in liquid synthetic MP medium to $OD_{600}$=1–2.
2. Yeast culture was diluted in liquid MP media to $OD_{600}$=0.2.
3. 100 µL of yeast cell suspension were spiked into each well of a 96-well microtiter plate. Estrogen (diluted in DMSO) was added to the wells to a final concentration 5 nM.
4. Plates were covered with sealer and incubated at 30° C.
5. At intervals of 15 minutes, 100 µL of 2×"Z"-ONPG buffer (without beta-mercaptoethanol) was added.
6. Incubations were performed at 30° C. for 15 minutes.
7. Optical densities were determined at $OD_{405}$.

TABLE 12

Time/response comparison of two estrogen inducible reporters (CYC1 promoter-based and SSA4 promoter-based) in response to 5 nM estrogen. The data shown is the average of three independent measurements.

| Time of incubation | CYC1-reporter | SSA4-reporter |
|---|---|---|
| 0 minutes | 0.144 | 0.157 |
| 15 minutes | 0.133 | 0.167 |
| 30 minutes | 0.228 | 0.241 |
| 45 minutes | 0.185 | 0.535 |
| 60 minutes | 0.206 | 0.720 |
| 75 minutes | 0.250 | 0.805 |
| 90 minutes | 0.378 | 0.857 |
| 105 minutes | 0.268 | 1.041 |
| 120 minutes | 0.338 | 0.991 |

Figure 8:
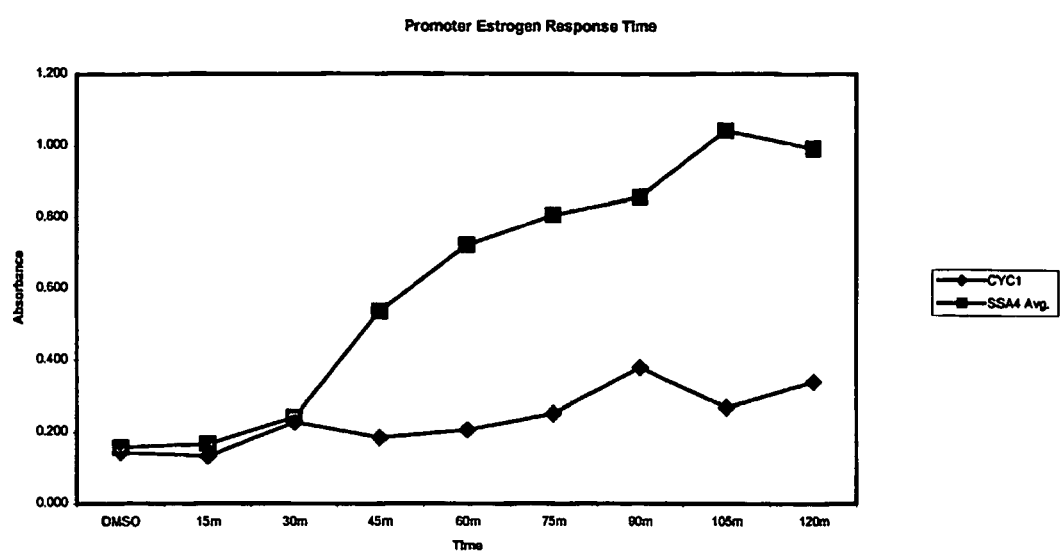
FIG. 8 is a graph showing a comparison of time/response in two transactivation assays in response to estrogen (concentration 5 nM) using YRpE2 (CYC1 promoter based) and YRpE2SSA4-lacZ (heat shock promoter based) reporter vector at an ONPG (substrate) concentration of 0.2%. The incubation times with hormone were varied as shown prior to addition of substrates and subsequent substrate incubation time (15 minutes) at 30° C.

As shown in FIG. 8 and Table 12, the SSA4-based reporter responded to estrogen in only 30–45 minutes, whereas the SSA4-based sensor required approximately 1.5 to 2 hours of incubation time to distinguish male and female allantoic fluids. These results suggest that the cleavage of estradiol glucuronide conjugates to free estradiol is a time limiting factor in such assays. The amount of GUS secreted by yeast cell suspensions ($OD_{600}$=0.2) into the growth media after four hours of growth was less than 0.01 GUS activity units, as compared to a standard titration series of purified *E. coli* GUS (Sigma) using PNPG as a substrate. The present inventors have discovered that supplemention of 100 µl cell suspension reactions with 0.1–1 activity units of GUS (Sigma) reduces the assay time from 2 hours to less than 1 hour.

The following protocol was performed to titrate the GUS activity in allantoic fluid assays.

1. BJ1991 yeast cells comprising YEpE12 (estrogen expressing vector), pRS425-GPDp-Ub-GUS and reporter plasmid YRpE2 or YRpE2SSA4-lacZ were grown in liquid synthetic MP medium to $OD_{600}$=1–2.
2. Yeast cell cultures were diluted in liquid MP media to $OD_{600}$=0.2.
3. *E. coli* GUS (Sigma #G-7396) was added to yeast suspensions to achieve different final concentrations of 100, 10, 1, 0.1, 0.01, 0.001, 0.0001 enzymatic activity units per 100 µl of yeast suspension.
4. Eighty microliters of yeast cell suspension (containing exogenous GUS) were spiked into individual wells of a 96-well microtiter plate. In each well there was either 20 µl of male or female allantoic fluids.
5. Plates were covered with sealer and incubated for 1 hour at 30° C.
6. One hundred microliters of 2×"Z"-ONPG buffer (without beta-mercaptoethanol) was then added.
7. Incubation was performed at 30° C. for 15 minutes.
8. The number of pixels in each well was measured using a CCD camera.

TABLE 13

GUS enzyme titration and the ability of the SSA-4 based sensor to distinguish between male and female allantoic fluids as measured using a CCD camera. The GUS titration was performed as described above.

| GUS (units) | CYC1 Male | CYC1 Female | SSA4 Male | SSA4 Female | SSA4 Male | SSA4 Female |
|---|---|---|---|---|---|---|
| 100 | 0 | 20 | 7 | 400 | 7 | 420 |
| 10 | 0 | 7 | 0 | 500 | 0 | 400 |
| 1 | 0 | 7 | 0 | 620 | 0 | 450 |
| 0.1 | 0 | 2 | 0 | 560 | 0 | 400 |
| 0.01 | 0 | 0 | 0 | 320 | 0 | 50 |
| 0.001 | 2 | 0 | 0 | 40 | 0 | 5 |
| 0.0001 | 1 | 0 | 2 | 5 | 5 | 30 |
| 0 | 1 | 2 | 10 | 10 | 10 | 40 |

The data presented in the Table 13 demonstrated that 0.1–1 units of GUS were sufficient to enhance the sensitivity of gender sorting assays. The cost of 25,000 units of *E. coli* GUS (Sigma) is $16, which means that the additional cost associated with the above-modified assays was less than 0.0075 cents (0.1 unit) of exogenous GUS per assay well to effect a 50% reduction in assay time (reduced from 2 to 1 hour).

The results shown in Table 14 demonstrate the ability of the modified gender sorting assay to accurately distinguish male and female allantoic fluid samples. As shown, five male and five female allantoic fluid samples were tested in the modified gender sorting assay. The assay was performed with the indicated allantoic fluids, using the SSA4-reporter construct in the presence of exogenous GUS (0.1 units per assay) for one hour of incubation time, which was followed by a substrate reaction of 15 minutes.

TABLE 14

Ability of the SSA-4 based sensor in combination with 0.1 unit of exogenous GUS to distinguish between male and female allantoic fluids using either a colorimetric microplate reader or CCD camera.

| | SSA4, clone1 | | SSA4, clone 2 | |
|---|---|---|---|---|
| Allantoic | OD405 measurement | CCD measurement | OD405 measurement | CCD measurement |
| Male | 0.200 | 5 | 0.250 | 6 |
| Male | 0.209 | 7 | 0.221 | 0 |
| Male | 0.254 | 7 | 0.284 | 9 |
| Male | 0.329 | 6 | 0.337 | 6 |
| Male | 0.232 | 9 | 0.257 | 20 |
| Female | 0.672 | 520 | 0.68 | 600 |
| Female | 0.607 | 600 | 0.615 | 675 |
| Female | 0.506 | 600 | 0.487 | 700 |
| Female | 0.514 | 590 | 0.506 | 640 |
| Female | 0.561 | 600 | 0.574 | 650 |

EXAMPLE VII

Detection of Steroid and Drug-conjugates in Biological Fluids

The human body actively glucuronidates a variety of steroids and xenobiotics. The liver contains several UDP-glucuronsyltranferases (UGT) that glucuronidate many drugs and steroids (Burchell et al, 1994). Glucuronidation of steroids and drugs is a widely used mechanism for the inactivation and removal of these agents from the body. Drug and steroid-glucuronides or sulfates have lower affinity for their cognate receptors or targets. If one can de-conjugate a particular drug or xenobiotic, a receptor or drug-target driven sensor can then be used to estimate the amount of the steroid or drug released from the conjugate. The glucuronidases have rather broad specificity for glucuronidated molecules. Hence, it is possible to use a selected series of the glucoronidase expression vectors that are transformed into a yeast strain harboring the target receptor or enzyme. Incubation of biological fluids, including without limitation, sera, urine or saliva will convert low affinity inactive drug steroid-conjugate into a high affinity active drug that will bind to the target receptor to activate the receptor and promote the transactivation signal.

An exemplary drug detection assay can be performed using the following steps:

1) The appropriate GUS producing cells are transformed with the target receptor expression vector and the reporter gene.
2) The GUS secretory cells are grown in selective media achieving an O.D=0.2 or alternatively, an O.D that allows maximal cleavage of the drug conjugate. The cells, 20–100 µL are transferred to 96 or 384 well plates.
3) To each well 1–10 µl of a biological ample is added. The salt and buffer conditions are optimized in cell suspension to maximize GUS enzyme function. The suspension is approximately 5–30 microliters. Different volumes of biological fluids are assayed in duplicate.
4) To each well, appropriate substrate is added to determine the induction of the reporter gene as described above for Examples III, IV and V.

5) The amount of the de-conjugated target receptor ligand is estimated by comparing the signal obtained from the biological fluid to a standardized control ligand assayed at the same time.

6) Standard control reactions, e.g., with ligands that target the receptor under investigation, are performed on the same plate in which the conjugated ligand or xenobiotics are assayed. Appropriate software is then utilized to facilitate calculation of the concentration of the conjugated xenobiotics following the computation of the signal detected from the control wells.

Detection of conjugated xenobiotics by the receptor-based sensors of the invention has several applications in determining the sensitivity and toxicity of various drugs, ligands and steroids in the human population.

For example, several drugs become more toxic once they are glucuronidated or modified by drug metabolism pathway such as the cytochrome P450 series of enzymes. A rapid sensor that efficiently assesses the level of glucuronidated drugs will aid the clinician in the development of drug tolerance studies as well as toxic dose determinations in selected patients.

Conversely, conjugation of xenobiotics is often attributed to the loss of activity and clearance from the human system. This is due to the ability of different individuals to glucuronidate certain steroid and other xenobiotics and specifically the function of human UDP-glucuronsyltranferases. It is also feasible that the glucuronidation pattern of an individual is related to drug sensitivity and toxicity. In this respect the receptor and GUS encapsulated sensors are tools for studying pharmocogenomics of populations. Thus the sensors can be used as tools to stratify populations for clinical trials.

REFERENCES

1. Schroeder, C. H. "How to tell the baby chick's sex", Everybody's Poultry Journal , 289 (1933) 293–297.
2. Taylor, L. W. "Sexing day old chicks", Nulaid News, San Francisco, Calif. July (1933) 14.
3. Warren, D. C., "Renowned poultry geneticist reminisces about feather sexing chicks", Poultry Tribune, February (1976) 31–34.
4. Jull, M. A., 1934. The feasibility of sex segregation in day-old chicks. Poultry Sci. 13:250–254
5. Masui, K. and Hasimoto, J. 1933. Sexing baby chicks. Journal Printing Co., Vancouver, B.C.
6. Hoh, E. "The Determinator", Far Eastern Economic Review, Sep. 25, (1997).
7. Ross Breeders, This name of one Poultry Farm
8. Bacon, L. D., Smith, E., Crittenden, L. B. and Havenstein, G. B. 1988. Association of slow feathering (K) and an endogenous viral (ev21) gene on the Z chromosome of chickens. Poultry Sci. 67:191–197.
9. Crittendon, L. B., McMahon, S., Halpern, M. S. and Faldly, A. M. 1987. Embryonic infection with the endogenous avian leukosis virus Rous-associated virus-O alters response to exogenous avial leukosis infection. J. Virol. 61:722–725.
10. Hutt, F. B. and Cole, R. K. 1973. Identification of sex in chicks by use of the gen $S^{a1}$. Poultry Sci. 52:2044 (abstr.)
11. Laughlin, K. F., Lundy, H. and Tait, J. A. 1976. Chick embryo heart rate during the last week of incubation: Population studies. Br. Poultry Sci. 17:293–301.
12. Glahn, R. P., Mitsos, W. J. and Wideman, Jr., R. F. 1987. Evaluation of sex differences in embryonic heart rates. Poultry Sci. 66:1398–1401.
13. Clinton, M. 1994. A rapid protocol for sexing chick embryos (*Gallus g. domesticus*). Animal Genetics 25:361–362.
14. Uryu, N., Nagata, Y., Ito, K., Saitoh, H. and Mizuno, S. Research note: Determination of the sex of chickens by a biotin-labeled deoxyribonucleic acid probe. Poultry Sci. 68:850–853.
15. Petitte, J. N. and Kegelmeyer, A. E. 1992. Sex determination of chick embryos using a W chromosome-specific oligonucleotide probe and PCR. Proceedings of the XIX World's Poultry Congress, Amsterdam, 521.
16. Teng, C. T. and Teng, C. S. 1977. Studies on sex organ development. Biochem. J. 162:123–134.
17. Guichard, A., Cedard, L., Mignot, T. H., Scheib, D. and Haffen, K. 1977. RIA of steroids produced by cultured chick embryonic gonads and differences according to age, sex and size. Gen. Comp. Endo. 32:255–267.
18. Tanabe, Y., Nakamura, T., Fujioka, K. and Doi, O. 1979. Production and secretion of sex steroid hormones by the testis, the ovary and the adrenal glands of embryonic and young chickens (*Gallus domesticus*). Gen. Comp. Endo. 39:26–33.
19. Gill, V., Robertson, H. A. and Betz, T. W. In vivo estrogen synthesis by the developing chicken (*Gallus gallus*) embryo. Gen Comp. Endo. 49:176–186.
20. Romanoff, A. 1967. Biochemistry of the Avian Embryo. John Wiley and Sons, Inc., New York.
21. Sambrook, J., Fritsch, E. F. and Maniatis, T. 1989. Molecular Cloning: A Laboratory Manual, Second Edition. Cold Spring Harbor Laboratory, Cold Spring Harbor, N.Y.
22, Sherman, F., Fink, G. and Hicks, J. 1986. Methods in yeast genetics. Cold Spring Harbor Laboratory, Cold Spring Harbor, N.Y.
23. Sikorski, R. S., and Hieter. P. 1989. A system of shuttle vectors and yeast host strains designed for efficient manipulation of DNA in *Saccharomyces cerevisiae*. Genetics 122:19–27.
24. Marathe, S. V. and McEwen, J. E. 1995. Vectors with the gus reporter gene for identifying and quantitating promoter regions in *Saccharomyces cerevisiae*. Gene 154: 105–7.
25. Walfish, P. G. et al., 1997. Yeast hormone response element assays detect and characterize GRIP1 coactivator-dependent activation of transcription by throid and retinoid nuclear receptors. Proc. Natl. Acad. Sci. USA 94:3697–3702.
26. Graumann K, Wittliff J L, Raffelsberger W, Miles L, Jungbauer A & Butt T R 1996 Structural and functional analysis of N-terminal point mutants of the human estrogen receptor. *Journal of Steroid Biochemistry and Molecular Biology* 57 293–300.
27. Sikorski R S & Hieter P 1989 A system of shuttle vectors and yeast host strains designed for efficient manipulation of DNA in *Saccharomyces cerevisiae*. *Genetics* 122 19–27.
28. Butt T R & Chen D J 1999 Reconstruction of mammalian nuclear receptor function in *Saccharomyces cerevisiae*. In Manual of Industrial Microbiology and Biotechnology, 2nd Edition, Section V, pp 527–538. Eds. J Davies & C Harshberger American Society for Microbiology, Washington, D.C.
29. Bachmair A, Finley D & Varshavsky A 1986 In vivo half-life of a protein is a function of its amino-terminal residue. *Science* 234 179–186.

30. Lyttle C R, Damian-Matsumura P, Juul H, Butt T R. Human estrogen receptor regulation in a yeast model system and studies on receptor agonists and antagonists. J Steroid Biochem Mol Biol 1992 42:677–85
31. Graumann K, Wittliff J L, Raffelsberger W, Miles L, Jungbauer A, Butt T R. 1996 Structural and functional analysis of N-terminal point mutants of the human estrogen receptor. J Steroid Biochem Mol Biol 57:293–300.
32. Jefferson R A, Burgess S M, Hirsh D. 1986. beta-Glucuronidase from *Escherichia coli* as a gene-fusion marker. Proc Natl Acad Sci USA 22: 8447–51.
33. Mumberg D, Muller R, Funk M. Yeast vectors for the controlled expression of heterologous proteins in different genetic backgrounds. Gene Apr. 14, 1995;156:119–122.
34. Tran H T, Askari H B, Shaaban S, Price L, Palli S R, Dhadialla T S, Carlson G R and Butt T R. 2001. Reconstruction of Ligand-Dependent Transactivation of *Choristoneura fumiferana* Ecdysone Receptor in Yeast. Molecular Endocrinology 15: 1140–1153.
35. Russell W M, Klaenhammer R T. Identification and cloning of gusA, encoding a new β-glucuronidase from Lactobacillus gasseri ADH. 2001 Appl. Environ. Microbiol. 67: 1253–1267.
36. Kim K I, Beak S H, Jeon Y J, Nishimori S, Suzuki T, Uchida S, Shimbara N, Saitoh H, Tanaka K, Chung C H. A new SUMO-1 specific protease, SUSP1, that is highly expressed in reproductive organs. J of Biol Chem 2000, 19: 14102–6
37. Yeh E T, Gong L, Kamitani T, 2000 Ubiquitin-like proteins: new wines in new bottles. Gene 248: 1–14
38. Li S J, Hochstrasser M. 2000. The yeast ULP2 (SMT4) gene encodes a novel protease specific for the ubiquitin-like Smt3 protein. Mol Cell Biol 20: 2367–77
39. Suzuki T, Ichiyama A) Saitoh H, Kawakami T, Omata M, Chung C H, Kimura M, Shimbara N, and Tanaka K. 1999. A new 30 kDa ubiquitin-related SUMO-1 hydrolase from bovine brain. J Biol Chem 274: 31131–4
40. Schwienhorst I, Johnson E S, Dohmen R J 2000. SUMO conjugation and de-conjugation. Mol Gen Genet. 263: 771–86
41. Mahajan R, Delphin, C, Guan T, Gerace, L and Melchior F. 1997. A small ubiquitin-related polypeptide involved in targeting RanGAP1 to nuclear pore complex protein PanBP2. Cell 88: 97–107

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An estrogen dependent transactivation system for gender-sorting in an avian test animal, comprising;
    a) a first DNA construct comprising a nucleic acid molecule encoding an estrogen receptor having specific binding affinity for said estrogen operably linked to a promoter;
    b) a second DNA construct comprising a promoter containing a plurality of estrogen response elements, said promoter containing a plurality of estrogen response elements being operably linked to a reporter gene;
    c) a third DNA construct comprising a nucleic acid sequence encoding a secreted fusion protein comprising beta-glucuronidase and ubiquitin for cleaving an estrogen glucuronide said estrogen glucuronide comprising said estrogen, said nucleic acid sequence encoding said fusion protein being operably linked to a promoter sequence; and
    d) a host cell comprising said first, second and third DNA constructs, wherein expression of said reporter gene in said host cell is dependent upon cleavage of said estrogen from said estrogen glucuronide present in a biological sample isolated from said avian test animal, reporter gene expression being indicative of the presence of an estrogen which indicates the sex of said avian test animal.

2. The system as claimed in claim 1, wherein said estrogen receptor is selected from the group consisting of estrogen receptor alpha and estrogen receptor beta.

3. The system as claimed in claim 1 wherein said avian test animal is selected from the group consisting of chickens and turkeys.

4. The system as claimed in claim 1, wherein said estrogen glucuronide is selected from the group of conjugates consisting of estrone glucuronide and estradiol 17-beta-glucuronide.

5. The system as claimed in claim 1, wherein cleavage of said estrogen glucuronide releases an estrogen selected from the group consisting of 17-beta-estradiol and estrone.

6. The system as claimed in claim 1, wherein at least one of said promoters in said DNA constructs of parts a), b) and c) is an inducible promoter selected from the group consisting of CUP1, HSP70, HSP26, HSP104, SSA4, galactose-inducible promoters, GAL1, and GAL10.

7. The system as claimed in claim 1 wherein at least one of said promoters in said DNA constructs of parts a), b) and c), is a constitutive promoter selected from the group consisting of ADH1, and GPD.

8. The system as claimed in claim 1, wherein said first, second and third DNA constructs are expression vectors, wherein each of said expression vectors comprises sequences which enable replication of said expression vectors in both prokaryotes and eukaryotes.

9. The system as claimed in claim 1, wherein said host cell is selected from the group consisting of a yeast cell, an insect cell, a mammalian cell, and a bacterial cell.

10. The system as claimed in claim 9, wherein said yeast cell is *Saccharomyces cerevisiae*.

11. The system as claimed in claim 1, wherein said reporter gene is selected from the group consisting of β-galactosidase, alkaline phosphatase, green fluorescent protein, red fluorescent protein, chloramphenicol acetyltransferase, and surface molecules recognized by immunospecific antibodies.

12. The system as claimed in claim 1, wherein said biological sample is selected from the group consisting of allantoic fluid, blood, urinates, saliva, culture media of the avian test animal tissue and extract from the avian test animal tissue.

13. A method for detecting the presence of an estrogen in an avian biological sample, comprising:
    a) providing a host cell containing a first DNA construct having a nucleic acid molecule encoding an estrogen receptor operably linked to a first promoter; a second DNA construct comprising a second promoter containing a plurality of estrogen response elements, said second promoter being operably linked to a reporter gene; and a third DNA construct comprising a nucleic acid sequence encoding a secreted fusion protein comprising beta-glucuronidase and ubiquitin for cleaving an estrogen glucuronide said estrogen glucuronide comprising said estrogen, said nucleic acid sequence encoding said fusion protein being operably linked to a third promoter sequence;

b) contacting said host cell with said avian biological sample suspected of containing estrogen; and c) assessing levels of expression of said reporter gene in said host cell, said level of expression being dependent upon cleavage of said estrogen from said estrogen glucuronide conjugate, if present, in said avian biological sample.

14. The method as claimed in claim 13, wherein said estrogen receptor is selected from the group consisting of estrogen receptor alpha and estrogen receptor beta.

15. The method as claimed in claim 13, wherein said estrogen glucuronide is selected from the group of conjugates consisting of estrone glucuronide and estradiol 17-beta-glucuronide.

16. The method as claimed in claim 13, wherein cleavage of said estrogen glucuronide releases an estrogen selected from the group consisting of 17-beta-estradiol and estrone.

17. The method as claimed in claim 13, wherein at least one of said promoters in said DNA constructs of step a) is an inducible promoter selected from the group consisting of CUP1, HSP70, HSP26, HSP104, SSA4, galactose-inducible promoters, GAL1 and GAL10.

18. The method as claimed in claim 13, wherein at least one of said promoters in said DNA constructs of step a) is a constitutive promoter selected from the group consisting of ADH1 and GPD.

19. The method as claimed in claim 13, wherein said first, second and third DNA constructs are expression vectors, wherein each of said expression vectors comprises sequences which enable replication of said expression vectors in both prokaryotes and eukaryotes.

20. The method as claimed in claim 13, wherein said host cell is selected from the group consisting of a yeast cell, an insect cell, a mammalian cell, and a bacterial cell.

21. The method as claimed in claim 20, wherein said yeast cell is *Saccharomyces cerevisiae*.

22. The method as claimed in claim 13, wherein said reporter gene is selected from the group consisting of β-galactosidase, alkaline phosphatase, green fluorescent protein, red fluorescent protein, chloramphenicol acetyltransferase, and surface molecules recognized by immunospecific antibodies.

23. The method as claimed in claim 13, wherein said biological sample is selected from the group consisting of allantoic fluid, blood, urinates, saliva, culture media of avian test animal tissue, and extract from avian test animal tissue.

24. The method as claimed in claim 13, wherein the level of expression of said reporter is assessed using a method selected from the group consisting of determination of enzymatic activity using enzymatic substrates and detection of protein encoded by said reporter gene using an antibody immunologically specific for said protein encoded by said reporter gene.

25. The method as claimed in claim 13, wherein said reporter gene encodes a fluorescent reporter protein.

26. A kit comprising the test system of claim 1.

27. An estrogen dependent transactivation system for gender-sorting in avian species, comprising;

a) a first DNA construct comprising a nucleic acid molecule encoding an estrogen receptor operably linked to a promoter;

b) a second DNA construct comprising a promoter containing a plurality of estrogen response elements, said promoter containing a plurality of estrogen response elements being operably linked to a reporter gene;

c) a third DNA construct comprising a nucleic acid sequence encoding a secreted fusion protein comprising beta-glucuronidase and ubiquitin for cleaving a naturally occurring estrogen-glucuronide conjugate, said estrogen-glucuronide conjugate comprising estrogen, said nucleic sequence encoding said fusion protein being operably linked to a promoter sequence;

d) a yeast cell comprising said first, second and third DNA constructs, wherein expression of said reporter gene in said yeast cell is dependent upon release of estrogen from said estrogen-glucuronide conjugate present in an allantoic sample of said avian, reporter gene expression levels being correlated with the presence of said estrogen which indicates a sex of said avian;

e) media for yeast cell growth and enhancement of the glucuronidase-ubiquitin fusion protein expression, secretion and activity; and f) a substrate and protocol to assess said reporter gene expression.

28. A method for detecting the presence of estrogen in a ligand-dependent manner in a biological sample, comprising:

a) providing a yeast cell comprising a first DNA construct having a nucleic acid molecule encoding an estrogen receptor operably linked to a first promoter; a second DNA construct comprising a second promoter containing a plurality of estrogen response elements, said second promoter being operably linked to a reporter gene; and a third DNA construct comprising a nucleic acid sequence encoding a secreted fusion protein comprising glucuronidase and ubiquitin for cleaving naturally occurring estrogen-glucuronide conjugates, said nucleic acid sequence encoding said fusion protein being operably linked to a promoter sequence;

b) contacting said yeast cell with a biological sample of an animal suspected of containing estrogen; and c) assessing levels of expression of said reporter gene in said yeast cell, expression of said reporter gene being dependent upon release of estrogen from said estrogen-glucuronide conjugate present in said biological sample, reporter gene expression levels being correlated with the presence of estrogen in said biological sample.

29. The method of claim 28, wherein said biological sample is selected from the group consisting of allantoic fluid, blood, urinates, saliva, culture media of test animal tissue, and extract from test animal tissue.

* * * * *

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
gctcgagagc acagatgctt cgttg                                         25

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gcaaagcttg gagttgattg tatgc                                         25

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
accaagctta ttcgaaggat ccaaacgatg ag                                 32

<210> SEQ ID NO 4
<211> LENGTH: 31
<212> TYPE: DNA
<213> ORGANISM: Artificial Sequence
<220> FEATURE:
<223> OTHER INFORMATION: primer
```

```
<400> SEQUENCE: 4
gccaagcttg gagcctctct tttctcgaga g                                    31

<210> SEQ ID NO 5
<211> LENGTH: 53
<212> TYPE: DNA
<213> ORGANISM: Artificial Sequence
<220> FEATURE:
<223> OTHER INFORMATION: primer

<400> SEQUENCE: 5
gcgtcgactc tggtcacagt gaccggtcac agtgacctta tggaagcacc aag            53

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gtggatccca tgattattgt tttg                                            24

<210> SEQ ID NO 7
<211> LENGTH: 9877
<212> TYPE: DNA
<213> ORGANISM: Artificial Sequence
<220> FEATURE:
<223> OTHER INFORMATION: CyC1 based estrogen inducible reporter YRpE2

<400> SEQUENCE: 7
gaattctgaa ccagtcctaa aacgagtaaa taggaccggc aattcttcaa gcaataaaca     60
ggaataccaa ttattaaaag ataacttagt cagatcgtac aataaagctt tgaagaaaaa    120
tgcgccttat tcaatctttg ctataaaaaa tggcccaaaa tctcacattg gaagacattt    180
gatgacctca tttctttcaa tgaagggcct aacggagttg actaatgttg tgggaaattg    240
gagcgataag cgtgcttctg ccgtggccag gacaacgtat actcatcaga taacagcaat    300
acctgatcac tacttcgcac tagtttctcg gtactatgca tatgatccaa tatcaaagga    360
aatgatagca ttgaaggatg agactaatcc aattgaggag tggcagcata tagaacagct    420
aaagggtagt gctgaaggaa gcatacgata ccccgcatgg aatgggataa tatcacagga    480
ggtactagac tacctttcat cctacataaa tagacgcata taagtacgca tttaagcata    540
aacacgcact atgccgttct tctcatgtat atatatatac aggcaacacg cagatatagg    600
tgcgacgtga acagtgagct gtatgtgcgc agctcgcgtt gcattttcgg aagcgctcgt    660
tttcggaaac gctttgaagt tcctattccg aagttcctat tctctagaaa gtataggaac    720
ttcagagcgc ttttgaaaac caaaagcgct ctgaagacgc actttcaaaa accaaaaac    780 gcaccggact gtaacgagct actaaaatat tgcgaatacc gcttccacaa acattgctca    840
aaagtatctc tttgctatat atctctgtgc tatatccta tataacctac ccatccacct    900
ttcgctcctt gaacttgcat ctaaactcga cctctcacatc ttttatgttt atctctagta    960
ttactcttta gacaaaaaaa ttgtagtaag aactattcat agagtgaatc gaaaacaata   1020
cgaaaatgta acatttcct atacgtagta tatagagaca aaatagaaga aaccgttcat   1080
aattttctga ccaatgaaga atcatcaacg ctatcacttt ctgttcacaa agtatgcgca   1140
atccacatcg gtatagaata taatcgggga tgcctttatc ttgaaaaaat gcacccgcag   1200
cttcgctagt aatcagtaaa cgcgggaagt ggagtcaggc ttttttttatg aagagaaaa   1260
```

-continued

```
tagacaccaa agtagccttc ttctaacctt aacggaccta cagtgcaaaa agttatcaag      1320
agactgcatt atagagcgca caaaggagaa aaaaagtaat ctaagatgct ttgttagaaa      1380
aatagcgctc tcgggatgca ttttttgtaga acaaaaaaga agtatagatt ctttgttggt    1440
aaaatagcgc tctcgcgttg catttctgtt ctgtaaaaat gcagctcaga ttctttgttt     1500
gaaaaattag cgctctcgcg ttgcattttt gttttacaaa aatgaagcac agattcttcg     1560
ttggtaaaat agcgctttcg cgttgcattt ctgttctgta aaaatgcagc tcagattctt     1620
tgtttgaaaa attagcgctc tcgcgttgca ttttttgttct acaaaatgaa gcacagatgc    1680
ttcgttaaca aagatatgct attgaagtgc aagatgaaa cgcagaaaat gaaccgggga      1740
tgcgacgtgc aagattacct atgcaataga tgcaatagtt tctccaggaa ccgaaataca    1800
tacattgtct tccgtaaagc gctagactat atattattat acaggttcaa atatactatc    1860
tgtttcaggg aaaactccca ggttcggatg ttcaaaattc aatgatgggt aacaagtacg    1920
atcgtaaatc tgtaaaacag tttgtcggat attaggctgt atctcctcaa agcgtattcg    1980
aatatcattg agaagctgca gcgtcacatc ggataataat gatggcagcc attgtagaag   2040
tgccttttgc atttctagtc tctttctcgg tctagctagt tttactacat cgcgaagata   2100
gaatcttaga tcacactgcc tttgctgagc tggatcaata gagtaacaaa agagtggtaa   2160
ggcctcgtta aaggacaagg acctgagcgg aagtgtatcg tacagtagac ggagtatact   2220
agtatagtct atagtccgtg gaattctcat gtttgacagc ttatcatcga taagcttgct   2280
tttcaattca tctttttttt ttttgttctt tttttttgatt ccggtttctt tgaaattttt    2340
ttgattcggt aatctccgag cagaaggaag aacgaaggaa ggagcacaga cttagattgg    2400
tatatatacg catatgtggt gttgaagaaa catgaaattg cccagtattc ttaacccaac   2460
tgcacagaac aaaaacctgc aggaaacgaa gataaatcat gtcgaaagct acatataagg   2520
aacgtgctgc tactcatcct agtcctgttg ctgccaagct atttaatatc atgcacgaaa    2580
agcaaacaaa cttgtgtgct tcattggatg ttcgtaccac caaggaatta ctggagttag    2640
ttgaagcatt aggtcccaaa atttgtttac taaaaacaca tgtggatatc ttgactgatt   2700
tttccatgga gggcacagtt aagccgctaa aggcattatc cgccaagtac aattttttac    2760
tcttcgaaga cagaaaattt gctgacattg taatacagt caaattgcag tactctgcgg     2820
gtgtatacag aatagcagaa tgggcagaca ttacgaatgc acacggtgtg gtgggcccag   2880
gtattgttag cggtttgaag caggcggcgg aagaagtaac aaaggaacct agaggccttt   2940
tgatgttagc agaattgtca tgcaagggct ccctagctac tggagaatat actaagggta   3000
ctgttgacat tgcgaagagc gacaaagatt ttgttatcgg ctttattgct caaagagaca   3060
tgggtggaag agatgaaggt tacgattggt tgattatgac acccggtgtg ggtttagatg   3120
acaagggaga cgcattgggt caacagtata gaaccgtgga tgatgtggtc tctacaggat   3180
ctgacattat tattgttgga agaggactat ttgcaaaggg aagggatgct aagtagagg    3240 gtgaacgtta cagaaaagca ggctgggaag catatttgag aagatgcggc cagcaaaact   3300
aaaaaactgt attataagta aatgcatgta tactaaactc acaaattaga gcttcaattt   3360
aattatatca gttattaccc gatcaaaaat catcgcttcg ctgattaatt accccagaaa   3420
taaggctaaa aaactaatcg cattatcatc ctatggttgt taatttgatt cgttcatttg   3480
aaggtttgtg gggccaggtt actgccaatt tttcctcttc ataaccataa aagctagtat   3540
tgtagaatct ttattgttcg gagcagtgcg gcgcgaggca catctgcgtt tcaggaacgc   3600
gaccggtgaa gacgaggacg cacggaggag agtcttcctt cggagggctg tcacccgctc   3660
```

```
ggcggcttct aatccgtact tcaatatagc aatgagcagt taagcgtatt actgaaagtt    3720
ccaaagagaa ggtttttta ggctaatcga cgtcgacaat cttacatggt ctacctttga    3780
tgacaacgaa accattcttt ctcaaggcag aacattgcat tgggtaggtg gcggaggcac    3840
cagcgtcagc attttcaaag gtgtgttctt cgtcagacat gttttagtgt gtgaatgaaa    3900
taggtgtatg ttttcttttt gctagacaat aattaggaac aaggtaaggg aactaaagtg    3960
tagaataaga ttaaaaaaga agaacaagtt gaaaaggcaa gttgaaattt caagaaaaaa    4020
gtcaattgaa gtacagtaaa ttgacctgaa tatatctgag ttccgacaac aatgagttta    4080
ccaaagagaa caatggaata ggaaactttg aacgaagaaa ggaaagcagg aaaggaaaaa    4140
attttaggc tcgaggtcca aagtcaggtc acagtgacct gatcaaagtt ctcgaggtcc    4200
aaagtcaggt cacagtgacc tgatcaaagt tctcgagcag atccgccagg cgtgtatata    4260
gcgtggatgg ccaggcaact ttagtgctga cacatacagg catatatata tgtgtgcgac    4320
gacacatgat catatggcat gcatgtgctc tgtatgtata taaaactctt gttttcttct    4380
tttctctaaa tattctttcc ttatacatta ggtcctttgt agcataaatt actatacttc    4440
tatagacacg caaacacaaa tacacacact aaattaataa tgaccggatc cggagcttgg    4500
ctgttgcccg tctcactggt gaaagaaaa accaccctgg cgcccaatac gcaaaccgcc    4560
tctccccgcg cgttggccga ttcattaatg cagctggcac gacaggtttc ccgacttaat    4620
cgccttgcag cacatccccc tttcgccagc tggcgtaata gcgaagaggc ccgcaccgat    4680
cgcccttccc aacagttgcg cagcctgaat ggcgaatggc gctttgcctg gtttccggca    4740
ccagaagcgg tgccggaaag ctggctggag tgcgatcttc ctgaggccga tactgtcgtc    4800
gtcccctcaa actggcagat gcacggttac gatgcgccca tctacaccaa cgtaacctat    4860
cccattacgg tcaatccgcc gtttgttccc acggagaatc cgacgggttg ttactcgctc    4920
acatttaatg ttgatgaaag ctggctacag gaaggccaga cgcgaattat ttttgatggc    4980
gttaactcgg cgtttcatct gtggtgcaac gggcgctggg tcggttacgg ccaggacagt    5040
cgtttgccgt ctgaatttga cctgagcgca ttttacgcg ccggagaaaa ccgcctcgcg    5100
gtgatggtgc tgcgttggag tgacggcagt tatctggaag atcaggatat gtggcggatg    5160
agcggcattt tccgtgacgt ctcgttgctg cataaaccga ctacacaaat cagcgatttc    5220
catgttgcca ctcgctttaa tgatgatttc agccgcgctg tactggaggc tgaagttcag    5280
atgtgcggcg agttgcgtga ctacctacgg gtaacagttt cttatggca gggtgaaacg    5340
caggtcgcca gcggcaccgc gccttcggc ggtgaaatta tcgatgagcg tggtggttat    5400
gccgatcgcg tcacactacg tctgaacgtc gaaaacccga aactgtggag cgccgaaatc    5460
ccgaatctct atcgtgcggt ggttgaactg cacaccgccg acggcacgct gattgaagca    5520
gaagcctgcg atgtcggttt ccgcgaggtg cggattgaaa atggtctgct gctgctgaac    5580
ggcaagccgt tgctgattcg aggcgttaac cgtcacgagc atcatcctct gcatggtcag    5640
gtcatggatg agcagacgat ggtgcaggat atcctgctga tgaagcagaa caactttaac    5700
gccgtgcgct gttcgcatta tccgaaccat ccgctgtggt acacgctgtg cgaccgctac    5760
ggcctgtatg tggtggatga agccaatatt gaaacccacg gcatggtgcc aatgaatcgt    5820
ctgaccgatg atccgcgctg ctaccgggcg atgagcgaac gcgtaacgcg aatggtgcag    5880
cgcgatcgta atcacccgag tgtgatcatc tggtcgctgg ggaatgaatc aggccacggc    5940
gctaatcacg acgcgctgta tcgctggatc aaatctgtcg atccttcccg cccggtgcag    6000
tatgaaggcg gcggagccga caccacggcc accgatatta tttgcccgat gtacgcgcgc    6060
```

```
gtggatgaag accagccctt cccggctgtg ccgaaatggt ccatcaaaaa atggctttcg    6120
ctacctggag agacgcgccc gctgatcctt tgcgaatacg cccacgcgat gggtaacagt    6180
cttggcggtt tcgctaaata ctggcaggcg tttcgtcagt atccccgttt acagggcggc    6240
ttcgtctggg actgggtgga tcagtcgctg attaaatatg atgaaaacgg caacccgtgg    6300
tcggcttacg gcggtgattt tggcgatacg ccgaacgatc gccagttctg tatgaacggt    6360
ctggtctttg ccgaccgcac gccgcatcca gcgctgacgg aagcaaaaca ccagcagcag    6420
tttttccagt tccgtttatc cgggcaaacc atcgaagtga ccagcgaata cctgttccgt    6480
catagcgata acgagctcct gcactggatg gtggcgctgg atggtaagcc gctggcaagc    6540
ggtgaagtgc ctctggatgt cgctccacaa ggtaaacagt tgattgaact gcctgaacta    6600
ccgcagccgg agagcgccgg gcaactctgg ctcacagtac gcgtagtgca accgaacgcg    6660
accgcatggt cagaagccgg gcacatcagc gcctggcagc agtggcgtct ggcggaaaac    6720
ctcagtgtga cgctcccccgc cgcgtcccac gccatcccgc atctgaccac cagcgaaatg    6780
```

-continued

```
gaagtggtgg cctaactacg gctacactag aaggacagta tttggtatct gcgctctgct    8520
gaagccagtt accttcggaa aaagagttgg tagctcttga tccggcaaac aaaccaccgc    8580
tggtagcggt ggtttttttg tttgcaagca gcagattacg cgcagaaaaa aaggatctca    8640
agaagatcct ttgatctttt ctacggggtc tgacgctcag tggaacgaaa actcacgtta    8700
agggattttg gtcatgagat tatcaaaaag gatcttcacc tagatccttt taaattaaaa    8760
atgaagtttt aaatcaatct aaagtatata tgagtaaact tggtctgaca gttaccaatg    8820
cttaatcagt gaggcaccta tctcagcgat ctgtctattt cgttcatcca tagttgcctg    8880
actccccgtc gtgtagataa ctacgatacg ggagggctta ccatctggcc ccagtgctgc    8940
aatgataccg cgagacccac gctcaccggc tccagattta tcagcaataa accagccagc    9000
cggaagggcc gagcgcagaa gtggtcctgc aactttatcc gcctccatcc agtctattaa    9060
ttgttgccgg gaagctagag taagtagttc gccagttaat agtttgcgca acgttgttgc    9120
cattgctgca ggcatcgtgg tgtcacgctc gtcgtttggt atggcttcat tcagctccgg    9180
ttcccaacga tcaaggcgag ttacatgatc ccccatgttg tgcaaaaaag cggttagctc    9240
cttcggtcct ccgatcgttg tcagaagtaa gttggccgca gtgttatcac tcatggttat    9300
ggcagcactg cataattctc ttactgtcat gccatccgta agatgctttt ctgtgactgg    9360
tgagtactca accaagtcat tctgagaata gtgtatgcgg cgaccgagtt gctcttgccc    9420
ggcgtcaaca cgggataata ccgcgccaca tagcagaact ttaaaagtgc tcatcattgg    9480
aaaacgttct cggggcgaaa actctcaag gatcttaccg ctgttgagat ccagttcgat    9540
gtaacccact cgtgcaccca actgatcttc agcatctttt actttcacca gcgtttctgg    9600
gtgagcaaaa acaggaaggc aaaatgccgc aaaaaaggga ataagggcga cacggaaatg    9660
ttgaatactc atactcttcc ttttcaata ttattgaagc atttatcagg gttattgtct    9720
catgagcgga tacatatttg aatgtattta gaaaaataaa caaatagggg ttccgcgcac    9780
atttccccga aaagtgccac ctgacgtcta agaaaccatt attatcatga cattaaccta    9840
taaaaatagg cgtatcacga ggccctttcg tcttcaa                             9877
```

<210> SEQ ID NO 8
<211> LENGTH: 9098
<212> TYPE: DNA
<213> ORGANISM: Artificial Sequence
<220> FEATURE:
<223> OTHER INFORMATION: SSA4-based estrogen inducible reporter
      YRpE2SSA4-lacZ

<400> SEQUENCE: 8

```
gaattctgaa ccagtcctaa aacgagtaaa taggaccggc aattcttcaa gcaataaaca      60
ggaataccaa ttattaaaag ataacttagt cagatcgtac aataaagctt tgaagaaaaa     120
tgcgccttat tcaatctttg ctataaaaaa tggcccaaaa tctcacattg gaagacattt     180
gatgacctca tttctttcaa tgaagggcct aacggagttg actaatgttg tgggaaattg     240
gagcgataag cgtgcttctg ccgtggccag gacaacgtat actcatcaga taacagcaat     300
acctgatcac tacttcgcac tagtttctcg gtactatgca tatgatccaa tatcaaagga     360
aatgatagca ttgaaggatg agactaatcc aattgaggag tggcagcata tagaacagct     420
aaagggtagt gctgaaggaa gcatacgata ccccgcatgg aatgggataa tatcacagga     480
ggtactagac taccttttcat cctacataaa tagacgcata taagtacgca tttaagcata     540
aacacgcact atgccgttct tctcatgtat atatatatac aggcaacacg cagatatagg     600
```

```
tgcgacgtga acagtgagct gtatgtgcgc agctcgcgtt gcattttcgg aagcgctcgt    660
tttcggaaac gctttgaagt tcctattccg aagttcctat tctctagaaa gtataggaac    720
ttcagagcgc ttttgaaaac caaaagcgct ctgaagacgc actttcaaaa aaccaaaaac    780
gcaccggact gtaacgagct actaaaatat tgcgaatacc gcttccacaa acattgctca    840
aaagtatctc tttgctatat atctctgtgc tatatcccta taaacctac ccatccacct     900
ttcgctcctt gaacttgcat ctaaactcga cctctacatt ttttatgttt atctctagta    960
ttactcttta gacaaaaaaa ttgtagtaag aactattcat agagtgaatc gaaaacaata   1020
cgaaaatgta aacatttcct atacgtagta tatagagaca aaatagaaga aaccgttcat   1080
aattttctga ccaatgaaga atcatcaacg ctatcacttt ctgttcacaa agtatgcgca   1140
atccacatcg gtatagaata taatcgggga tgcctttatc ttgaaaaaat gcacccgcag   1200
cttcgctagt aatcagtaaa cgcgggaagt ggagtcaggc ttttttatg gaagagaaaa    1260
tagacaccaa agtagccttc ttctaacctt aacggaccta cagtgcaaaa agttatcaag   1320
agactgcatt atagagcgca caaggagaa aaaagtaat ctaagatgct tgttagaaa      1380
aatagcgctc tcgggatgca ttttgtaga acaaaaaaga agtatagatt ctttgttggt    1440
aaaatagcgc tctcgcgttg catttctgtt ctgtaaaaat gcagctcaga ttctttgttt    1500
gaaaaattag cgctctcgcg ttgcattttt gttttacaaa aatgaagcac agattcttcg   1560
ttggtaaaat agcgctttcg cgttgcattt ctgttctgta aaatgcagc tcagattctt    1620
tgtttgaaaa attagcgctc tcgcgttgca ttttgttct acaaaatgaa gcacagatgc   1680
ttcgttaaca agatatgct attgaagtgc aagatggaaa cgcagaaaat gaaccgggga    1740
tgcgacgtgc aagattacct atgcaataga tgcaatagtt tctccaggaa ccgaaataca   1800
tacattgtct tccgtaaagc gctagactat atattattat acaggttcaa atatactatc   1860
tgtttcaggg aaaactccca ggttcggatg ttcaaaattc aatgatgggt aacaagtacg   1920
atcgtaaatc tgtaaaacag tttgtcggat attaggctgt atctcctcaa agcgtattcg   1980
aatatcattg agaagctgca gcgtcacatc ggataataat gatggcagcc attgtagaag   2040
tgccttttgc atttctagtc tctttctcgg tctagctagt tttactacat cgcgaagata   2100
gaatcttaga tcacactgcc tttgctgagc tggatcaata gagtaacaaa agagtggtaa   2160
ggcctcgtta aaggacaagg acctgagcgg aagtgtatcg tacagtagac ggagtatact   2220
agtatagtct atagtccgtg gaattctcat gtttgacagc ttatcatcga taagcttttc   2280
aattcaattc atcattttt ttttattctt tttttgatt tcggtttctt tgaaatttt     2340
ttgattcggt aatctccgaa cagaaggaag aacgaaggaa ggagcacaga cttagattgg   2400
tatatatacg catatgtagt gttgaagaaa catgaaattg cccagtattc ttaacccaac   2460
tgcacagaac aaaaacctgc aggaaacgaa gataaatcat gtcgaaagct acatataagg   2520
aacgtgctgc tactcatcct agtcctgttg ctgccaagct atttaatatc atgcacgaaa   2580
agcaaacaaa cttgtgtgct tcattggatg ttcgtaccac caaggaatta ctggagttag   2640
ttgaagcatt aggtcccaaa atttgtttac taaaaacaca tgtggatatc ttgactgatt   2700
tttccatgga gggcacagtt aagccgctaa aggcattatc cgccaagtac aatttttac    2760
tcttcgaaga cagaaaattt gctgacattg gtaaatacagt caaattgcag tactctgcgg   2820
gtgtatacag aatagcagaa tgggcagaca ttacgaatgc acacggtgtg gtgggcccag   2880
gtattgttag cggtttgaag caggcggcag aagaagtaac aaaggaacct agaggccttt   2940
tgatgttagc agaattgtca tgcaagggct ccctatctac tggagaatat actaagggta   3000
```

-continued

```
ctgttgacat tgcgaagagc gacaaagatt ttgttatcgg ctttattgct caaagagaca      3060
tgggtggaag agatgaaggt tacgattggt tgattatgac acccggtgtg ggtttagatg      3120
acaagggaga cgcattgggt caacagtata gaaccgtgga tgatgtggtc tctacaggat      3180
ctgacattat tattgttgga agaggactat ttgcaaaggg aagggatgct aaggtagagg      3240
gtgaacgtta cagaaaagca ggctgggaag catatttgag aagatgcggc cagcaaaact      3300
aaaaaactgt attataagta aatgcatgta tactaaactc acaaattaga gcttcaattt      3360
aattatatca gttattaccc tcgacctcga aattcctgca ggatatctgg atcgatccac      3420
aagcttgcat gcctgcaggt cgactctggt cacagtgacc ggtcacagtg accttatgga      3480
agcaccaaga aaaaggaag ttaaacaaaa cactgattca ataagcaagg ggggaagctc      3540
cttagtttga cgacagtaac aaaatgttcg tataaattga acgaaactca agccaataaa      3600
ggacttttca gaggcctatc tcttctttct ccacaacttt cgaataaaaa ccactaataa      3660
aaagtaaata acaaaaacaa gaaaaaaaat aaacaaaaca ataatcatgg gatccaccat      3720
gattacggat tcactggccg tcgttttaca acgtcgtgac tgggaaaacc ctggcgttac      3780
ccaacttaat cgccttgcag cacatccccc tttcgccagc tggcgtaata gcgaagaggc      3840
ccgcaccgat cgcccttccc aacagttgcg cagcctgaat ggcgaatggc gctttgcctg      3900
gtttccggca ccagaagcgg tgccggaaag ctggctggag tgcgatcttc ctgaggccga      3960
tactgtcgtc gtcccctcaa actggcagat gcacggttac gatgcgccca tctacaccaa      4020
cgtaacctat cccattacgg tcaatccgcc gtttgttccc acggagaatc cgacgggttg      4080
ttactcgctc acatttaatg ttgatgaaag ctggctacag gaaggccaga cgcgaattat      4140
ttttgatggc gttaactcgg cgtttcatct gtggtgcaac gggcgctggg tcggttacgg      4200
ccaggacagt cgtttgccgt ctgaatttga cctgagcgca ttttttacgcg ccggagaaaa      4260 ccgcctcgcg gtgatggtgc tgcgttggag tgacggcagt tatctggaag atcaggatat      4320
gtggcggatg agcggcattt tccgtgacgt ctcgttgctg cataaaccga ctacacaaat      4380
cagcgatttc catgttgcca ctcgctttaa tgatgatttc agccgcgctg tactggaggc      4440
tgaagttcag atgtgcggcg agttgcgtga ctacctacgg gtaacagttt ctttatggca      4500
gggtgaaacg caggtcgcca gcggcaccgc gcctttcggc ggtgaaatta tcgatgagcg      4560
tggtggttat gccgatcgcg tcacactacg tctgaacgtc gaaaacccga actgtggag       4620 cgccgaaatc ccgaatctct atcgtgcggt ggttgaactg cacaccgccg acggcacgct      4680
gattgaagca gaagcctgcg atgtcggttt ccgcgaggtg cggattgaaa atggtctgct      4740
gctgctgaac ggcaagccgt tgctgattcg aggcgttaac cgtcacgagc atcatcctct      4800
gcatggtcag gtcatggatg agcagacgat ggtgcaggat atcctgctga tgaagcagaa      4860
caactttaac gccgtgcgct gttcgcatta tccgaaccat cgctgtggt acacgctgtg      4920 cgaccgctac ggcctgtatg tggtggatga agccaatatt gaaacccacg gcatggtgcc      4980
aatgaatcgt ctgaccgatg atccgcgctg gctaccggcg atgagcgaac gcgtaacgcg      5040
aatggtgcag cgcgatcgta atcacccgag tgtgatcatc tggtcgctgg ggaatgaatc      5100
aggccacggc gctaatcacg acgcgctgta tcgctggatc aaatctgtcg atccttcccg      5160
cccggtgcag tatgaaggcg gcggagccga caccacggcc accgatatta tttgcccgat      5220
gtacgcgcgc gtggatgaag accagccctt cccggctgtg ccgaaatggt ccatcaaaaa      5280
atggctttcg ctacctggag agacgcgccc gctgatcctt tgcgaatacg cccacgcgat      5340
gggtaacagt cttggcggtt tcgctaaata ctggcaggcg tttcgtcagt atccccgttt      5400
```

```
acagggcggc ttcgtctggg actgggtgga tcagtcgctg attaaatatg atgaaaacgg    5460
caacccgtgg tcggcttacg gcggtgattt tggcgatacg ccgaacgatc gccagttctg    5520
tatgaacggt ctggtctttg ccgaccgcac gccgcatcca gcgctgacgg aagcaaaaca    5580
ccagcagcag ttttccagt tccgtttatc cgggcaaacc atcgaagtga ccagcgaata    5640
cctgttccgt catagcgata acgagctcct gcactggatg gtggcgctgg atggtaagcc    5700
gctggcaagc ggtgaagtgc tctggatgt cgctccacaa ggtaaacagt tgattgaact    5760
gcctgaacta ccgcagccgg agagcgccgg gcaactctgg ctcacagtac gcgtagtgca    5820
accgaacgcg accgcatggt cagaagccgg gcacatcagc gcctggcagc agtggcgtct    5880
ggcggaaaac ctcagtgtga cgctccccgc cgcgtcccac gccatcccgc atctgaccac    5940
cagcgaaatg gatttttgca tcgagctggg taataagcgt tggcaattta accgccagtc    6000
aggctttctt tcacagatgt ggattggcga taaaaacaa ctgctgacgc gctgcgcga    6060 tcagttcacc cgtgcaccgc tggataacga cattggcgta agtgaagcga cccgcattga    6120
ccctaacgcc tgggtcgaac gctggaaggc ggcgggccat taccaggccg aagcagcgtt    6180
gttgcagtgc acggcagata cacttgctga tgcggtgctg attacgaccg ctcacgcgtg    6240
gcagcatcag gggaaaaacct tatttatcag ccggaaaacc taccggattg atggtagtgg    6300
tcaaatggcg attaccgttg atgttgaagt ggcgagcgat acaccgcatc cggcgcggat    6360
tggcctgaac tgccagctgg cgcaggtagc agagcgggta aactggctcg gattagggcc    6420
gcaagaaaac tatcccgacc gccttactgc cgcctgtttt gaccgctggg atctgccatt    6480
gtcagacatg tatacccgt acgtcttccc gagcgaaaac ggtctgcgct gcgggacgcg    6540
cgaattgaat tatggcccac accagtggcg cggcgacttc cagttcaaca tcagccgcta    6600
cagtcaacag caactgatgg aaaccagcca tcgccatctg ctgcacgcgg aagaaggcac    6660
atggctgaat atcgacggtt ccatatggg gattggtggc gacgactcct ggagcccgtc    6720
agtatcggcg gaattccagc tgagcgccgg tcgctaccat taccagttgg tctggtgtca    6780 aaataataa taagagctcg aattcgctgc ctcgcgcgtt tcggtgatga cggtgaaaac    6840
ctctgacaca tgcagctccc ggagacggtc acagcttgtc tgtaagcgga tgccgggagc    6900
agacaagccc gtcagggcgc gtcagcgggt gttggcgggt gtcggggcgc agccatgacc    6960
cagtcacgta gcgatagcgg agtgtatact ggcttaacta tgcggcatca gagcagattg    7020
tactgagagt gcaccatatg cggtgtgaaa taccgcacag atgcgtaagg agaaaatacc    7080
gcatcaggcg ctcttccgct tcctcgctca ctgactcgct gcgctcggtc gttcggctgc    7140
ggcgagcggt atcagctcac tcaaaggcgg taatacggtt atccacagaa tcaggggata    7200
acgcaggaaa gaacatgtga gcaaaaggcc agcaaaaggc caggaaccgt aaaaaggccg    7260
cgttgctggc gtttttccat aggctccgcc cccctgacga gcatcacaaa aatcgacgct    7320
caagtcagag gtggcgaaac ccgacaggac tataaagata ccaggcgttt ccccctggaa    7380
gctccctcgt gcgctctcct gttccgaccc tgccgcttac cggatacctg tccgcctttc    7440
tcccttcggg aagcgtggcg ctttctcata gctcacgctg taggtatctc agttcggtgt    7500
aggtcgttcg ctccaagctg ggctgtgtgc acgaaccccc cgttcagccc gaccgctgcg    7560
ccttatccgg taactatcgt cttgagtcca acccggtaag acacgactta tcgccactgg    7620
cagcagccac tggtaacagg attagcagag cgaggtatgt aggcggtgct acagagttct    7680
tgaagtggtg gcctaactac ggctacacta gaaggacagt atttggtatc tgcgctctgc    7740
tgaagccagt taccttcgga aaaagagttg gtagctcttg atccggcaaa caaaccaccg    7800
```

-continued

```
ctggtagcgg tggttttttt gtttgcaagc agcagattac gcgcagaaaa aaaggatctc    7860
aagaagatcc tttgatcttt tctacggggt ctgacgctca gtggaacgaa aactcacgtt    7920
aagggatttt ggtcatgaga ttatcaaaaa ggatcttcac ctagatcctt ttaaattaaa    7980
aatgaagttt taaatcaatc taaagtatat atgagtaaac ttggtctgac agttaccaat    8040
gcttaatcag tgaggcacct atctcagcga tctgtctatt tcgttcatcc atagttgcct    8100
gactccccgt cgtgtagata actacgatac gggagggctt accatctggc cccagtgctg    8160
caatgatacc gcgagaccca cgctcaccgg ctccagattt atcagcaata aaccagccag    8220
ccggaagggc cgagcgcaga agtggtcctg caactttatc cgcctccatc cagtctatta    8280
attgttgccg ggaagctaga gtaagtagtt cgccagttaa tagtttgcgc aacgttgttg    8340
ccattgctgc aggcatcgtg gtgtcacgct cgtcgtttgg tatggcttca ttcagctccg    8400
gttcccaacg atcaaggcga gttacatgat cccccatgtt gtgcaaaaaa gcggttagct    8460
ccttcggtcc tccgatcgtt gtcagaagta agttggccgc agtgttatca ctcatggtta    8520
tggcagcact gcataattct cttactgtca tgccatccgt aagatgcttt tctgtgactg    8580
gtgagtactc aaccaagtca ttctgagaat agtgtatgcg gcgaccgagt tgctcttgcc    8640
cggcgtcaac acgggataat accgcgccac atagcagaac tttaaaagtg ctcatcattg    8700
gaaaacgttc ttcggggcga aaactctcaa ggatcttacc gctgttgaga tccagttcga    8760
tgtaacccac tcgtgcaccc aactgatctt cagcatcttt tactttcacc agcgtttctg    8820
ggtgagcaaa aacaggaagg caaaatgccg caaaaaaggg aataagggcg acacggaaat    8880
gttgaatact catactcttc ctttttcaat attattgaag catttatcag ggttattgtc    8940
tcatgagcgg atacatattt gaatgtattt agaaaaataa acaaataggg gttccgcgca    9000
catttccccg aaaagtgcca cctgacgtct aagaaaccat tattatcatg acattaacct    9060
ataaaaatag gcgtatcacg aggccctttc gtcttcaa                             9098
```

<210> SEQ ID NO 9
<211> LENGTH: 7979
<212> TYPE: DNA
<213> ORGANISM: Artificial Sequence
<220> FEATURE:
<223> OTHER INFORMATION: yeast expression vector for human estrogen receptor alpha

<400> SEQUENCE: 9

```
ggatcccatt accgacattt gggcgctata cgtgcatatg ttcatgtatg tatctgtatt      60
taaaacactt ttgtattatt tttcctcata tatgtgtata ggtttatacg gatgatttaa    120
ttattacttc accacccttt atttcaggct gatatcttag ccttgttact agttagaaaa    180
agacattttt gctgtcagtc actgtcaaga gattcttttg ctggcatttc ttctagaagc    240
aaaaagagcg atgcgtcttt tccgctgaac cgttccagca aaaaagacta ccaacgcaat    300
atggattgtc agaatcatat aaaagagaag caaataactc cttgtcttgt atcaattgca    360
ttataatatc ttcttgttag tgcaatatca tatagaagtc atcgaaatag atattaagaa    420
aaacaaactg taacgaattc attatgcaga tcttcgtcaa gacgttaacc ggtaaaacca    480
taactctaga agttgaatct tccgatacca tcgacaacgt taagtcgaaa attcaagaca    540
aggaaggcat tccacctgat caacaaagat tgatctttgc cggtaagcag ctcgaggacg    600
gtagaacgct gtctgattac aacattcaga aggagtcgac cttacatctt gtcttaagac    660
taagaggtgg tatgaccatg accctccaca ccaaagcatc tgggatggcc ctactgcatc    720
```

-continued

```
agatccaagg gaacgagctg gagcccctga accgtccgca gctcaagatc cccctggagc    780
ggcccctggg cgaggtgtac ctggacagca gcaagcccgc cgtgtacaac taccccgagg    840
gcgccgccta cgagttcaac gccgcggccg ccgccaacgc gcaggtctac ggtcagaccg    900
gcctcccta  cggccccggg tctgaggctg cggcgttcgg ctccaacggc ctgggggtt     960
tcccccact  caacagcgtg tctccgagcc cgctgatgct actgcacccg ccgccgcagc   1020
tgtcgccttt cctgcagccc cacggccagc aggtgcccta ctacctggag aacgagccca   1080
gcggctacac ggtgcgcgag gccggcccgc cggcattcta caggccaaat tcagataatc   1140
gacgccaggg tggcagagaa agattggcca gtaccaatga caagggaagt atggctatgg   1200
aatctgccaa ggagactcgc tactgtgcag tgtgcaatga ctatgcttca ggctaccatt   1260
atggagtctg gtcctgtgag ggctgcaagg ccttcttcaa gagaagtatt caaggacata   1320
acgactatat gtgtccagcc accaaccagt gcaccattga taaaaacagg aggaagagct   1380
gccaggcctg ccggctccgc aaatgctacg aagtgggaat gatgaaaggt gggatacgaa   1440
aagaccgaag aggagggaga atgttgaaac acaagcgcca gagagatgat ggggagggca   1500
ggggtgaagt ggggtctgct ggagacatga gagctgccaa cctttggcca agcccgctca   1560
tgatcaaacg ctctaagaag aacagcctgg ccttgtccct gacggccgac cagatggtca   1620
gtgccttgtt ggatgctgag ccccccatac tctattccga gtatgatcct accagaccct   1680
tcagtgaagc ttcgatgatg ggcttactga ccaacctggc agacagggag ctggttcaca   1740
tgatcaactg ggcgaagagg gtgccaggct ttgtggattt gaccctccat gatcaggtcc   1800
accttctaga atgtgcctgg ctagagatcc tgatgattgg tctcgtctgg cgctccatgg   1860
agcacccagt gaagctactg tttgctccta acttgctctt ggacaggaac cagggaaaat   1920
gtgtagaggg catggtggag atcttcgaca tgctgctggc tacatcatct cggttccgca   1980
tgatgaatct gcaggagagg gagtttgtgt gcctcaaatc tattattttg cttaattctg   2040
gagtgtacac atttctgtcc agcacctga  agtctctgga agagaaggac catatccacc   2100
gagtcctgga caagatcaca gacactttga tccacctgat ggccaaggca ggcctgaccc   2160
tgcagcagca gcaccagcgg ctggcccagc tcctcctcat cctctcccac atcaggcaca   2220
tgagtaacaa aggcatggag catctgtaca gcatgaagtg caagaacgtg gtgcccctct   2280
atgacctgct gctggagatg ctggacgccc accgcctaca tgcgcccact agccgtggag   2340
gggcatccgt ggaggagacg gaccaaagcc acttggccac tgcgggctct acttcatcgc   2400
attccttgca aaagtattac atcacggggg aggcagaggg tttccctgcc acagtctgag   2460
agctccctgg cgaattgtac caagatggcc tttggtgggt tgaagaagga aaaagacaga   2520
aacgacttaa ttacctactt gaaaaaagcc tgtgagtaaa caggccccctt ttcctttgtc   2580
gatatcatgt aattagttat gtcacgctta cattcacgcc ctcccccac  atccgctcta   2640
accgaaaagg aaggagttag acaacctgaa gtctaggtcc ctatttattt ttttatagtt   2700
atgttagtat taagaacgtt atttatattt caaatttttc tttttttttct gtacagacgc   2760
gtgtacgcat gtaacattat actgaaaacc ttgcttgaga aggttttggg acgctcgaag   2820
gctttaattt gcaagcttat cgatgataag ctgtcaaaca tgagaattcg gtcgaaaaaa   2880
gaaaaggaga gggccaagag ggagggcatt ggtgactatt gagcacgtga gtatacgtga   2940
ttaagcacac aaaggcagct tggagtatgt ctgttattaa tttcacaggt agttctggtc   3000
cattggtgaa agtttgcggc ttgcagagca cagaggccgc agaatgtgct ctagattccg   3060
atgctgactt gctgggtatt atatgtgtgc ccaatagaaa gagaacaatt gacccggtta   3120
```

```
ttgcaaggaa aatttcaagt cttgtaaaag catataaaaa tagttcaggc actccgaaat      3180
acttggttgg cgtgtttcgt aatcaaccta aggaggatgt tttggctctg gtcaatgatt      3240
acggcattga tatcgtccaa ctgcatggag atgagtcgtg gcaagaatac caagagttcc      3300
tcggtttgcc agttattaaa agactcgtat ttccaaaaga ctgcaacata ctactcagtg      3360
cagcttcaca gaaacctcat tcgtttattc ccttgtttga ttcagaagca ggtgggacag      3420
gtgaactttt ggattggaac tcgatttctg actgggttgg aaggcaagag agccccgaaa      3480
gcttacattt tatgttagct ggtggactga cgccagaaaa tgttggtgat gcgcttagat      3540
taaatggcgt tattggtgtt gatgtaagcg gaggtgtgga cacaaatggt gtaaaagact      3600
ctaacaaaat agcaaatttc gtcaaaaatg ctaagaaata ggttattact gagtagtatt      3660
tatttaagta ttgtttgtgc acttgcctgc agcttctcaa tgatattcga atacgctttg      3720
aggagataca gcctaatatc gacaaactg ttttacagat ttacgatcgt acttgttacc      3780
catcattgaa ttttgaacat ccgaacctgg gagtttttccc tgaaacagat agtatatttg      3840
aacctgtata ataatatata gtctagcgct ttacggaaga caatgtatgt atttcggttc      3900
ctggagaaac tattgcatct attgcatagg taatcttgca cgtcgcatcc ccggttcatt      3960
ttctgcgttt ccatcttgca cttcaatagc atatctttgt taacgaagca tctgtgcttc      4020
attttgtaga caaaaatgc aacgcgagag cgctaatttt tcaaacaaag aatctgagct      4080 gcattttac agaacagaaa tgcaacgcga aagcgctatt ttaccaacga gaatctgtg      4140 cttcattttt gtaaaacaaa aatgcaacgc gagagcgcta atttttcaaa caaagaatct      4200
gagctgcatt tttacagaac agaaatgcaa cgcgagagcg ctattttacc aacaaagaat      4260
ctatacttct tttttgttct acaaaaatgc atcccgagag cgctattttt ctaacaaagc      4320
atcttagatt acttttttc tcctttgtgc gctctataat gcagtctctt gataactttt      4380
tgcactgtag gtccgttaag gttagaagaa ggctactttg gtgtctattt tctcttccat      4440
aaaaaaagcc tgactccact tcccgcgttt actgattact agcgaagctg cgggtgcatt      4500
ttttcaagat aaaggcatcc ccgattatat tctataccga tgtggattgc gcatactttg      4560
tgaacagaaa gtgatagcgt tgatgattct tcattggtca gaaaattatg aacggtttct      4620 tctatttttgt ctctatatac tacgtatagg aaatgtttac attttcgtat tgtttcgat      4680 tcactctatg aatagttctt actacaattt ttttgtctaa agagtaatac tagagataaa      4740
cataaaaaat gtagaggtcg agtttagatg caagttcaag gagcgaaagg tggatgggta      4800
ggttatatag ggatatagca cagagatata tagcaaagag atactttga gcaatgttg      4860 tggaagcggt attcgcaata ttttagtagc tcgttacagt ccggtgcgtt tttggttttt      4920
tgaaagtgcg tcttcagagc gcttttggtt ttcaaaagcg ctctgaagtt cctatacttt      4980
ctagagaata ggaacttcgg aataggaact tcaaagcgtt tccgaaaacg agcgcttccg      5040
aaaatgcaac gcgagctgcg cacatacagc tcactgttca cgtcgcacct atatctgcgt      5100
gttgcctgta tatatatata catgagaaga acggcatagt gcgtgtttat gcttaaatgc      5160
gtacttatat gcgtctattt atgtaggatg aaaggtagtc tagtacctcc tgtgatatta      5220
tcccattcca tgcggggtat cgtatgcttc cttcagcact accctttagc tgttctatat      5280
gctgccactc ctcaattgga ttagtctcat ccttcaatgc tatcatttcc tttgatattg      5340
gatcatatgc atagtaccga gaaactagtg cgaagtagtg atcaggtatt gctgttatct      5400
gatgagtata cgttgtcctg gccacggcag aagcacgctt atcgctccaa tttcccacaa      5460
cattagtcaa ctccgttagg cccttcattg aaagaaatga ggtcatcaaa tgtcttccaa      5520
```

```
tgtgagattt tgggccattt tttatagcaa agattgaata aggcgcattt ttcttcaaag      5580
ctttattgta cgatctgact aagttatctt ttaataattg gtattcctgt ttattgcttg      5640
aagaattgcc ggtcctattt actcgtttta ggactggttc agaattcttg aagacgaaag      5700
ggcctcgtga tacgcctatt tttataggtt aatgtcatga taataatggt ttcttagacg      5760
tcaggtggca cttttcgggg aaatgtgcgc ggaaccccta tttgtttatt tttctaaata      5820
cattcaaata tgtatccgct catgagacaa taaccctgat aaatgcttca ataatattga      5880
aaaaggaaga gtatgagtat tcaacatttc cgtgtcgccc ttattccctt ttttgcggca      5940
ttttgccttc ctgtttttgc tcacccagaa acgctggtga agtaaaaga tgctgaagat      6000 cagttgggtg cacgagtggg ttacatcgaa ctggatctca acagcggtaa gatccttgag      6060
agttttcgcc ccgaagaacg ttttccaatg atgagcactt taaagttct gctatgtggc        6120 gcggtattat cccgtgttga cgccgggcaa gagcaactcg gtcgccgcat acactattct      6180
cagaatgact tggttgagta ctcaccagtc acagaaaagc atcttacgga tggcatgaca      6240
gtaagagaat tatgcagtgc tgccataacc atgagtgata acactgcggc caacttactt      6300
ctgacaacga tcggaggacc gaaggagcta accgcttttt tgcacaacat ggggatcat       6360 gtaactcgcc ttgatcgttg ggaaccggag ctgaatgaag ccataccaaa cgacgagcgt      6420
gacaccacga tgcctgcagc aatggcaaca acgttgcgca aactattaac tggcgaacta      6480
cttactctag cttcccggca acaattaata gactggatgg aggcggataa agttgcagga      6540
ccacttctgc gctcggccct tccggctggc tggtttattg ctgataaatc tggagccggt      6600
gagcgtgggt ctcgcggtat cattgcagca ctggggccag atggtaagcc ctcccgtatc      6660
gtagttatct acacgacggg gagtcaggca actatggatg aacgaaatag acagatcgct      6720
gagataggtg cctcactgat taagcattgg taactgtcag accaagttta ctcatatata      6780
ctttagattg atttaaaact tcattttta tttaaaagga tctaggtgaa gatcctttt        6840 gataatctca tgaccaaaat cccttaacgt gagttttcgt tccactgagc gtcagacccc      6900
gtagaaaaga tcaaaggatc ttcttgagat cctttttttc tgcgcgtaat ctgctgcttg      6960
caaacaaaaa aaccaccgct accagcggtg gtttgtttgc cggatcaaga gctaccaact      7020
ctttttccga aggtaactgg cttcagcaga gcgcagatac caaatactgt ccttctagtg      7080
tagccgtagt taggccacca cttcaagaac tctgtagcac cgcctacata cctcgctctg      7140
ctaatcctgt taccagtggc tgctgccagt ggcgataagt cgtgtcttac cgggttggac      7200
tcaagacgat agttaccgga taaggcgcag cggtcgggct gaacgggggg ttcgtgcaca      7260
cagcccagct tggagcgaac gacctacacc gaactgagat acctacagcg tgagctatga      7320
gaaagcgcca cgcttcccga agggagaaag gcggacaggt atccggtaag cggcagggtc      7380
ggaacaggag agcgcacgag ggagcttcca gggggaaacg cctggtatct ttatagtcct      7440
gtcgggtttc gccacctctg acttgagcgt cgatttttgt gatgctcgtc aggggggcgg      7500
agcctatgga aaaacgccag caacgcggcc ttttacggt tcctggcctt ttgctggcct        7560
tttgctcaca tgttctttcc tgcgttatcc cctgattctg tggataaccg tattaccgcc      7620
tttgagtgag ctgataccgc tcgccgcagc cgaacgaccg agcgcagcga gtcagtgagc      7680
gaggaagcgg aagagcgcct gatgcggtat tttctcctta cgcatctgtg cggtatttca      7740
caccgcatat ggtgcactct cagtacaatc tgctctgatg ccgcatagtt aagccagtat      7800
acactccgct atcgctacgt gactgggtca tggctgcgcc ccgacacccg ccaacacccg      7860
```

```
ctgacgcgcc ctgacgggct tgtctgctcc cggcatccgc ttacagacaa gctgtgaccg    7920
tctccgggag ctgcatgtgt cagaggtttt caccgtcatc accgaaacgc gcgaggcag     7979
```

<210> SEQ ID NO 10
<211> LENGTH: 9952
<212> TYPE: DNA
<213> ORGANISM: Artificial Sequence
<220> FEATURE:
<223> OTHER INFORMATION: yeast expression vector for the E. coli
      glucuronidase gene pRS425-GPD-UbGUS <400> SEQUENCE: 10

```
gacgaaaggg cctcgtgata cgcctatttt tataggttaa tgtcatgata ataatggttt      60
cttagtatga tccaatatca aaggaaatga tagcattgaa ggatgagact aatccaattg     120
aggagtggca gcatatagaa cagctaaagg gtagtgctga aggaagcata cgatacccg     180 catggaatgg gataatatca caggaggtac tagactacct ttcatcctac ataaatagac    240
gcatataagt acgcatttaa gcataaacac gcactatgcc gttcttctca tgtatatata    300
tatacaggca acacgcagat ataggtgcga cgtgaacagt gagctgtatg tgcgcagctc    360
gcgttgcatt ttcggaagcg ctcgttttcg gaaacgcttt gaagttccta ttccgaagtt    420
cctattctct agaaagtata ggaacttcag agcgcttttg aaaaccaaaa gcgctctgaa    480
gacgcacttt caaaaaacca aaacgcacc ggactgtaac gagctactaa aatattgcga     540
ataccgcttc cacaaacatt gctcaaaagt atctcttgtc tatatatctc tgtgctatat    600
ccctatataa cctacccatc cacctttcgc tccttgaact tgcatctaaa ctcgacctct    660
acatttttta tgtttatctc tagtattact ctttagacaa aaaaattgta gtaagaacta    720
ttcatagagt gaatcgaaaa caatacgaaa atgtaaacat ttcctatacg tagtatatag    780
agacaaaata aagaaaccg ttcataattt tctgaccaat gaagaatcat caacgctatc     840
actttctgtt cacaaagtat gcgcaatcca catcggtata gaatataatc ggggatgcct    900
ttatcttgaa aaaatgcacc cgcagcttcg ctagtaatca gtaaacgcgg gaagtggagt    960
caggcttttt ttatggaaga gaaaatagac accaaagtag ccttcttcta accttaacgg   1020
acctacagtg caaaaagtta tcaagagact gcattataga gcgcacaaag gagaaaaaaa   1080
gtaatctaag atgctttgtt agaaaaatag cgctctcggg atgcattttt gtagaacaaa   1140
aaagaagtat agattctttg ttggtaaaat agcgctctcg cgttgcattt ctgttctgta   1200
aaaatgcagc tcagattctt tgtttgaaaa attagcgctc tcgcgttgca ttttttgttt   1260
acaaaaatga agcacagatt cttcgttggt aaaatagcgc tttcgcgttg catttctgtt   1320
ctgtaaaaat gcagctcaga ttctttgttt gaaaaattag cgctctcgcg ttgcattttt   1380
gttctacaaa atgaagcaca gatgcttcgt tcaggtggca cttttcgggg aaatgtgcgc   1440
ggaaccccta tttgtttatt tttctaaata cattcaaata tgtatccgct catgagacaa   1500
taaccctgat aaatgcttca ataatattga aaaaggaaga gtatgagtat tcaacatttc   1560
cgtgtcgccc ttattccctt ttttgcggca ttttgccttc ctgttttgc tcacccagaa     1620 acgctggtga agtaaaaga tgctgaagat cagttgggtg cacgagtggg ttacatcgaa     1680
ctggatctca acagcggtaa gatccttgag agttttcgcc ccgaagaacg ttttccaatg    1740
atgagcactt ttaaagttct gctatgtggc gcggtattat cccgtattga cgccgggcaa    1800
gagcaactcg gtcgccgcat acactattct cagaatgact tggttgagta ctcaccagtc    1860
acagaaaagc atcttacgga tggcatgaca gtaagagaat tatgcagtgc tgccataacc    1920
```

```
atgagtgata acactgcggc caacttactt ctgacaacga tcggaggacc gaaggagcta   1980
accgctttt  tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcattttttaa  2460
tttaaaagga tctaggtgaa gatcctttt gataatctca tgaccaaaat cccttaacgt   2520
gagttttcgt tccactgagc gtcagacccc gtagaaaaga tcaaaggatc ttcttgagat   2580
ccttttttc  tgcgcgtaat ctgctgcttg caaacaaaaa aaccaccgct accagcggtg   2640
gtttgtttgc cggatcaaga ctaccaact  cttttccga aggtaactgg cttcagcaga   2700
gcgcagatac caaatactgt ccttctagtg tagccgtagt taggccacca cttcaagaac   2760
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacgggggg ttcgtgcaca cagcccagct tggagcgaac gacctacacc   2940
gaactgagat acctacagcg tgagctatga gaaagcgcca cgcttcccga agggagaaag   3000
gcggacaggt atccggtaag cggcagggtc ggaacaggag agcgcacgag ggagcttcca   3060
gggggaaacg cctggtatct ttatagtcct gtcgggtttc gccacctctg acttgagcgt   3120
cgatttttgt gatgctcgtc aggggggcgg agcctatgga aaaacgccag caacgcggcc   3180
ttttttacggt tcctggcctt tgctggcct  tttgctcaca tgttctttcc tgcgttatcc   3240
cctgattctg tggataaccg tattaccgcc tttgagtgag ctgataccgc tcgccgcagc   3300
cgaacgaccg agcgcagcga gtcagtgagc gaggaagcgg aagagcgccc aatacgcaaa   3360
ccgcctctcc ccgcgcgttg gccgattcat taatgcagct ggcacgacag gtttcccgac   3420
tggaaagcgg gcagtgagcg caacgcaatt aatgtgagtt acctcactca ttaggcaccc   3480
caggctttac actttatgct tccggctcct atgttgtgtg gaattgtgag cggataacaa   3540
tttcacacag gaaacagcta tgaccatgat tacgccaagc gcgcaattaa ccctcactaa   3600
agggaacaaa agctggagct cgtttatcat tatcaatact cgccatttca aagaatacgt   3660
aaataattaa tagtagtgat tttcctaact ttatttagtc aaaaaattag ccttttaatt   3720
ctgctgtaac ccgtacatgc caaaataggg ggcgggttac acagaatata taacactgat   3780
ggtgcttggg tgaacaggtt tattcctggc atccactaaa tataatggag cccgcttttt   3840
aagctggcat ccagaaaaaa aagaatccc  agcaccaaaa tattgttttc ttcaccaacc   3900
atcagttcat aggtccattc tcttagcgca actacagaga acagggcaca aacaggcaaa   3960
aaacgggcac aacctcaatg gagtgatgca acctgcctgg agtaaatgat gacacaaggc   4020
aattgaccca cgcatgtatc tatctcattt tcttacacct tctattacct tctgctctct   4080
ctgatttgga aaaagctgaa aaaaaggtt  taaccagtt  ccctgaaatt attcccctac   4140
ttgactaata agtatataaa gacggtaggt attgattgta attctgtaaa tctatttctt   4200
aaacttctta aattctactt ttatagttag tctttttttt agttttaaaa caccaagaac   4260
ttagtttcga cggattctag aactagtgga tccaagaatt cattatgcag atcttcgtca   4320
```

```
agacgttaac cggtaaaacc ataactctag aagttgaatc ttccgatacc atcgacaacg   4380
ttaagtcgaa aattcaagac aaggaaggca ttccacctga tcaacaaaga ttgatctttg   4440
ccggtaagca gctcgaggac ggtagaacgc tgtctgatta caacattcag aaggagtcga   4500
ccttacatct tgtcttaaga ctaagaggtg gtatggaatt catgttacgt cctgtagaaa   4560
ccccaacccg tgaaatcaaa aaactcgacg gcctgtgggc attcagtctg gatcgcgaaa   4620
actgtggaat tgatcagcgt tggtgggaaa gcgcgttaca agaaagccgg gcaattgctg   4680
tgccaggcag ttttaacgat cagttcgccg atgcagatat tcgtaattat gcggcaacg   4740 tctggtatca gcgcgaagtc tttataccga aaggttgggc aggccagcgt atcgtgctgc   4800
gtttcgatgc ggtcactcat tacggcaaag tgtgggtcaa taatcaggaa gtgatggagc   4860
atcagggcgg ctatacgcca tttgaagccg atgtcacgcc gtatgttatt gccgggaaaa   4920
gtgtacgtat caccgtttgt gtgaacaacg aactgaactg gcagactatc cgccgggaa   4980 tggtgattac cgacgaaaac ggcaagaaaa agcagtctta cttccatgat ttctttaact   5040
atgccggaat ccatcgcagc gtaatgctct acaccacgcc gaacacctgg gtggacgata   5100
tcaccgtggt gacgcatgtc gcgcaagact gtaaccacgc gtctgttgac tggcaggtgg   5160
tggccaatgg tgatgtcagc gttgaactgc gtgatgcgga tcaacaggtg gttgcaactg   5220
gacaaggcac tagcgggact ttgcaagtgg tgaatccgca cctctggcaa ccgggtgaag   5280
gttatctcta tgaactgtgc gtcacagcca aaagccagac agagtgtgat atctacccgc   5340
ttcgcgtcgg catccggtca gtggcagtga agggccaaca gttcctgatt aaccacaaac   5400
cgttctactt tactggcttt ggtcgtcatg aagatgcgga cttacgtggc aaaggattcg   5460
ataacgtgct gatggtgcac gaccacgcat taatggactg gattgggcc aactcctacc   5520 gtacctcgca ttacccttac gctgaagaga tgctcgactg ggcagatgaa catggcatcg   5580
tggtgattga tgaaactgct gctgtcggct ttaacctctc tttaggcatt ggtttcgaag   5640
cgggcaacaa gccgaaagaa ctgtacagcg aagaggcagt caacgggaa actcagcaag   5700 cgcacttaca ggcgattaaa gagctgatag cgcgtgacaa aaaccaccca gcgtggtga   5760 tgtggagtat tgccaacgaa ccggataccc gtccgcaagt gcacgggaat atttcgccac   5820
tggcggaagc aacgcgtaaa ctcgacccga cgcgtccgat cacctgcgtc aatgtaatgt   5880
tctgcgacgc tcacaccgat accatcagcg atctctttga tgtgctgtgc ctgaaccgtt   5940 attacgatg gtatgtccaa gcggcgatt tggaaacggc agagaaggta ctggaaaaag   6000
aacttctggc ctggcaggag aaactgcatc agccgattat catcaccgaa tacggcgtgg   6060
atacgttagc cgggctgcac tcaatgtaca ccgacatgtg gagtgaagag tatcagtgtg   6120
catggctgga tatgtatcac cgcgtctttg atcgcgtcag cgccgtcgtc ggtgaacagg   6180
tatggaattt cgccgatttt gcgacctcgc aaggcatatt gcgcgttggc ggtaacaaga   6240
aagggatctt cactcgcgac cgcaaaccga gtcggcggc ttttctgctg caaaaacgct   6300
ggactggcat gaacttcggt gaaaaccgc agcagggagg caaacaatga gaatcccatc   6360
aagcttatcg ataccgtcga cctcgagtgc aaattaaagc cttcgagcgt cccaaaacct   6420
tctcaagcaa ggttttcagt ataatgttac atgcgtacac gcgtctgtac agaaaaaaaa   6480 gaaaatttg aaatataaat aacgttctta atactaacat aactataaaa aaataaatag   6540
ggacctagac ttcaggttgt ctaactcctt cctttccggt tagagcggat gtgggggag   6600 ggcgtgaatg taagcgtgac ataactaatt acatggtacc caattcgccc tatagtgagt   6660
cgtattacgc gcgctcactg gccgtcgttt tacaacgtcg tgactgggaa aaccctggcg   6720
```

-continued

```
ttacccaact taatcgcctt gcagcacatc ccccttcgc cagggctgc aggaattcga      6780
tatcaagctt atcgataccg tcgacctcga ggggggcc  ggtacccaat cgccctata      6840
gtgagtcgta ttacgcgcgc tcactggccg tcgttttaca acgtcgtgac tgggaaaacc    6900
ctggcgttac ccaacttaat cgccttgcag cacatccccc tttcgccagc tggcgtaata    6960
gcgaagaggc ccgcaccgat cgcccttccc aacagttgcg cagcctgaat ggcgaatggc    7020
gcgacgcgcc ctgtagcggc gcattaagcg cggcgggtgt ggtggttacg cgcagcgtga    7080
ccgctacact tgccagcgcc ctagcgcccg ctcctttcgc tttcttccct tcctttctcg    7140
ccacgttcgc cggctttccc cgtcaagctc taaatcgggg gctcccttta gggttccgat    7200
ttagtgcttt acggcacctc gaccccaaaa aacttgatta gggtgatggt tcacgtagtg    7260
ggccatcgcc ctgatagacg ttttttcgcc ctttgacgtt ggagtccacg ttctttaata    7320
gtggactctt gttccaaact ggaacaacac tcaaccctat ctcggtctat tcttttgatt    7380
tataagggat tttgccgatt tcggcctatt ggttaaaaaa tgagctgatt taacaaaaat    7440
ttaacgcgaa ttttaacaaa atattaacgt ttacaatttc tgatgcggt  attttctcct    7500
tacgcatctg tgcggtattt cacaccgcat atcgacggtc gaggagaact tctagtatat    7560
ccacatacct aatattattg ccttattaaa aatggaatcc caacaattac atcaaaatcc    7620
acattctctt caaaatcaat tgtcctgtac ttccttgttc atgtgtgttc aaaaacgtta    7680
tatttatagg ataattatac tctatttctc aacaagtaat tggttgtttg gccgagcggt    7740
ctaaggcgcc tgattcaaga aatatcttga ccgcagttaa ctgtgggaat actcaggtat    7800
cgtaagatgc aagagttcga atctcttagc aaccattatt ttttcctca  acataacgag    7860
aacacacagg ggcgctatcg cacagaatca aattcgatga ctggaaattt tttgttaatt    7920
tcagaggtcg cctgacgcat ataccttttt caactgaaaa attgggagaa aaaggaaagg    7980
tgagaggccg gaaccggctt ttcatataga atagagaagc gttcatgact aaatgcttgc    8040
atcacaatac ttgaagttga caatattatt taaggaccta ttgttttttc caataggtgg    8100
ttagcaatcg tcttactttc taacttttct tacctttttac atttcagcaa tatatatata   8160
tatttcaagg atataccatt ctaatgtctg cccctatgtc tgccctaag  aagatcgtcg    8220
ttttgccagg tgaccacgtt ggtcaagaaa tcacagccga agccattaag gttcttaaag    8280
ctatttctga tgttcgttcc aatgtcaagt tcgatttcga aaatcattta attggtggtg    8340
ctgctatcga tgctacaggt gtcccacttc cagatgaggc gctggaagcc tccaagaagg    8400
ttgatgccgt tttgttaggt gctgtggctg gtcctaaatg gggtaccggt agtgttagac    8460
ctgaacaagg tttactaaaa atccgtaaag aacttcaatt gtacgccaac ttaagaccat    8520
gtaactttgc atccgactct cttttagact tatctccaat caagccacaa tttgctaaag    8580
gtactgactt cgttgttgtc agagaattag tgggaggtat ttactttggt aagagaaagg    8640
aagacgatgg tgatggtgtc gcttgggata gtgaacaata caccgttcca gaagtgcaaa    8700
gaatcacaag aatggccgct ttcatggccc tacaacatga gccaccattg cctatttggt    8760
ccttggataa agctaatctt ttggcctctt caagattatg gagaaaaact gtggaggaaa    8820
ccatcaagaa cgaattccct acattgaagg ttcaacatca attgattgat tctgccgcca    8880
tgatcctagt taagaaccca acccacctaa atggtatat  aatcaccagc aacatgtttg    8940
gtgatatcat ctccgatgaa gcctccgtta tcccaggttc cttgggtttg ttgccatctg    9000
cgtccttggc ctctttgcca gacaagaaca ccgcatttgg tttgtacgaa ccatgccacg    9060
gttctgctcc agatttgcca aagaataagg ttgaccctat cgccactatc ttgtctgctg    9120
```

```
                                                -continued caatgatgtt gaaattgtca ttgaacttgc ctgaagaagg taaggccatt gaagatgcag    9180
ttaaaaaggt tttggatgca ggtatcagaa ctggtgattt aggtggttcc aacagtacca    9240
ccgaagtcgg tgatgctgtc gccgaagaag ttaagaaaat ccttgcttaa aaagattctc    9300 ttttttatg atatttgtac ataaacttta taatgaaat tcataataga aacgacacga      9360
aattacaaaa tggaatatgt tcataggta gacgaaacta tatacgcaat ctacatacat    9420
ttatcaagaa ggagaaaaag gaggatagta aaggaataca ggtaagcaaa ttgatactaa    9480
tggctcaacg tgataaggaa aaagaattgc actttaacat taatattgac aaggaggagg    9540
gcaccacaca aaaagttagg tgtaacagaa aatcatgaaa ctacgattcc taatttgata    9600
ttggaggatt ttctctaaaa aaaaaaaaat acaacaaata aaaaacactc aatgacctga    9660
ccatttgatg gagtttaagt caataccttc ttgaagcatt tcccataatg gtgaaagttc    9720
cctcaagaat tttactctgt cagaaacggc cttacgacgt agtcgatatg gtgcactctc    9780
agtacaatct gctctgatgc cgcatagtta agccagcccc gacacccgcc aacacccgct    9840
gacgcgccct gacgggcttg tctgctcccg gcatccgctt acagacaagc tgtgaccgtc    9900
tccgggagct gcatgtgtca gaggttttca ccgtcatcac cgaaacgcgc ga             9952
```